United States Patent
Hashimoto et al.

(10) Patent No.: US 11,353,418 B2
(45) Date of Patent: Jun. 7, 2022

(54) NUCLEIC ACID REACTION TOOL, NUCLEIC ACID DETECTION/QUANTIFICATION KIT, AND NUCLEIC ACID DETECTION/QUANTIFICATION METHOD

(71) Applicant: KABUSHIKI KAISHA TOSHIBA, Tokyo (JP)

(72) Inventors: Koji Hashimoto, Atsugi (JP); Keiko Ito, Kawasaki (JP); Mika Inada, Ota (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 186 days.

(21) Appl. No.: 16/115,870

(22) Filed: Aug. 29, 2018

(65) Prior Publication Data
US 2019/0285567 A1    Sep. 19, 2019

(30) Foreign Application Priority Data

Mar. 13, 2018 (JP) .............................. JP2018-045901

(51) Int. Cl.
| | | |
|---|---|---|
| *G01N 27/327* | (2006.01) | |
| *B01L 3/00* | (2006.01) | |
| *C12Q 1/6844* | (2018.01) | |
| *B01L 7/00* | (2006.01) | |

(52) U.S. Cl.
CPC .... *G01N 27/3276* (2013.01); *B01L 3/502761* (2013.01); *B01L 3/527* (2013.01); *B01L 7/525* (2013.01); *C12Q 1/6846* (2013.01); *B01L 2300/0645* (2013.01); *B01L 2300/0663* (2013.01); *B01L 2300/0809* (2013.01); *B01L 2300/0816* (2013.01); *B01L 2300/0858* (2013.01); *B01L 2300/0883* (2013.01); *B01L 2300/161* (2013.01); *B01L 2300/1805* (2013.01)

(58) Field of Classification Search
CPC ............................. B01L 3/5027; B01L 3/527
See application file for complete search history.

(56) References Cited

U.S. PATENT DOCUMENTS

| | | | |
|---|---|---|---|
| 6,518,027 B2 | 2/2003 | Kambara | |
| 9,359,638 B2 | 6/2016 | Takahashi et al. | |
| 2001/0018412 A1 | 8/2001 | Kambara | |
| 2001/0019824 A1 | 9/2001 | Kambara | |
| 2002/0102600 A1 | 8/2002 | Kambara | |
| 2014/0148359 A1* | 5/2014 | Takahashi | ......... B01L 3/502761 506/9 |
| 2018/0127814 A1 | 5/2018 | Hashimoto et al. | |
| 2019/0001327 A1* | 1/2019 | Wu | .......................... C12M 1/34 |

FOREIGN PATENT DOCUMENTS

| | | | |
|---|---|---|---|
| JP | 2000-342258 | 12/2000 | |
| JP | 2013-51958 | 3/2013 | |
| JP | 2013-116125 | 6/2013 | |
| JP | 5216928 | 6/2013 | |
| JP | 2013-198417 A | 10/2013 | |
| JP | 2018-68258 | 5/2018 | |
| WO | WO-2017028758 A1 * | 2/2017 | ........ B01L 3/502707 |

OTHER PUBLICATIONS

Dutta, Effect of channel geometry on solute dispersion in pressure-driven microfluidic systems, Microfluid Nanofluid, 2: 275-290, 2006. (Year: 2006).*

Olanrewaju, Capillary microfluidics in microchannels: from microfluidic networks to capillaric circuits, Lab on a Chip, 18(16): 2323-2347, 2018. (Year: 2018).*

Hashimoto et al., "A novel voltammetric approach for real-time electrochemical detection of targeted nucleic acid sequences using LAMP", Analytical Biochemistry, 2017, vol. 539, pp. 113-117.

* cited by examiner

*Primary Examiner* — Samuel C Woolwine
*Assistant Examiner* — Carolyn L Greene
(74) *Attorney, Agent, or Firm* — Oblon, McClelland, Maier & Neustadt, L.L.P.

(57) ABSTRACT

According to one embodiment, a nucleic acid reaction tool includes a support having a first surface, a covering body having a second surface, and a groove opened on the second surface, and a primer set. The covering body is in contact with the support to form a reaction space surrounded by the first surface and the groove. The groove includes, on an inner surface of the reaction space, rising surfaces opposed to each other, and a rear surface connecting one end of the side surfaces, and a primer fixing region to which the primer set is fixed, the primer fixing region being located at a corner where the one end of the side surfaces connected to the rear surface in the reaction space.

18 Claims, 33 Drawing Sheets
(1 of 33 Drawing Sheet(s) Filed in Color)
Specification includes a Sequence Listing.

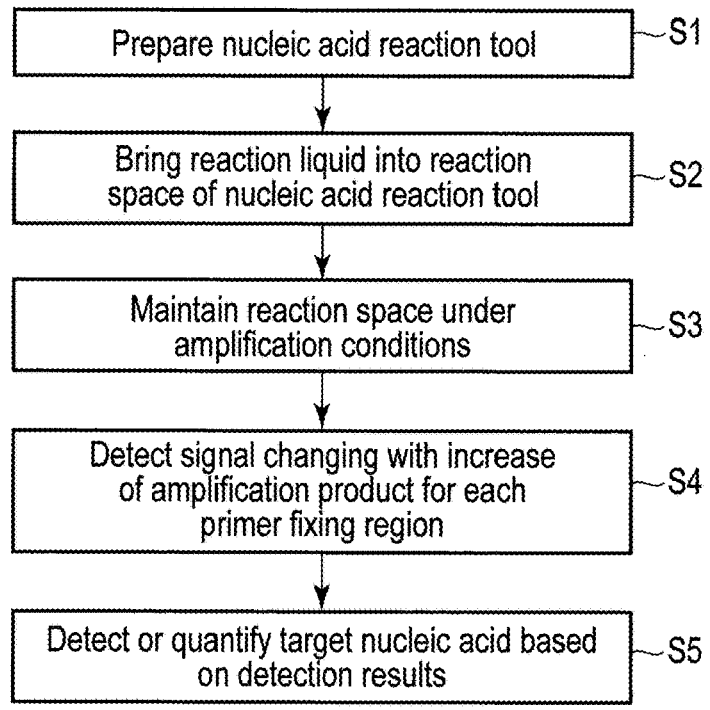
F I G. 5
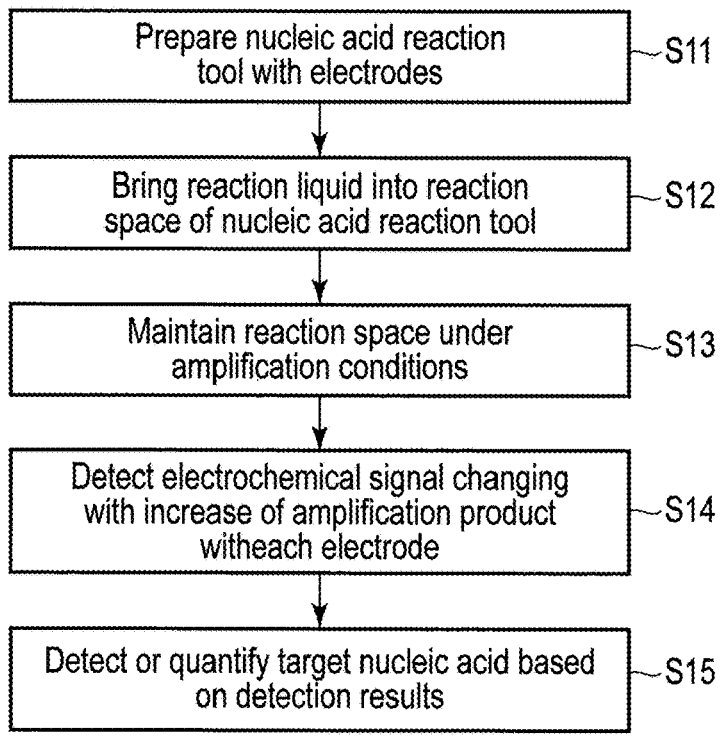
F I G. 6

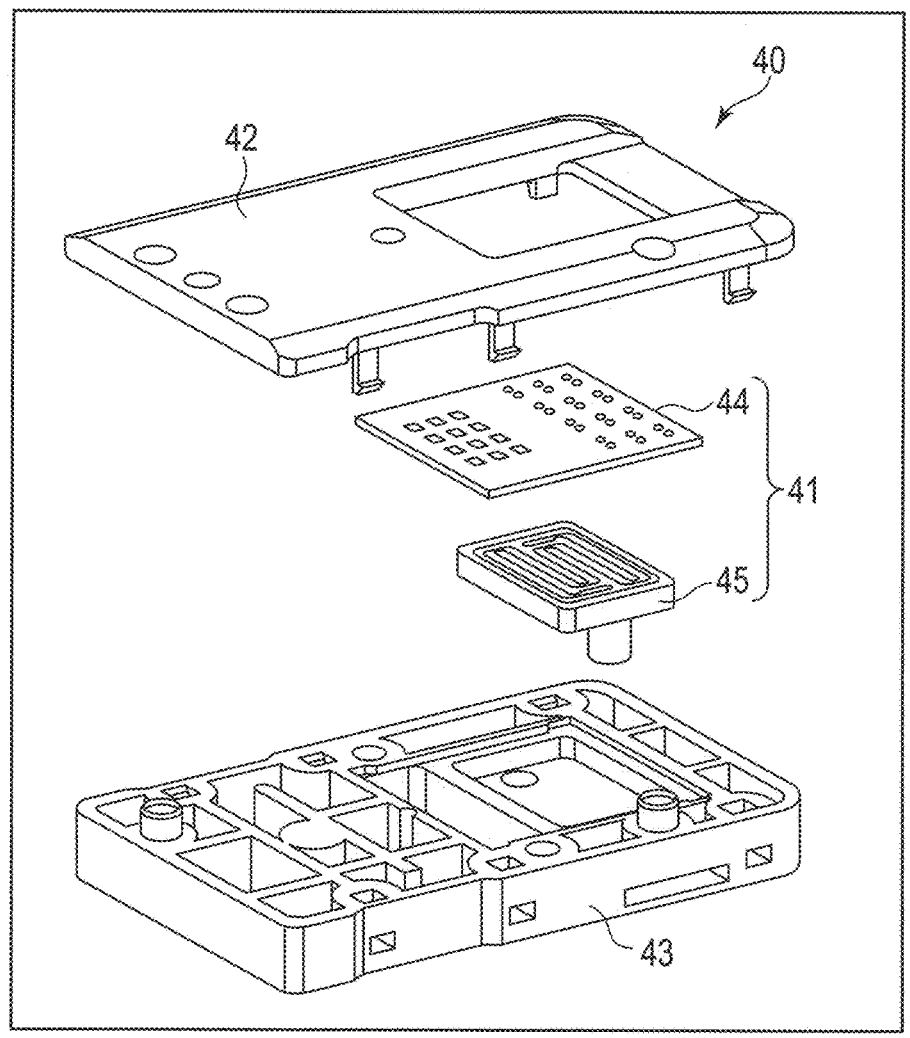
F I G. 11

|    | A1   | A2   | A3   | A4   | A5   | A6   | A7   | A8   | A9   | A10  | A11  | A12  | A13  | A14  | A15  | A16  | A17  | A18  | A19  | A20  |
|----|------|------|------|------|------|------|------|------|------|------|------|------|------|------|------|------|------|------|------|------|
| 1  | -0.5 | 0    | 0.05 | 0.21 | -1.7 | -1.7 | 0.99 | 1.1  | 0.9  | 1.25 | 0.66 | 0.93 | 1.52 | 1.42 | 2.88 | 2.55 | 3.36 | 3.36 | 1.17 | 1.2  |
| 2  | 0.54 | 0.52 | 0.49 | 0.53 | 0.44 | 0.55 | 1.22 | 1.49 | 1.68 | 1.71 | 2.34 | 2.39 | 2.13 | 1.38 | 1.24 | 1.08 | 0.54 | 0.48 | -0.2 | -0.2 |
| 3  | 0.14 | 0.12 | 0.4  | 0.13 | 0.32 | 0.23 | 0.43 | 0.5  | 0.64 | 0.79 | 1.17 | 1.38 | 0.91 | 0.75 | 0.44 | 0.35 | 0    | -0.1 | -0.2 | -0.3 |
| 4  | 0.2  | 0.18 | 0.14 | 0.06 | 0.33 | 0.38 | 0.29 | 0.25 | 0.5  | 0.6  | 0.86 | 0.86 | 0.42 | 0.55 | 0.05 | 0.03 | -0.1 | -0.2 | -0.2 | -0.1 |
| 5  | 0.2  | 0.2  | -0.2 | 0.2  | -0.1 | -0.1 | 0    | 0.11 | 0.29 | 0.26 | 0.42 | 0.49 | 0.23 | 0.3  | 0.01 | -0.1 | -0.2 | -0.2 | -0.1 | -0.1 |
| 6  | -0.2 | -0.2 | -0.3 | -0.2 | 0    | 0.3  | 0    | 0.05 | 0.01 | 0.16 | 0.45 | 0.44 | 0.16 | 0.07 | -0.1 | -0.2 | -0.4 | -0.4 | -0.3 | -0.3 |
| 7  | 0.2  | 0.3  | 0.3  | -0.3 | -0.2 | 0.3  | -0.2 | 0.1  | 0    | 0.5  | 0.16 | 0.35 | 0    | 0    | -0.4 | -0.3 | -0.4 | -0.4 | -0.2 | -0.3 |
| 8  | 0.2  | 0.3  | 0.3  | 0.3  | 0.2  | 0.2  | 0.2  | 0.2  | -0.1 | 0.2  | 0.04 | 0.12 | 0    | 0.68 | -0.3 | -0.3 | -0.5 | -0.4 | 0.4  | 0.3  |
| 9  | -0.3 | -0.2 | -0.4 | -0.3 | -0.2 | -0.2 | -0.4 | -0.3 | -0.3 | -0.3 | 0    | -0.1 | -0.6 | 0.78 | -0.3 | -0.4 | -0.5 | -0.4 | -0.2 | -0.4 |
| 10 | 0.4  | 0.4  | 0.4  | -0.4 | -0.4 | -0.2 | -0.3 | -0.3 | -0.2 | -0.2 | 0.1  | 0.01 | -0.2 | -2.7 | -0.5 | -0.4 | -0.5 | -0.4 | -0.4 | -0.4 |
| 11 | 0.3  | 0.3  | 0.4  | 0.3  | -0.3 | 0.3  | 0.3  | 0.4  | 0.3  | -0.2 | 0.2  | 0    | -0.3 | -0.3 | 0.3  | 0.3  | -0.3 | -0.4 | -0.4 | -0.4 |
| 12 | 0.4  | 0.5  | 0.4  | 0.4  | 0.3  | 0.4  | 0.3  | -0.3 | -0.2 | -0.3 | 0.2  | -0.1 | -0.3 | 0.3  | -0.4 | 0.4  | -0.4 | -0.4 | -0.4 | -0.4 |
| 13 | 0.3  | -0.2 | 0.4  | 0.3  | 0.4  | 0.7  | 0.3  | -0.3 | -0.3 | -0.3 | 0.2  | 0.2  | -0.3 | 0.3  | -0.4 | -0.4 | -0.3 | -0.4 | -0.4 | -0.5 |
| 14 | 0.3  | -0.4 | -0.3 | -0.3 | -0.3 | -0.5 | -0.3 | -0.3 | -0.2 | -0.3 | -0.2 | 0.2  | -0.4 | -0.4 | -0.4 | -0.5 | -0.4 | -0.4 | -0.4 | -0.8 |
| 15 | -0.4 | -0.2 | -0.4 | 0.4  | -0.4 | 0.4  | -0.3 | 0.4  | 0.4  | -0.2 | -0.2 | 0.2  | -0.4 | -0.2 | -0.3 | -0.3 | -0.4 | -0.4 | 0.6  | -0.6 |
| 16 | -0.5 | -0.2 | -0.4 | 0.4  | -0.5 | -0.3 | -0.3 | 0.3  | 0.4  | 0.3  | 0.2  | -0.3 | 0.5  | 0.4  | 0.4  | 0.4  | 0.4  | 0.4  | -0.3 | -0.1 |
| 17 | 0.2  | 0.2  | 0.4  | 0.6  | 0.4  | 0.4  | 0.4  | 0.4  | 0.4  | -0.4 | 0.2  | 0.2  | -0.4 | 0.4  | -0.5 | -0.5 | -0.4 | -0.4 | -0.3 | 0.1  |
| 18 | 0.2  | 0.2  | 0.5  | 0.6  | 0.5  | 0.5  | 0.3  | 0.3  | 0.3  | 0.2  | 0.2  | 0.2  | 0.3  | 0.3  | 0.4  | 0.4  | 0.4  | 0.5  | 0.4  | -0.3 |
| 19 | 0.8  | 0.2  | 0.5  | 0.7  | 0.38 | 2    | 0.4  | 0.4  | 0.3  | 0.3  | 0.3  | 0.3  | -0.4 | 0.3  | 0.3  | -0.4 | 0.4  | 0.5  | -0.5 | 0.4  |
| 20 | 0.4  | -0.5 | -0.6 | -0.9 | 3.52 | -2.5 | -0.3 | -0.4 | -0.2 | -0.4 | -0.2 | 0.3  | -0.4 | -0.3 | -0.4 | -0.3 | -0.5 | -0.5 | -0.3 | -0.6 |

FIG. 18A

| A21 | A22 | A23 | A24 | A24 | A26 | A27 | A28 | A29 | A30 | A31 | A32 | A33 | A34 | A35 | A36 | A37 | A38 | A39 | A40 |
|---|---|---|---|---|---|---|---|---|---|---|---|---|---|---|---|---|---|---|---|
| 2.04 | 2.33 | 1.93 | 1.82 | 1.41 | 1.55 | 1.79 | 1.89 | 1.34 | 0.81 | 2.84 | 3.13 | 3.41 | 3.59 | 2.92 | 2.37 | 2.09 | 1.95 | 0.38 | -0.1 |
| 0 | 0.1 | 0 | 0.06 | 0.2 | 0.4 | 0.3 | 0.3 | 0.8 | 0.7 | 0.13 | 0.16 | 0.7 | 0.83 | 0.72 | 0.46 | 0 | -0.1 | 0.6 | 0.8 |
| -0.4 | -0.4 | -0.3 | -0.2 | 0.02 | -0.4 | -0.5 | -0.6 | -0.6 | -0.4 | -0.4 | -0.1 | 0.03 | 0.07 | 0.05 | 0.05 | -0.3 | -0.4 | -0.5 | -0.5 |
| -0.4 | -0.4 | -0.2 | -0.3 | -0 | -0.4 | -0.6 | -0.5 | -0.4 | -0.2 | -0.2 | -0.3 | -0.1 | -0 | -0.3 | -0.2 | -0.5 | -0.4 | -0.4 | -0.5 |
| -0.4 | -0.4 | -0.3 | -0.3 | -0.3 | -0.4 | -0.5 | -0.6 | -0.2 | -0.4 | -0.4 | -0.5 | -0.2 | -0.1 | -0.2 | -0.3 | -0.3 | -0.5 | -0.4 | -0.5 |
| -0.4 | -0.4 | -0.4 | -0.3 | -0.3 | -0.4 | -0.6 | -0.5 | -0.4 | -0.3 | -0.2 | -0.3 | -0.3 | -0.2 | -0.3 | -0.3 | -0.3 | -0.4 | -0.4 | -0.4 |
| -0.4 | -0.4 | -0.4 | -0.4 | -0.4 | -0.2 | -0.4 | -0.4 | -0.2 | -0.3 | -0.4 | -0.4 | -0.2 | -0.3 | 0.3 | 0.5 | 0.4 | 0.3 | 0.4 | -0.4 |
| 0.5 | -0.5 | 0.4 | 0.4 | 0.4 | 0.4 | 0.4 | 0.4 | 0.3 | 0.3 | -0.4 | 0.4 | 0.3 | 0.2 | 0.3 | 0.3 | -0.3 | -0.4 | -0.3 | -0.4 |
| -0.4 | -0.3 | -0.4 | -0.4 | -0.4 | -0.4 | -0.4 | -0.5 | -0.4 | -0.4 | -0.3 | -0.3 | -0.3 | -0.3 | -0.3 | -0.3 | -0.4 | -0.4 | -0.3 | -0.4 |
| -0.4 | -0.5 | -0.4 | -0.4 | -0.4 | -0.4 | -0.5 | -0.3 | -0.4 | -0.3 | -0.4 | -0.4 | -0.4 | -0.4 | -0.3 | -0.4 | -0.4 | -0.4 | -0.3 | -0.3 |
| -0.4 | -0.4 | -0.4 | -0.4 | -0.3 | -0.3 | -0.4 | -0.4 | -0.4 | -0.4 | -0.4 | -0.4 | -0.4 | -0.4 | -0.5 | -0.3 | -0.4 | -0.4 | -0.4 | -0.4 |
| -0.5 | -0.5 | -0.4 | -0.5 | -0.4 | -0.3 | -0.5 | -0.5 | -0.5 | -0.5 | -0.5 | -0.4 | -0.4 | -0.4 | -0.3 | -0.3 | -0.3 | -0.3 | 0.3 | -0.3 |
| -0.4 | -0.4 | -0.4 | -0.4 | -0.4 | -0.3 | -0.4 | -0.7 | -0.8 | -0.6 | -0.4 | -0.4 | -0.4 | -0.4 | -0.4 | -0.4 | -0.3 | -0.4 | -0.4 | -0.4 |
| -0.4 | -0.5 | -0.4 | -0.4 | -0.3 | 0.3 | -0.6 | -0.8 | 0.9 | -0.7 | -0.5 | -0.4 | -0.3 | -0.3 | -0.3 | -0.3 | -0.3 | 0.3 | -1 | -0.9 |
| 0.4 | 0.4 | 0.4 | 0.3 | 0.4 | -0.3 | -0.5 | -0.5 | -0.8 | -0.9 | -0.4 | -0.5 | -0.4 | -0.4 | -0.5 | -0.4 | -0.4 | -0.4 | -0.7 | -1.1 |
| -0.3 | 0.3 | -0.4 | 0.4 | 0.3 | 0.3 | -0.8 | 0.6 | 0.2 | 0.6 | 0.4 | 0.3 | -0.2 | 0.2 | -0.3 | -0.3 | -0.3 | -0.4 | 0.6 | 0.04 |
| -0.4 | -0.4 | -0.3 | -0.3 | -0.3 | -0.3 | 0.8 | 0.25 | -0.3 | -0.6 | 0.4 | 0.4 | -0.3 | 0.2 | 0.4 | -0.3 | -0.4 | -0.4 | 0.18 | 0.12 |
| -0.4 | -0.4 | -0.4 | -0.3 | -0.3 | 0.3 | 0.06 | 0.1 | 0.4 | 0.6 | 0.4 | 0.4 | 0.4 | -0.3 | -0.4 | 0.3 | -0.3 | 0.4 | -0.2 | 0.1 |
| 0.5 | -0.4 | 0.3 | -0.3 | -0.3 | -0.3 | 0.83 | -0.3 | -0.3 | -0.6 | -0.4 | -0.4 | -0.4 | 0.4 | 0.4 | 0.4 | -0.4 | 0.5 | 0.5 | -0.2 |
| -0.7 | -0.4 | -0.4 | -0.3 | -0.3 | -0.3 | 0.23 | -0.3 | -0.9 | -0.7 | -0.5 | -0.5 | -0.4 | -0.3 | -0.3 | -0.4 | -0.4 | -0.4 | -1.4 | 0.99 |

FIG. 18B

| | A41 | A42 | A43 | A44 | A45 | A46 | A47 | A48 | A49 | A50 | A51 | A52 | A53 | A54 | A55 | A56 | A57 | A58 | A59 | A60 |
|---|---|---|---|---|---|---|---|---|---|---|---|---|---|---|---|---|---|---|---|---|
| | 1.02 | 0.97 | 0.8 | 0.9 | 1.57 | 1.91 | 1.25 | 0.88 | 0.6 | 0.63 | 0.81 | 0.81 | 0.12 | -0.1 | 1.52 | 1.5 | 1.79 | 1.95 | 2.57 | 2.95 |
| | 0.5 | 0.4 | 0.5 | 0.5 | 0.2 | 0.1 | 0.11 | 0 | 0.2 | 0.1 | 0.2 | 0.2 | 1 | 1.1 | 0.16 | 0.09 | 0.46 | 0.37 | 0.92 | 0.85 |
| | -0.5 | -0.6 | -0.6 | -0.6 | -0.4 | -0.2 | -0.2 | -0.2 | -0.4 | -0.5 | -0.4 | -0.5 | -0.9 | -0.2 | -0.2 | -0.2 | 0.2 | 0.03 | 0.17 | 0.38 |
| | -0.5 | -0.5 | -0.5 | -0.5 | -0.4 | -0.3 | -0.4 | -0.4 | -0.5 | -0.5 | -0.6 | 0.4 | -0.7 | -0.5 | -0.5 | -0.5 | -0.2 | -0.3 | 0 | 0.11 |
| | -0.3 | -0.5 | -0.5 | -0.5 | -0.4 | -0.4 | -0.5 | -0.5 | -0.5 | -0.5 | -0.5 | -0.5 | -0.4 | -0.4 | -0.4 | -0.4 | -0.3 | -0.3 | 0 | -0 |
| | -0.3 | -0.3 | -0.3 | -0.3 | -0.3 | -0.3 | -0.3 | -0.4 | -0.5 | -0.4 | -0.4 | -0.4 | -0.2 | -0.2 | -0.2 | -0.4 | -0.2 | -0.3 | -0 | -0 |
| | 0.4 | 0.4 | 0.5 | 0.4 | 0.4 | 0.4 | 0.4 | -0.3 | 0.3 | -0.5 | 0.5 | 0.5 | 0.2 | 0.3 | 0.4 | -0.05 | -0.5 | -0.2 | -0.1 | 0.1 |
| | -0.3 | -0.3 | -0.5 | -0.4 | -0.4 | -0.4 | -0.3 | -0.4 | -0.5 | -0.4 | -0.4 | -0.3 | 0.3 | -0.3 | 0.4 | 0.4 | 0.3 | -0.3 | -0.1 | -0.1 |
| | -0.3 | -0.4 | 0.4 | -0.4 | -0.4 | -0.4 | -0.4 | -0.5 | -0.5 | -0.5 | -0.4 | -0.4 | -0.3 | -0.3 | -0.4 | -0.5 | -0.4 | -0.3 | -0.1 | -0.3 |
| | -0.3 | -0.4 | -0.4 | -0.4 | -0.4 | -0.3 | -0.3 | -0.4 | -0.4 | -0.4 | -0.4 | -0.4 | 0.3 | 0.2 | 0.4 | 0.4 | 0.4 | -0.4 | -0.3 | -0.3 |
| | -0.3 | -0.4 | -0.4 | -0.4 | -0.3 | -0.4 | -0.4 | -0.3 | -0.3 | -0.3 | -0.3 | -0.3 | -0.3 | -0.3 | -0.4 | -0.4 | -0.2 | -0.4 | -0.3 | 0.3 |
| | -0.3 | -0.4 | -0.4 | -0.4 | -0.3 | -0.3 | -0.3 | -0.3 | -0.4 | -0.4 | -0.4 | -0.4 | 0.4 | -0.4 | -0.4 | -0.4 | 0.4 | -0.4 | -0.3 | 0.3 |
| | -0.4 | -0.4 | -0.4 | -0.4 | -0.3 | -0.3 | -0.3 | -0.3 | -0.4 | -0.4 | -0.4 | -0.4 | -0.5 | -0.5 | 0.5 | 0.3 | -0.2 | -0.4 | 0.3 | 0.3 |
| | -0.5 | -0.4 | -0.4 | -0.5 | -0.3 | -0.3 | -0.3 | -0.3 | -0.3 | -0.3 | -0.3 | -0.3 | -0.5 | -0.3 | -0.4 | -0.4 | -0.4 | -0.4 | 0.2 | -0.3 |
| | -0.4 | 0.3 | 0.4 | 0.4 | 0.2 | 0.3 | 0.4 | 0.3 | 0.5 | 0.4 | 0.4 | 0.3 | 0.3 | 0.5 | 0.4 | 0.4 | -0.3 | -0.3 | -0.3 | -0.2 |
| | -0.4 | 0.4 | 0.4 | 0.4 | -0.3 | 0.3 | 0.4 | 0.3 | 0.4 | 0.5 | 0.5 | 0.5 | 0.4 | 0.5 | -0.4 | 0.3 | -0.3 | -0.3 | -0.2 | -0.1 |
| | -0.6 | -0.4 | -0.4 | -0.4 | -0.3 | -0.4 | -0.3 | -0.3 | -0.3 | -0.3 | -0.4 | -0.6 | -0.5 | -0.4 | -0.4 | 0.4 | -0.3 | -0.3 | 0 | 0 |
| | -0.7 | -0.5 | -0.4 | -0.5 | -0.3 | -0.4 | -0.3 | -0.3 | -0.3 | -0.4 | -0.3 | -0.7 | -0.4 | -0.3 | -0.5 | 0.4 | 0.2 | 0.3 | 0 | 0.05 |
| | 0.05 | 0.7 | 0.4 | 0.4 | 0.3 | 0.3 | 0.4 | 0.3 | 0.3 | 0.2 | 0.4 | 0.3 | 0.3 | 0.5 | 0.4 | 0.4 | -0.3 | -0.3 | 0.22 | 0.19 |
| | 0.38 | -0.5 | 0.4 | -0.3 | -0.3 | -0.3 | -0.3 | -0.3 | -0.3 | -0.3 | -0.3 | -0.3 | -0.4 | -0.3 | -0.4 | -0.5 | -0.3 | -0.3 | 0.15 | 0.14 |
| | 0.07 | 0.4 | 0.4 | 0.4 | -0.3 | 0.3 | 0.4 | -0.3 | -0.3 | -0.3 | -0.3 | -0.3 | -0.4 | -0.3 | -0.4 | -0.5 | 0.2 | 0.3 | | |
| | -0.1 | 0.42 | -0.3 | -0.3 | -0.3 | -0.4 | -0.3 | -0.3 | -0.3 | -0.3 | -0.3 | -0.4 | -0.4 | -0.3 | -0.4 | -0.5 | -0.3 | -0.2 | | |

Primer mix fixed position → A53 A54

| -0.3 | 0.14 | -0.3 | -0.3 | -0.3 | -0.4 | -0.3 | -0.3 | -0.4 | -0.7 | 0.11 | -0.1 | -0.6 | -0.5 | -0.2 | -0.2 | 0.3 | 0.42 |
|---|---|---|---|---|---|---|---|---|---|---|---|---|---|---|---|---|---|
| -0.9 | -0.3 | -0.4 | -0.4 | -0.3 | -0.3 | -0.4 | -0.2 | -0.8 | 0.97 | 3.2 | 1.18 | -0.5 | -0.5 | -0.2 | 0.4 | 0.33 | 0.27 |
| -1.4 | -0.7 | -0.3 | -0.3 | -0.3 | -0.3 | -0.3 | -0.3 | -0.1 | 1.2 | 4.75 | 4.34 | -0.5 | -0.4 | -0.1 | 0.03 | 0.36 | 0.25 |
| -1.6 | -0.9 | -0.3 | 0.2 | 0.3 | -0.4 | 0.3 | -0.4 | 1.36 | -0.3 | 2.01 | 1.55 | -0.6 | -0.5 | -0.1 | -0 | 0.27 | 0.38 |
| 1.3 | 1.1 | 0.3 | -0.3 | 0.3 | -0.2 | 0.3 | 0.3 | 0.6 | -1.2 | 3.85 | 2.75 | 0.7 | 0.5 | 0.17 | 0 | 0.29 | 0.26 |
| -0.7 | -1.2 | -0.3 | 0.2 | -0.4 | -0.3 | -0.4 | -0.4 | -0.5 | -1.6 | 4.97 | 3.96 | -0.7 | -0.5 | 0.05 | 0.14 | 0.51 | 0.45 |
| 1.58 | -0.9 | -0.3 | 0.3 | -0.3 | -0.3 | -0.3 | -0.3 | -0.9 | -1 | 5.34 | 5.15 | -0.7 | -0.6 | 0.12 | 0.27 | 0.37 | 0.21 |
| 2.32 | 0.9 | 0.4 | -0.2 | 0.3 | 0.2 | 0.3 | 0.4 | 1.2 | 0.66 | 4.5 | 5.28 | 0.8 | 0.5 | 0.19 | 0.07 | 0.43 | 0.18 |
| 2.41 | -0.7 | -0.3 | -0.3 | -0.2 | -0.3 | -0.3 | -0.4 | -1 | 2.18 | 5.4 | 4.41 | -0.6 | -0.6 | 0.11 | -0.1 | 0.35 | 0.3 |
| 2.62 | -0.6 | -0.3 | -0.3 | -0.3 | -0.3 | -0.3 | -0.4 | 1 | 3.26 | 5.43 | 4.35 | 0.7 | -0.5 | 0.32 | 0.16 | 0.49 | 0.18 |
| 1.97 | -0.4 | -0.4 | -0.4 | -0.3 | -0.3 | -0.3 | -0.4 | -0.7 | 3.49 | 5.6 | 4.06 | -0.4 | -0.4 | 0.33 | 0 | 0.45 | 0.35 |
| 1.16 | -0.2 | -0.4 | -0.4 | -0.3 | -0.3 | -0.3 | -0.4 | 0 | 3.08 | 5.08 | 4.44 | -0.5 | -0.4 | 0.27 | 0.07 | 0.42 | 0.38 |
| 1.28 | -0.2 | -0.3 | -0.3 | -0.3 | -0.3 | -0.4 | -0.4 | 0.3 | 3.07 | 5.43 | 3.64 | -0.3 | -0.2 | 0.35 | 0.15 | 0.52 | 0.31 |
| 0.83 | -0.3 | 0.5 | 0.4 | 0.3 | 0.2 | 0.3 | 0.5 | 0.1 | 2.24 | 4.17 | 2.93 | 0.2 | -0 | 0.35 | 0.22 | 0.46 | 0.04 |
| 0.35 | -0.2 | -0.3 | -0.3 | -0.2 | -0.2 | -0.2 | -0.4 | -0.1 | 1.77 | 4.01 | 2.73 | -0.1 | 0.04 | 0.4 | -0 | 0.5 | 0.24 |
| 0.28 | 0.3 | 0.4 | 0.4 | 0.2 | 0.2 | 0.3 | 0.5 | 0.1 | 1.13 | 3.59 | 2.47 | 0.06 | 0.05 | 0.19 | 0.3 | 0.42 | 0.16 |
| 0.32 | -0.2 | -0.3 | -0.4 | -0.3 | -0.2 | -0.3 | -0.4 | 0.06 | 0.96 | 3.29 | 2.06 | 0.15 | 0.26 | 0.35 | 0.2 | 0.4 | 0.21 |
| 0.12 | -0.3 | -0.4 | -0.5 | -0.3 | -0.3 | -0.4 | -0.3 | -0.2 | 0.77 | 3.22 | 1.57 | 0.16 | 0.17 | 0.3 | 0.1 | 0.27 | 0.24 |
| -0 | -0.1 | -0.3 | -0.3 | -0.2 | -0.2 | -0.3 | -0.5 | -0.3 | 0.35 | 1.94 | 1.33 | 0.31 | 0.38 | 0.3 | 0.19 | 0.52 | 0.27 |
| 0.1 | 0.3 | 0.3 | 0.3 | 0.2 | 0.2 | 0.2 | 0.4 | 0.2 | 0.25 | 2.19 | 1.1 | 0.36 | 0.29 | 0.2 | 0.13 | 0.42 | 0.34 |

FIG. 18F

| 41 | 0.2 | 0.3 | 0.85 | 1.28 | 0.1 | 0.23 | -0.3 | -0.3 | -0.3 | -0.2 | -0.1 | -0.1 | -0.1 | 0.1 | -0.3 | -0.3 | -0.4 | -0.4 | [2.27] | 2.07 |
|---|---|---|---|---|---|---|---|---|---|---|---|---|---|---|---|---|---|---|---|---|
| 42 | 0.2 | -0.3 | 0.12 | 0.1 | 0.2 | -0.6 | -0.3 | -0.3 | -0.3 | -0.3 | -0.2 | -0.2 | -0.2 | -0.2 | -0.4 | -0.3 | -0.4 | -0.4 | 1.64 | 1.94 |
| 43 | 0.4 | 0.4 | 0.34 | 0.39 | 0.5 | -0.1 | 0.3 | -0.5 | -0.4 | -0.3 | 0.3 | -0.4 | -0.2 | -0.4 | -0.6 | -0.3 | -0.6 | -0.5 | 1.05 | 1.94 |
| 44 | 0.2 | -0.2 | 0.35 | 0.45 | -0.1 | -0.3 | -0.3 | -0.4 | -0.2 | -0.3 | -0.2 | -0.2 | -0.2 | -0.2 | -0.3 | -0.2 | -0.3 | -0.3 | 1.9 | 2.36 |
| 45 | 0.1 | 0.3 | 0.38 | 0.42 | 0.13 | 0 | 0.2 | 0.2 | 0.4 | 0.2 | 0.1 | 0.2 | 0.1 | 0.3 | 0.3 | 0.3 | 0.3 | -0.3 | 1.45 | 1.25 |
| 46 | 0.1 | 0.4 | 0.62 | 0.12 | 0.3 | 0.2 | 0.3 | 0.3 | -0.2 | -0.2 | 0.3 | -0.1 | 0.3 | -0.3 | -0.3 | 0.3 | -0.3 | -0.3 | 1.26 | 1.02 |
| 47 | -0 | 0.4 | 0.04 | -0.1 | -0.1 | -0.1 | -0.1 | -0.2 | 0.4 | 0.2 | 0.1 | 0.3 | -0.3 | -0.3 | -0.4 | -0.4 | 0.3 | 0.3 | 0.92 | 1.38 |
| 48 | 0.1 | 0.4 | 0.6 | 0.03 | 0.1 | 0.05 | 0.4 | 0.3 | -0.2 | 0.3 | 0.3 | 0.1 | -0.3 | -0.2 | -0.2 | -0.2 | 0.3 | 0.3 | 0.9 | 1.07 |
| 49 | 0.4 | 0.4 | 0.54 | 0.1 | 0.1 | 0 | 0.2 | 0.3 | 0.2 | 0.2 | 0.2 | 0.3 | -0.2 | -0.3 | -0.3 | 0.3 | 0.3 | 0.3 | 1 | 0.97 |
| 50 | 0.05 | 0.6 | 1.22 | 0.09 | 0 | 0 | -0.2 | 0.1 | -0.2 | 0.3 | 0.2 | 0.1 | 0.3 | -0.2 | 0.3 | -0.3 | -0.2 | 0.2 | 0.64 | 0.89 |
| 51 | 0.2 | 0.2 | 0.29 | 0.2 | 0.2 | 0.1 | 0.1 | 0.4 | 0.3 | 0.3 | 0.2 | 0.3 | 0.1 | 0.3 | -0.2 | -0.2 | -0.3 | 0.2 | 0.57 | 0.78 |
| 52 | -0 | 0.00 | 0.61 | 0.16 | 0 | -0.2 | -0.2 | -0.2 | 0.2 | -0.2 | -0.2 | -0.2 | -0.3 | -0.2 | -0.3 | -0.2 | -0.3 | -0.2 | 0.91 | 0.37 |
| 53 | 0.05 | 0 | 1.52 | 0.16 | 0.1 | 0.1 | 0.1 | 0.2 | -0.2 | -0.3 | -0.3 | -0.2 | -0.2 | -0.2 | -0.3 | -0.3 | -0.2 | -0.3 | 0.51 | 0.67 |
| 54 | 0 | 0.05 | 0.21 | 0.21 | 0.1 | 0.06 | 0.1 | 0.3 | 0.2 | -0.2 | -0.1 | -0.2 | -0.1 | -0.1 | -0.2 | -0.3 | -0.3 | -0.2 | 0.66 | 0.79 |
| 55 | 0.04 | 0.04 | 1.03 | 0.1 | 0.1 | 0.2 | 0.3 | 0.2 | -0.3 | -0.3 | 0.2 | 0.1 | 0.2 | 0.2 | -0.3 | -0.3 | -0.3 | -0.3 | 0.53 | 0.19 |
| 56 | 0 | 0 | 0.51 | 0.19 | 0.1 | 0.1 | -0.2 | 0.3 | 0.2 | 0.2 | 0.3 | 0.2 | 0.3 | 0.4 | -0.3 | 0.2 | 0.3 | 0.4 | 0.5 | 0.36 |
| 57 | 0.06 | 0 | 1.15 | 0.2 | 0.1 | 0.1 | 0.2 | 0.3 | 0.3 | 0.3 | 0.2 | 0.2 | 0.4 | 0.4 | -0.3 | 0.3 | 0.3 | 0.2 | 0.29 | 0.42 |
| 58 | 0.12 | 0.21 | 1.16 | 0.54 | 0.1 | 0.02 | -0.1 | 0.3 | -0.2 | 0.3 | 0.2 | 0.2 | 0.3 | 0.3 | -0.2 | -0.2 | -0.1 | -0.2 | 0.63 | 0.39 |
| 59 | 0.05 | 0.04 | 0.35 | 0.52 | 0.06 | -0.1 | -0.2 | -0.2 | -0.3 | -0.3 | -0.1 | -0.1 | -0.1 | -0.3 | -0.3 | -0.3 | -0.3 | -0.2 | 0.42 | 0.27 |
| 60 | -120 | 126 | -167 | -150 | -194 | -182 | -113 | -115 | -120 | -122 | -123 | -123 | -120 | -120 | -119 | -119 | -113 | -112 | -220 | -224 |

| 0.04 | -0.2 | -0.3 | -0.3 | -0.1 | -0.2 | -0.1 | -0.4 | -0.4 | -0.2 | 0.14 | 1.81 | 1.15 | 0.32 | 0.44 | 0.47 | 0.02 | 0.49 | 0.41 |
|---|---|---|---|---|---|---|---|---|---|---|---|---|---|---|---|---|---|---|
| -0.2 | -0.4 | -0.5 | -0.4 | -0.3 | -0.3 | -0.4 | -0.5 | -0.6 | -0.4 | -0.1 | 1.41 | 0.72 | 0.19 | 0.08 | 0.26 | 0.27 | 0.21 | 0.15 |
| -0.2 | -0.2 | -0.3 | -0.3 | -0.2 | -0.2 | -0.2 | -0.3 | -0.3 | -0.1 | 0.2 | 1.36 | 1.1 | 0.3 | 0.37 | 0.4 | 0.14 | 0.39 | 0.34 |
| -0 | -0.2 | -0.3 | -0.2 | -0.2 | -0.2 | -0.2 | -0.3 | -0.2 | -0.2 | 0 | 0.86 | 0.4 | 0.35 | 0.28 | 0.29 | 0.48 | 0.22 | 0.22 |
| -0.1 | 0.3 | 0.3 | -0.2 | -0.2 | 0.1 | 0.2 | 0.3 | -0.4 | -0.2 | 0.1 | 0.89 | 1 | 0.37 | 0.39 | 0.46 | 0.29 | 0.35 | 0.27 |
| 0.1 | 0.2 | 0.3 | -0.3 | -0.2 | -0.2 | 0.2 | -0.3 | 0.3 | 0.1 | 0.04 | 0.73 | 0.67 | 0.53 | 0.39 | 0.38 | 0.24 | 0.27 | 0.09 |
| -0.1 | -0.1 | -0.3 | -0.2 | -0.2 | -0.2 | 0.2 | -0.3 | -0.3 | -0.1 | -0.1 | 0.67 | 0.83 | 0.45 | 0.42 | 0.38 | 0.39 | 0.34 | 0.06 |
| -0.3 | -0.3 | -0.3 | -0.3 | -0.2 | -0.2 | -0.2 | -0.3 | -0.3 | -0.1 | 0.12 | 0.16 | 0.69 | 0.53 | 0.42 | 0.48 | 0.23 | 0.33 | 0.33 |
| 0.1 | 0.2 | 0.3 | 0.4 | -0.2 | -0.2 | 0.3 | 0.2 | 0.3 | 0.1 | 0.05 | 0.62 | 0.66 | 0.62 | 0.51 | 0.29 | 0.27 | 0.31 | 0.12 |
| -0.3 | -0.1 | 0.2 | 0.2 | -0.2 | -0.2 | -0.2 | -0.3 | -0.3 | 0 | 0.03 | 0.49 | 0.94 | 0.66 | 0.7 | 0.43 | 0.22 | 0.31 | 0.34 |
| 0.1 | 0.2 | 0.3 | 0.3 | -0.2 | -0.2 | 0.3 | 0.2 | 0.2 | 0.1 | 0.16 | 0.26 | 0.71 | 0.54 | 0.45 | 0.27 | 0.42 | 0.03 | 0.11 |
| -0.2 | 0.2 | 0.3 | -0.2 | -0.3 | -0.3 | -0.2 | -0.3 | -0.3 | -0.1 | 0.05 | 0.38 | 0.72 | 0.6 | 0.49 | 0.37 | 0.2 | 0.31 | 0.24 |
| -0.1 | -0.1 | -0.2 | -0.2 | -0.2 | -0.2 | -0.3 | -0.4 | -0.2 | -0.1 | 0.05 | 0.31 | 0.96 | 0.5 | 0.19 | 0.43 | 0.32 | 0.27 | 0.11 |
| -0.1 | -0.2 | -0.3 | -0.2 | -0.3 | -0.3 | -0.2 | -0.3 | -0.3 | 0.05 | 0.17 | 0.56 | 0.75 | 0.49 | 0.5 | 0.38 | 0.3 | 0.27 | 0.28 |
| -0.2 | 0.2 | -0.2 | -0.2 | -0.3 | -0.2 | -0.2 | 0.3 | 0.3 | 0 | 0.31 | 0.15 | 0.31 | 0.58 | 0.5 | 0.17 | 0.36 | 0.25 | 0.16 |
| -0.1 | -0.2 | -0.3 | -0.2 | -0.2 | -0.3 | -0.3 | 0.3 | 0.3 | -0.1 | 0.28 | 0.13 | 0.31 | 0.6 | 0.48 | 0.24 | 0.25 | 0.16 | 0.16 |
| 0.1 | -0.1 | -0.4 | -0.2 | -0.3 | 0.2 | 0.2 | 0.3 | 0.3 | 0 | 0.46 | 0.3 | 0.68 | 0.54 | 0.59 | 0.27 | 0.32 | 0.2 | 0.11 |
| 0 | -0.1 | -0.2 | -0.2 | -0.2 | -0.2 | -0.2 | -0.2 | -0.2 | 0.03 | 0.65 | 0.27 | 0.76 | 0.57 | 0.48 | 0.35 | 0.31 | 0.25 | 0.35 |
| -0.2 | -0.2 | -0.4 | -0.2 | -0.2 | -0.2 | -0.3 | -0.2 | -0.4 | 0.02 | 0.63 | 0.39 | 0.58 | 0.46 | 0.53 | 0.38 | 0.34 | 0.29 | 0.15 |
| -138 | -117 | -116 | -117 | -122 | -122 | -121 | -116 | -115 | -121 | -152 | -219 | -203 | -131 | -133 | -140 | -132 | -147 | -144 |

FIG. 18I

|    | A1    | A2    | A3   | A4   | A5   | A6   | A7   | A8    | A9    | A10  |
|----|-------|-------|------|------|------|------|------|-------|-------|------|
| 1  | -13   | -12   | -8.8 | -8.8 | -3.8 | -8.6 | -7.1 | -11   | -15   | -6.8 |
| 2  | 0.51  | 1.51  | 1.12 | 1.05 | 1.23 | 1.39 | 1.1  | 1.43  | 0.22  | -4.5 |
| 3  | 1.46  | 1.29  | 1.1  | 1.15 | 1.15 | 1.25 | 1.45 | 1.37  | 0.61  | -0.9 |
| 4  | 1.22  | 1.62  | 0.81 | 0.53 | 0.86 | 0.67 | 1.14 | 1.02  | 0.26  | 0.03 |
| 5  | 0.55  | 0.26  | 0.25 | 0.3  | 0.49 | 0.19 | 0.56 | 0.71  | 0.12  | 0.15 |
| 6  | 0.61  | 0.54  | 0.23 | 0.32 | 0.07 | 0.21 | 0.3  | 0.2   | 0.1   | 0.87 |
| 7  | 0.32  | 0.27  | -0   | 0.07 | 0.05 | -0.1 | 0.15 | 0.11  | -0.2  | -0.1 |
| 8  | 0.25  | 0.06  | 0.1  | 0.1  | 0.2  | 0.1  | 0.15 | 0.02  | 0.5   | -0.3 |
| 9  | 0     | 0.1   | 0.2  | 0.3  | 0.2  | -0.2 | 0.3  | 0     | 0.3   | 0.5  |
| 10 | -0.1  | -0.1  | -0.2 | -0.4 | -0.2 | -0.2 | -0.1 | -0.1  | -0.4  | -0.1 |
| 11 | 0.2   | 0.1   | 0.2  | 0.5  | 0.4  | 0.4  | 0.1  | -0.3  | -0.3  | -0.4 |
| 12 | 0.2   | -0.3  | 0.3  | -0.3 | -0.3 | -0.2 | -0.3 | -0.1  | -0.4  | -0.4 |
| 13 | -0.6  | 0.6   | 0.3  | 0.4  | 0.4  | 0.4  | -0.3 | 0.4   | 0.6   | -0.4 |
| 14 | -0.7  | -0.7  | -0.5 | -0.4 | -0.2 | -0.2 | -0.5 | -0.6  | -0.7  | -1.4 |
| 15 | 0.7   | 0.8   | 0.4  | 0.4  | -0.3 | -0.3 | 0.7  | 0.7   | 0.7   | 0.9  |
| 16 | 0.6   | 0.8   | 0.8  | -0.5 | -0.4 | 0.3  | 0.7  | 0.7   | -0.7  | -0.7 |
| 17 | 0.5   | 0.7   | 0.7  | 0.5  | 0.3  | 0.4  | -0.6 | 0.4   | -0.5  | 0.5  |
| 18 | -0.4  | 0.2   | 0.9  | -0.6 | 0.4  | -0.3 | -0.5 | 0.6   | -0.5  | -0.5 |
| 19 | 0.69  | 3.1   | 0.9  | 0.7  | 0.5  | 0.5  | 0.6  | 0.7   | 0.5   | 0.5  |
| 20 | 6.49  | 7.98  | -0.9 | 0.9  | -0.5 | 0.5  | -0.8 | -1.3  | -1.4  | -0.7 |
| 21 | 2.34  | 2.58  | 1    | 0.7  | 0.5  | 0.3  | 1.5  | 0.1   | 2.8   | 1.4  |
| 22 | 1.64  | 1.3   | 1.3  | 0.9  | 0.4  | 0.5  | 1.3  | 2.11  | 2.3   | 2    |
| 23 | 3.23  | 2.65  | -1.5 | -1.2 | -0.5 | -0.5 | -0.4 | 1.48  | -1.2  | -1.0 |
| 24 | 3.23  | 2.77  | 1.6  | 1.3  | -0.4 | 0.6  | 0.07 | 1.73  | 0.33  | 1.3  |
| 25 | 2.98  | 2.85  | -1.8 | -1.3 | -0.5 | -0.4 | -0.2 | 3.09  | 2.32  | -0.9 |
| 26 | 2.57  | 2.73  | 1.7  | -1.6 | -0.5 | 0.7  | 0.32 | 3.76  | 2.44  | -0.1 |
| 27 | 2.3   | 1.61  | 0.59 | -1.6 | -0.6 | -0.6 | 0.69 | 3.75  | 1.52  | 0.33 |
| 28 | 2.03  | 2.23  | 4.35 | 2.88 | -0.7 | -0.7 | 1.32 | 4.53  | 1.14  | 0.44 |
| 29 | 1.8   | 1.25  | 4.16 | 5.84 | -0.6 | -0.7 | 1.45 | 3.45  | 1.8   | 0.45 |
| 30 | 2.22  | 1.6   | 4.07 | 4.67 | 0.8  | 0.8  | 2.18 | 3.34  | 1.18  | 0.46 |

FIG. 19A

| A11 | A12 | A13 | A14 | A15 | A16 | A17 | A18 | A19 |
|---|---|---|---|---|---|---|---|---|
| -3.6 | -4.8 | -4.6 | -2.3 | -19 | -19 | -0.7 | -1.2 | -2 |
| 1.29 | 0.84 | -0.1 | 2.7 | -1.8 | -1.5 | 3.1 | -0.4 | 0.68 |
| 0.39 | 0.46 | -1.4 | -0.1 | 0.5 | -0.8 | -0.2 | 0.34 | 0.43 |
| 0.66 | 1.3 | 0.4 | 0.47 | -0.3 | 0.5 | 0.11 | 0.27 | 0.28 |
| 0.49 | 1.15 | -0.1 | 0.32 | -0.2 | -0.5 | 0.04 | -0.1 | 0.14 |
| 0.4 | 0.57 | 0.34 | 0.63 | 0.3 | 0.3 | 0.11 | 0.08 | 0.02 |
| -0.1 | 0.45 | 0.45 | 0.66 | -0.3 | -0.4 | -0.1 | -0.2 | -0 |
| 0 | 0.33 | 0.4 | 0.5 | 0.3 | 0.5 | 0.1 | -0.2 | 0.2 |
| 0.1 | -0.1 | 0.49 | 0.24 | 0.4 | 0.5 | -0.4 | 0.4 | -0.3 |
| 0.02 | -0 | 0.14 | 0.1 | -0.5 | -0.5 | -0.4 | -0.4 | -0.3 |
| 0.2 | 0.2 | 0.06 | -0.1 | -0.5 | 0.5 | 0.4 | 0.5 | 0.5 |
| -0.1 | -0.2 | -0.1 | -0.1 | -0.5 | -0.5 | -0.5 | -0.5 | -0.4 |
| -0 | -0.1 | 0.1 | -0.3 | 0.5 | -0.5 | -0.4 | 0.4 | -0.5 |
| -0.2 | -0.1 | 0.08 | -0.2 | -0.4 | -0.4 | -0.4 | -0.4 | -0.5 |
| 0.2 | 0.3 | -0.2 | 0.4 | 0.5 | -0.6 | -0.4 | 0.5 | 0.8 |
| -0.1 | -0.1 | -0.6 | -0.6 | 0.6 | -0.6 | -0.4 | -0.4 | -0.8 |
| 0.3 | 0.1 | -0.6 | 0.6 | 0.6 | -0.5 | 0.3 | 0.4 | -0.6 |
| 0.3 | -0.3 | 0.6 | 0.5 | -0.5 | -0.4 | -0.5 | -0.4 | -0.8 |
| 0.2 | 0.3 | 0.6 | 0.5 | 0.5 | 0.5 | 0.4 | 0.5 | 0.6 |
| 0.3 | -0.4 | -0.5 | -0.6 | 0.5 | -0.3 | -0.5 | -0.5 | -0.8 |
| 0.3 | 0.3 | -0.5 | -0.5 | 0.4 | 0.4 | -0.5 | 0.6 | 0.9 |
| 0.5 | 0.5 | 0.4 | 0.4 | -0.4 | -0.3 | 0.5 | -0.4 | -1.3 |
| -0.4 | -0.3 | 0.01 | -0.2 | -0.4 | -0.4 | -0.6 | -0.5 | -1.4 |
| 0.5 | -0.4 | 0.52 | 0.61 | 0.3 | -0.4 | -0.6 | -0.7 | 1.2 |
| -0.6 | -0.6 | 2.16 | 2.82 | -0.1 | -0.7 | -0.7 | -0.7 | -1.1 |
| -0.7 | -0.6 | 3.94 | 5.5 | 1.35 | 0.14 | -0.8 | -0.6 | -1 |
| -0.7 | -0.7 | 2.49 | 2.24 | 2.67 | 2.16 | -0.7 | -0.8 | 0.06 |
| -0.6 | -0.6 | 0.89 | 0.34 | 3.08 | 2.76 | -0.7 | -0.7 | 4.07 |
| -0.7 | -0.7 | 2.87 | 1.67 | 4.33 | 3.84 | -0.8 | -0.8 | 5.87 |
| -0.5 | -0.7 | 3.09 | 2.93 | 6.43 | 4.58 | -0.9 | -0.8 | 5.19 |

FIG. 19B

| A20 | A21 | A22 | A23 | A24 | A25 | A26 | A27 | A28 | A29 | A30 |
|---|---|---|---|---|---|---|---|---|---|---|
| -2.7 | -0.4 | -0.4 | 1.08 | 6.47 | 6.49 | 8.4 | 0.57 | 1.41 | 1.94 | 2.58 |
| 0.47 | -1.3 | 0.25 | -0.8 | -1.3 | -3.6 | -4.3 | 2.69 | -1 | 1.9 | -0.7 |
| 0.75 | 0.35 | 0.36 | 0.1 | -0.1 | -0.9 | -0.8 | -2.9 | -0.6 | -0.4 | -1.8 |
| 0.47 | 0.56 | 0.29 | 0.31 | 0.22 | -0.3 | -0.2 | -0.9 | -0.4 | -0.5 | 0.9 |
| 0.07 | 0.09 | 0.03 | 0.09 | 0.08 | 0.01 | 0.02 | -0.5 | -0.4 | -0.2 | -0.5 |
| 0.15 | 0.24 | 0.11 | 0.13 | 0.16 | 0.21 | 0.01 | 0.4 | 0.3 | 0.2 | 0.2 |
| -0.1 | -0.1 | 0.04 | -0.1 | 0.15 | 0.22 | -0 | -0.3 | -0.2 | -0.2 | -0.3 |
| -0.3 | -0.3 | -0.1 | -0.2 | -0.2 | 0.2 | -0 | 0.2 | 0.3 | 0.3 | 0.1 |
| 0.2 | -0.2 | -0.4 | -0.4 | -0.2 | 0 | 0.02 | -0.3 | -0.1 | -0.1 | -0.2 |
| -0.4 | -0.3 | -0.3 | -0.2 | -0.1 | -0 | -0.1 | -0.3 | -0.4 | -0.5 | -0.2 |
| -0.5 | -0.5 | -0.5 | -0.3 | -0.2 | -0.1 | 0.1 | -0.4 | -0.4 | 0.5 | 0.37 |
| -0.4 | -0.6 | -0.5 | -0.3 | -0.2 | -0.3 | -0.4 | -0.4 | -0.5 | -0.4 | -0.4 |
| -0.5 | -0.8 | -0.7 | -0.4 | -0.2 | -0.3 | -0.3 | -0.3 | -0.4 | -0.4 | 0.5 |
| -0.6 | -1 | -0.8 | -0.3 | -0.1 | -0.3 | -0.5 | -0.4 | -0.6 | -0.6 | -0.5 |
| -0.8 | -0.9 | -0.9 | -0.3 | -0.3 | -0.6 | -0.5 | -0.6 | -0.5 | -0.6 | -0.7 |
| -0.6 | -0.7 | -0.8 | -0.6 | -0.6 | -0.7 | -0.6 | -0.7 | -0.5 | -0.6 | -0.5 |
| -0.5 | -0.5 | -0.7 | -0.9 | -0.7 | -0.7 | -0.7 | -0.6 | -0.6 | -0.6 | -0.4 |
| -0.6 | -0.7 | -0.7 | -0.9 | -0.9 | -0.5 | -0.6 | -0.6 | -0.9 | -0.6 | -0.6 |
| 0.5 | -0.8 | -0.8 | 0.7 | 0.9 | -0.7 | -0.5 | -0.3 | 0.7 | 0.5 | 0.5 |
| -0.9 | 1.36 | -0.8 | -0.8 | -0.8 | -0.7 | -0.5 | -0.3 | -0.4 | -0.4 | -0.6 |
| 1.4 | 1.44 | 1.03 | 0.7 | -0.7 | -0.4 | -0.4 | -0.2 | 0.1 | 0.4 | 0.5 |
| 1 | 1.12 | 0.32 | -1.1 | -0.8 | 0.3 | 0.5 | -0.6 | -0.2 | -0.6 | -0.9 |
| -0.1 | 1.9 | 0.82 | -0.8 | -1 | 1.07 | -0.1 | -0.5 | -0.5 | -0.7 | -1.2 |
| -0.1 | 1.4 | 1.13 | -0.5 | 0.1 | 2.69 | 1.53 | -0.9 | -0.6 | -0.9 | -1.2 |
| -0.1 | 1.57 | 1.72 | -0.9 | 0.15 | 1.51 | 2.09 | -1.5 | -0.9 | -0.9 | -0.9 |
| 1.06 | 1.53 | 1.67 | 2.61 | 1.45 | 1.49 | 2.43 | -1.7 | -1.5 | -1.1 | -0.3 |
| 3.9 | 2.46 | 1.74 | 4.09 | 4.13 | 2.56 | 2.9 | 2.49 | -1.3 | -0.8 | 5.38 |
| 3.68 | 2.32 | 1.11 | 4.39 | 4.42 | 2.38 | 3.95 | 8.05 | 1.82 | -0.5 | 10.5 |
| 3.99 | 1.86 | 1.32 | 3.25 | 3.63 | 2.19 | 2.75 | 8.33 | 8.82 | -0 | 9.62 |
| 4.44 | 1.62 | 2.03 | 2.62 | 2.87 | 2.79 | 2.63 | 6.71 | 9.57 | 5.24 | 7.9 |

FIG. 19C

| A31 | A32 | A33 | A34 | A35 | A36 | A37 | A38 | A39 | A40 |
|---|---|---|---|---|---|---|---|---|---|
| 1.71 | -1.1 | -0.9 | -3.8 | 7.1 | -2.1 | 0.28 | 0.62 | -0.5 | 1.03 |
| -3.4 | 0.14 | -0.4 | -3.7 | 3.51 | -2.7 | -0.4 | -0.6 | -1 | -1.3 |
| -1.4 | -1.3 | -2.6 | -2.4 | -0.8 | -3.3 | -0.8 | -1.1 | -0.8 | 1.13 |
| -0.9 | -0.3 | -2.1 | -1.5 | -0.7 | -1.8 | -0.3 | -0.6 | -0.6 | -0.9 |
| -0.4 | 0.3 | -1.6 | -0.9 | -1.2 | 1 | -0 | -0.3 | -0.2 | -0.8 |
| 0.1 | 0.1 | 1.2 | -0.5 | 1 | 0.6 | 0.08 | 0.3 | 0.3 | 0.5 |
| -0.1 | -0.2 | -1 | -0.2 | -0.9 | -0.5 | -0.1 | -0.2 | -0 | -0.3 |
| -0.1 | 0 | -0.7 | -0.4 | 0.9 | -0.2 | 0.2 | 0.06 | 0.1 | 0.3 |
| 0.2 | -0.1 | -0.8 | -0.3 | 0.8 | 0.5 | 0.1 | 0.03 | -0.1 | 0.4 |
| -0.2 | -0.2 | -0.8 | -0.3 | -0.8 | -0.5 | -0.1 | -0.1 | -0.1 | -0.2 |
| 0.4 | -0.4 | -0.7 | -0.4 | -0.7 | -0.4 | 0.03 | -0.2 | -0.1 | 0.1 |
| -0.5 | -0.3 | -0.8 | -0.5 | -0.9 | -0.5 | -0.1 | 0 | -0.2 | -0.2 |
| -0.7 | -0.6 | -0.7 | -0.5 | -0.7 | -0.4 | 0.09 | -0 | -0.2 | -0.3 |
| -0.8 | -0.8 | -0.8 | -0.6 | -0.8 | -0.5 | -0.2 | -0.2 | -0.3 | -0.6 |
| -0.9 | -0.8 | -0.8 | -0.7 | -0.7 | -0.4 | 0.3 | 0.3 | 1.09 | 0.5 |
| -0.8 | -0.7 | -0.9 | -0.8 | -0.6 | -0.6 | 0.3 | -0.3 | -0.9 | -0.7 |
| -0.7 | -0.8 | -0.9 | 0.8 | -0.6 | -0.4 | -0.4 | -0.4 | -0.9 | -0.7 |
| -0.6 | -0.6 | -0.9 | -0.8 | -0.8 | -0.5 | -0.3 | -0.4 | -0.6 | 0.6 |
| 0.9 | 1 | -0.7 | 0.7 | -0.9 | 0.6 | -0.6 | 0.6 | 0.8 | 0.4 |
| 0.38 | -0.1 | -0.8 | -0.6 | -0.9 | -0.6 | -0.6 | -0.5 | -0.6 | -0.4 |
| 1.84 | 1.51 | 1.3 | 2 | -0.7 | 0.6 | 0.7 | -0.6 | -0.5 | -0.2 |
| 2.01 | 1.39 | 0.14 | -1.4 | -0.8 | 0.6 | -0.5 | -0.7 | -0.5 | -0.1 |
| 2.73 | 1.07 | 0.02 | -0.1 | -0.8 | -0.5 | -0.5 | -0.5 | -0.8 | 0.52 |
| 2.11 | 1.28 | 2.07 | 1.74 | -0.7 | -0.6 | -0.4 | -0.6 | 0.36 | 3.55 |
| 2.22 | 2.49 | 3.96 | 3.02 | -0.7 | -0.5 | -0.5 | -0.5 | 2.68 | 2.15 |
| 2.37 | 3.41 | 5.43 | 4.91 | -0.8 | -0.6 | -0.4 | -0.4 | 1.41 | 1.77 |
| 2.33 | 2.71 | 5.26 | 4.8 | -0.7 | -0.7 | -0.3 | -0.5 | 1.37 | 2.75 |
| 2.65 | 3.19 | 4.93 | 3.47 | -0.7 | -0.6 | -0.4 | -0.4 | 3.35 | 3.35 |
| 2.84 | 3.53 | 3.11 | 2.24 | -0.6 | -0.5 | -0.1 | 0.08 | 3.28 | 3.19 |
| 3.17 | 3.98 | 2 | 2.33 | -0.3 | -0.3 | 0.43 | 1.07 | 4.04 | 3.99 |

FIG. 19D

| A41 | A42 | A43 | A44 | A45 | A46 | A47 | A48 | A49 | A50 | A51 |
|---|---|---|---|---|---|---|---|---|---|---|
| 0.07 | 0.49 | 1.02 | 8.44 | 7.48 | 8.31 | 6.82 | 5.89 | 1.96 | 1.52 | 2.61 |
| -0.9 | -1 | -0.8 | -3.3 | -2.3 | -3 | -1.4 | -1.5 | 0.37 | 0.36 | -0.4 |
| -0.1 | -0.6 | -0.8 | -1.3 | -0.5 | -0.5 | 0.43 | -0.6 | -0.7 | -0.1 | -0.4 |
| -0.7 | -0.6 | -0.6 | -0.5 | -0.4 | 0.02 | 0.15 | -0 | -0.2 | -0.3 | -0.3 |
| -0.5 | -0.3 | -0.4 | -0.5 | -0.3 | -0 | -0 | -0.1 | -0.1 | 0.01 | -0.3 |
| 0.3 | 0 | -0.3 | 0.2 | 0.2 | 0.16 | 0.05 | 0.09 | -0 | 0.01 | 0.1 |
| -0.3 | -0.1 | -0.2 | -0.3 | -0.1 | 0.21 | 0.2 | 0.26 | 0.03 | -0.4 | -0.2 |
| -0.1 | 0.2 | -0.3 | 0.2 | -0.1 | 0.19 | 0.13 | 0 | 0.2 | 0.2 | 0.3 |
| 0.3 | 0.2 | -0.1 | 0.08 | -0.1 | 0.09 | -0.1 | 0.2 | 0.4 | 0.2 | 0.5 |
| -0 | -0.2 | -0 | 0.04 | -0.3 | 0.07 | 0.06 | -0.1 | -0.3 | -0.5 | -0.4 |
| -0.1 | -0.2 | 0.01 | -0.1 | -0.2 | 0 | 0.2 | -0.2 | 0.4 | -0.5 | -0.6 |
| -0.1 | -0.2 | -0.2 | -0.1 | -0.1 | -0.3 | -0.1 | -0.2 | -0.6 | -0.5 | -0.6 |
| -0.3 | -0.1 | -0.1 | -0.3 | -0.2 | -0.1 | -0.2 | -0.2 | -0.5 | -0.5 | -0.6 |
| -0.5 | -0.3 | -0.2 | -0.3 | -0.3 | -0.2 | -0.2 | -0.1 | -0.4 | -0.4 | -0.4 |
| -0.7 | -0.5 | 0.3 | -0.3 | -0.2 | -0.2 | -0.2 | -0.2 | -0.4 | 0.4 | -0.5 |
| -0.5 | -0.7 | -0.3 | -0.4 | -0.4 | -0.3 | -0.3 | -0.4 | -0.5 | -0.5 | -0.4 |
| 0.4 | -0.7 | -0.3 | -0.3 | -0.3 | -0.2 | -0.2 | -0.3 | 0.5 | -0.5 | 0.5 |
| -0.2 | -0.5 | -0.2 | -0.3 | -0.2 | -0.4 | -0.4 | -0.4 | -0.3 | -0.5 | -0.3 |
| 0.5 | -0.5 | 0.3 | -0.2 | 0.2 | 0.3 | -0.5 | -0.3 | 0.4 | 0.5 | 0.5 |
| -0.4 | -0.2 | -0.3 | -0.4 | -0.2 | -0.2 | -0.4 | -0.5 | -0.4 | -0.5 | -0.4 |
| -0.4 | 0.2 | 0.2 | -0.4 | 0.3 | -0.2 | -0.5 | 0.4 | 0.5 | 0.4 | 0.6 |
| -0.5 | -0.3 | 0.4 | -0.4 | -0.2 | -0.3 | -0.5 | -0.6 | -0.4 | -0.5 | -0.7 |
| -0.7 | -0.5 | -0.4 | -0.4 | -0.3 | -0.4 | -0.4 | -0.4 | -0.4 | -0.4 | -0.7 |
| -0.1 | 1 | -0.4 | 0.3 | -0.3 | 0.3 | 0.4 | 0.5 | -0.3 | -0.3 | -0.7 |
| 0.96 | -1 | -0.5 | -0.3 | -0.3 | -0.4 | -0.4 | -0.4 | -0.4 | -0.4 | -0.7 |
| 1 | -0.4 | -0.4 | -0.5 | -0.4 | -0.5 | -0.1 | -0.5 | -0.4 | -0.4 | -0.7 |
| 2.4 | 0.37 | -0.5 | -0.5 | -0.5 | -0.4 | -0.1 | -0.5 | -0.4 | -0.3 | -0.7 |
| 4.05 | 2.93 | -0.6 | -0.5 | -0.4 | -0.5 | -0.3 | -0.3 | -0.2 | -0.3 | -0.6 |
| 4.75 | 5.05 | -0.6 | -0.5 | -0.5 | -0.5 | -0.4 | -0.4 | 0.14 | 0.04 | -0.5 |
| 4.78 | 4.8 | -0.5 | -0.4 | -0.5 | -0.5 | -0.4 | -0.4 | 0.42 | 0.48 | 0.5 |

FIG. 19E

Primer mix fixed position

| A52 | A53 | A54 | A56 | A57 | A58 | A59 | A60 |
|---|---|---|---|---|---|---|---|
| -0 | -0.1 | 0.14 | 0.51 | 2.37 | 3.23 | 9.53 | 10.8 |
| 0.66 | 0.23 | 0.32 | 0.6 | -2.5 | -1.8 | 0.38 | 1.09 |
| 0.01 | 0.04 | 0.2 | -0.3 | -1.5 | -1.8 | -0.4 | -0.6 |
| -0 | -0.1 | -0.1 | 0.02 | -1.3 | -1.5 | 0.6 | 0.7 |
| -0.1 | -0.2 | 0.21 | 0.01 | -0.8 | 1 | 0.7 | -0.6 |
| 0 | 0.1 | 0.1 | 0.2 | 0.6 | 0.5 | 0.4 | 0.9 |
| -0.2 | -0.1 | -0 | -0.1 | -0.6 | -0.4 | -0.4 | -0.7 |
| 0.3 | -0.2 | -0.2 | 0.2 | -0.5 | 0.5 | 0.2 | 0.6 |
| -0.3 | -0.2 | 0.4 | 1.23 | 0.6 | 0.5 | 0.5 | 0.5 |
| -0.5 | -0.4 | -0.5 | -0.4 | -0.6 | -0.4 | -0.3 | -0.7 |
| -0.5 | -0.5 | -0.5 | 0.4 | -0.6 | 0.5 | -0.4 | -0.5 |
| -0.5 | -0.5 | -0.5 | -0.7 | -0.5 | -0.6 | -0.4 | -0.5 |
| -0.5 | -0.6 | -0.5 | -0.6 | 0.6 | -0.5 | -0.2 | -0.4 |
| -0.4 | -0.4 | -0.5 | -0.6 | -0.4 | -0.6 | -0.5 | -0.4 |
| 0.4 | 0.4 | -0.6 | 0.6 | -0.5 | 0.3 | -0.2 | -0.3 |
| -0.4 | -0.6 | -0.5 | -0.8 | -0.4 | -0.4 | -0.4 | 0.3 |
| -0.4 | -0.4 | -0.5 | -0.7 | 0.4 | -0.5 | -0.3 | 0.3 |
| -0.4 | -0.5 | -0.6 | -0.8 | -0.5 | 0.4 | -0.4 | -0.3 |
| 0.5 | 0.6 | 0.7 | 0.6 | 0.5 | 0.6 | 0.3 | 0.2 |
| -0.4 | -0.6 | -0.6 | 0.6 | -0.6 | -0.5 | -0.5 | -0.4 |
| 0.5 | -0.5 | -0.6 | -0.5 | 0.7 | 0.5 | 0.3 | 0.2 |
| -0.6 | 1.03 | 0.6 | -0.4 | 0.5 | 0.5 | -0.3 | 0.3 |
| -0.6 | -0.5 | -0.5 | -0.5 | -0.6 | -0.5 | -0.4 | -0.3 |
| -0.7 | 0.1 | 0.6 | -0.8 | -0.5 | -0.4 | -0.3 | -0.2 |
| -0.8 | -0.5 | -0.5 | -0 | -0.5 | -0.5 | -0.4 | -0.3 |
| -0.8 | -0.5 | -0.5 | -0.75 | -0.4 | -0.5 | -0.2 | -0.3 |
| -0.6 | -0.6 | -0.5 | 2.28 | -0.3 | -0.4 | -0.4 | -0.4 |
| -0.7 | -0.7 | -0.4 | 2.6 | -0.3 | -0.4 | 0.3 | 0.3 |
| -0.6 | -0.7 | -0.4 | 2.12 | -0.5 | -0.4 | -0.3 | -0.3 |
| -0.5 | 0.5 | 0.1 | 2.06 | -0.4 | -0.4 | 0.3 | -0.4 |

FIG. 19F

| | | | | | | | | | |
|---|---|---|---|---|---|---|---|---|---|
| 31 | 2.31 | 1.91 | 4.05 | 4.32 | 0.8 | 0.7 | 2.84 | 3.43 | 1.4 | 0.42 |
| 32 | 1.31 | 2.33 | 4.31 | 3.96 | 0.7 | 0.8 | 3.89 | 3.96 | 1.25 | 0.27 |
| 33 | 1.57 | 1.81 | 3.9 | 3.74 | 0.8 | 0.8 | 4.17 | 3.88 | 0.52 | 0.13 |
| 34 | 1.3 | 1.46 | 3.21 | 4.06 | 0.8 | 0.8 | 5.1 | 3.84 | 0.88 | 0.03 |
| 35 | 1.53 | 1.48 | 3.96 | 3.2 | 0.8 | 0.8 | 4.47 | 3.63 | 0.5 | 0.03 |
| 36 | 2.01 | 1.4 | 3.43 | 3.51 | -0.8 | -0.9 | 4.49 | 3.74 | 0.21 | 0.23 |
| 37 | 1.46 | 0.98 | 2.87 | 2.66 | 0.8 | 0.7 | 3.47 | 3.14 | 0.28 | 0.08 |
| 38 | 1.35 | 0.77 | 3.63 | 2.96 | -0.9 | -0.8 | 3.36 | 2.76 | -0.2 | -0.1 |
| 39 | 0.81 | 0.49 | 3.64 | 3.11 | 0.92 | -0.9 | 2.78 | 2.52 | 0.08 | -0.1 |
| 40 | 1 | 0.26 | 3.77 | 3.24 | 3.26 | 0.07 | 2.33 | 2.45 | 013 | -0.1 |
| 41 | 1.84 | 0.53 | 3.42 | 3.93 | 4.25 | 2.76 | 2.98 | 2.44 | 0.4 | 0.21 |
| 42 | 1.03 | 0.88 | 3.93 | 3.83 | 2.99 | 3.66 | 2.45 | 2.49 | 0.31 | -0.2 |
| 43 | 1.33 | 0.99 | 2.66 | 3.76 | 1.9 | 2.95 | 2.55 | 1.89 | 0.23 | 0.1 |
| 44 | 1.42 | 1.28 | 3.52 | 3.85 | 2.07 | 1.87 | 2.44 | 2.35 | 0.13 | 0.05 |
| 45 | 1.36 | 1.61 | 2.26 | 3.96 | 2.05 | 1.72 | 2.59 | 1.69 | 0.1 | 0.05 |
| 46 | 0.98 | 0.92 | 5.19 | 1.91 | 2.23 | 1.5 | 1.9 | 1.48 | 0.03 | -0 |
| 47 | 1.11 | 0.86 | 7.93 | 5.01 | 2.61 | 1.79 | 1.63 | 1.37 | 0.09 | -0.2 |
| 48 | 0.53 | 0.9 | 5.88 | 7.97 | 2.7 | 1.84 | 1.4 | 1.62 | 0 | 0 |
| 49 | 1.12 | 1.08 | 4.5 | 6.07 | 3.07 | 2.52 | 1.47 | 1.29 | 0.12 | 0.2 |
| 50 | 0.85 | 0.91 | 4.28 | 3.36 | 2.93 | 2.47 | 0.93 | 1.44 | 0.07 | 0 |
| 51 | 0.95 | 0.85 | 2.36 | 1.78 | 3.53 | 2.89 | 1.84 | 1.46 | 0.1 | -0 |
| 52 | 0.9 | 0.83 | 2.39 | 0.39 | 3.44 | 2.98 | 1.39 | 1.07 | 0.18 | -0.1 |
| 53 | 1 | 1.04 | 1.57 | 0.08 | 3.18 | 3.5 | 1.42 | 0.75 | 0.24 | 0 |
| 54 | 0.83 | 0.82 | 2.33 | 1.38 | 3.63 | 3.69 | 1.32 | 0.89 | 0.16 | -0.1 |
| 55 | 0.2 | 0.74 | 2.2 | 1.79 | 3.17 | 3.07 | 0.96 | 1.09 | 0.04 | -0.2 |
| 56 | 0.83 | 0.93 | 2.73 | 1.92 | 2.08 | 3.93 | 1.49 | 0.79 | 0.14 | 0.05 |
| 57 | 0.8 | 0.8 | 1.68 | 1.11 | 1.29 | 2.57 | 0.92 | 1.07 | 0.03 | -0.2 |
| 58 | 0.85 | 0.7 | 1.01 | 1.25 | 5.16 | 1.74 | 1.48 | 1.03 | 0.30 | -0 |
| 59 | 0.94 | 0.83 | 0.93 | 0.96 | 9.73 | 2.02 | 1.57 | 1.41 | 0.29 | 0.06 |
| 60 | 224 | 221 | 256 | 248 | 210 | 193 | 229 | 244 | 165 | 149 |

FIG. 19G $$\begin{bmatrix}
-0.6 & 0.8 & 2.44 & 2.22 & 6.39 & 5.45 & -0.9 & -0.8 & 5.11 \\
0.7 & -0.7 & 1.69 & 1.6 & 5.04 & 5.45 & -0.9 & 1 & 5.15 \\
0.5 & -0.7 & 1.35 & 1.25 & 3.74 & 4.45 & 0.38 & -0.9 & 5.04 \\
-0.5 & 0.6 & 1.46 & 0.25 & 3.85 & 4.11 & 2.18 & -0.2 & 4.81 \\
-0.5 & -0.7 & 0.78 & 0.32 & 4.04 & 3.49 & 2.71 & 1.08 & 4.52 \\
-0.6 & -0.5 & 0.38 & -0.1 & 4.45 & 4.35 & 2.49 & 1.91 & 3.98 \\
-0.5 & -0.7 & 0.45 & -0.4 & 4.61 & 4.63 & 2.37 & 1.71 & 3.71 \\
-0.6 & -0.5 & 0.35 & -0.5 & 4.01 & 4.05 & 2.65 & 1.71 & 3.57 \\
-0.5 & -0.5 & 0.08 & -0.4 & 4.47 & 4.46 & 2.72 & 2.17 & 3.2 \\
-0.7 & -0.5 & 0.04 & -0.3 & 3.72 & 3.85 & 3 & 2.23 & 2.73 \\
-0.4 & -0.5 & 0.17 & -0.4 & 3.33 & 4.06 & 3.3 & 2.67 & 2.42 \\
-0.6 & -0.5 & -0 & -0.3 & 3.11 & 3.23 & 2.88 & 2.49 & 2.21 \\
0.4 & 0.5 & 0.06 & 0.3 & 2.75 & 3.07 & 2.57 & 2.3 & 1.71 \\
-0.4 & -0.3 & 0.1 & -0.2 & 2.29 & 3.1 & 3.19 & 2.43 & 1.46 \\
0.2 & 0.4 & 0.15 & -0.2 & 2.01 & 2.3 & 2.4 & 2.69 & 1.73 \\
-0.5 & -0.4 & -0.2 & 0.3 & 1.79 & 1.94 & 2.24 & 2.66 & 1.63 \\
0.3 & 0.2 & 0.1 & 0.02 & 1.27 & 1.98 & 2.64 & 2.1 & 1.41 \\
0.4 & 0.5 & 0.08 & 0.2 & 0.5 & 1.46 & 2.2 & 2.13 & 0.7 \\
-0.4 & 0.3 & 0 & 0.1 & 0.21 & 1.08 & 1.79 & 1.77 & 1.36 \\
-0.4 & -0.4 & -0 & 0.2 & 0.16 & 0.74 & 1.63 & 1.83 & 0.8 \\
-0.4 & -0.2 & 0.13 & -0.2 & 0.59 & 0.69 & 1.49 & 1.72 & 0.83 \\
-0.5 & -0.3 & 0 & -0.1 & 0.28 & 1.21 & 0.98 & 1.46 & 0.98 \\
-0.3 & 0.2 & -0.1 & -0.3 & 0.33 & 0.49 & 1.46 & 1.36 & 0.88 \\
-0.3 & -0.2 & 0.08 & -0 & -0.1 & 0.43 & 1.48 & 1.52 & 0.92 \\
-0.4 & -0.4 & -0.1 & -0.3 & 0.12 & 0.55 & 0.92 & 1.2 & 0.61 \\
0.3 & 0.4 & 0.01 & 0.1 & 0.13 & 0.12 & 1.15 & 1.31 & 0.42 \\
-0.3 & 0.4 & 0.1 & -0.3 & -0 & 0.26 & 0.77 & 0.96 & 0.73 \\
-0.3 & -0.2 & 0 & -0 & 0.01 & 0.44 & 0.92 & 0.78 & 0.56 \\
0.3 & -0.3 & 0 & 0.2 & 0.12 & 0.23 & 1.03 & 0.97 & 0.47 \\
144 & 143 & 187 & 175 & 234 & 236 & 204 & 194 & 229
\end{bmatrix}$$

FIG. 19H

| 4.42 | 1.98 | 1.81 |      | 2.12 | 4    | 3.33 | 6.93 | 7.7  | 9.45 | 6.58 |
|------|------|------|------|------|------|------|------|------|------|------|
| 4.17 | 2.04 | 1.86 | 2.09 | 2.78 | 2.22 | 4.37 | 5.5  | 6.99 | 8.75 | 5.64 |
| 4.18 | 2.02 | 1.77 | 1.7  | 2.51 | 2.11 | 2.75 | 6    | 5.96 | 7.09 | 5.8  |
| 4.4  | 2.02 | 1.69 | 2.17 | 3.31 | 3.61 | 2.99 | 4.9  | 5.71 | 5.97 | 4.73 |
| 4.57 | 1.51 | 1.78 | 2.26 | 2.28 | 2.87 | 2.71 | 4.7  | 4.66 | 6.03 | 3.84 |
| 4.19 | 2.21 | 2.49 | 1.11 | 2.16 | 4.26 | 2.56 | 4.67 | 4.23 | 4.82 | 3.85 |
| 3.98 | 1.88 | 2.08 | 2.12 | 2.42 | 3.32 | 2.78 | 3.63 | 4.73 | 4.89 | 3.63 |
| 3.45 | 1.99 | 2.38 | 1.91 | 2    | 2.78 | 2.98 | 3.85 | 3.61 | 3.9  | 3.21 |
| 3.35 | 2.01 | 2.27 | 1.03 | 1.89 | 2.49 | 2.49 | 3.12 | 3.29 | 3.53 | 3.09 |
| 3.18 | 2.27 | 1.74 | 1.72 | 1.38 | 2.82 | 3.09 | 2.71 | 2.66 | 3.04 | 2.67 |
| 2.76 | 3.09 | 2.21 | 1.7  | 1.31 | 2.44 | 3.19 | 2.51 | 2.26 | 2.87 | 2.31 |
| 2.4  | 2.11 | 2.08 | 2.14 | 1.46 | 1.33 | 2.11 | 2.4  | 2.58 | 2.87 | 2.37 |
| 2.16 | 2.49 | 2.23 | 2.32 | 0.63 | 1.69 | 1.74 | 1.47 | 2.22 | 2.24 | 2.21 |
| 2    | 1.92 | 2.57 | 1.68 | 0.69 | 1.38 | 2.02 | 2.06 | 1.53 | 2.76 | 2.34 |
| 1.93 | 2.39 | 2.37 | 2.06 | 0.66 | 1.77 | 1.5  | 1.29 | 1.74 | 2.21 | 2.06 |
| 1.51 | 1.89 | 1.91 | 1.25 | 0.51 | 0.85 | 1.5  | 1.83 | 1.22 | 1.86 | 1.41 |
| 2.02 | 1.88 | 2.28 | 1.63 | 0.81 | 1.25 | 0.94 | 1.48 | 1.62 | 1.36 | 2.03 |
| 1.16 | 2.27 | 1.71 | 0.79 | 0.08 | 0.23 | 1.37 | 1    | 1.32 | 1.9  | 1.85 |
| 1.48 | 1.74 | 2.14 | 0.69 | 0.12 | 1.01 | 0.53 | 1.46 | 1.1  | 1.19 | 1.57 |
| 1.1  | 2.35 | 2    | 0.63 | -0.1 | 0.85 | 1.22 | 1.02 | 1.33 | 1.71 | 1.68 |
| 1.39 | 1.91 | 1.84 | 0.22 | -0.1 | 1.03 | 1.13 | 0.48 | 1.03 | 1.23 | 1.47 |
| 1.15 | 2.03 | 2.01 | 0.32 | 0.05 | 0.08 | 1.02 | 1.54 | 0.97 | 1.53 | 1.43 |
| 1.37 | 2.11 | 2.35 | 0.04 | -0.1 | 0.56 | 0.59 | 0.93 | 0.84 | 1.58 | 0.98 |
| 0.65 | 2.31 | 2.13 | -0.3 | -0.1 | 1.16 | 1.22 | 0.86 | 1.03 | 1.17 | 1.49 |
| 1.04 | 1.77 | 1.41 | -0.1 | -0.3 | 1.06 | 0.78 | 0.49 | 0.48 | 1.08 | 1.11 |
| 0.85 | 1.75 | 1.76 | -0.5 | -0.6 | 1.05 | 0.93 | 0.65 | 0.45 | 1.06 | 1.02 |
| 0.81 | 2    | 2.27 | -0.2 | -0.6 | 0.33 | 1.56 | 0.45 | 0.59 | 0.7  | 0.9  |
| 1.05 | 1.85 | 1.63 | -0.3 | -0.2 | -0.1 | 1.35 | 0.69 | 0.45 | 0.81 | 1.04 |
| 0.52 | 1.89 | 1.86 | -0.2 | -0.6 | 0.77 | 0.81 | 0.70 | 0.33 | 1.1  | 1.12 |
| 240  | -236 | -228 | 202  | 201  | -226 | -233 | 248  | -246 | -246 | -262 |

FIG. 19I

| | | | | | | | | | |
|---|---|---|---|---|---|---|---|---|---|
| 2.98 | 4.21 | 2.33 | 2.2 | 0.24 | -0 | 1.35 | 2.02 | 4.33 | 3.89 |
| 3.55 | 3.74 | 2.46 | 2.74 | 0.66 | 0.55 | 1.34 | 1.21 | 4.16 | 4.26 |
| 4.21 | 3.1 | 3.35 | 2.73 | 1.01 | 0.87 | 1.13 | 1.72 | 3.98 | 4.12 |
| 3.15 | 2.66 | 3.03 | 2.14 | 1.96 | 0.96 | 5.2 | 6.29 | 4.42 | 4.39 |
| 2.81 | 2.67 | 2.4 | 1.93 | 1.63 | 1.77 | 5.95 | 5.29 | 4.08 | 3.95 |
| 3.55 | 2.56 | 2.54 | 2.47 | 1.7 | 2.49 | 5.53 | 4.93 | 3.76 | 4.22 |
| 2.51 | 2.29 | 2.72 | 2.7 | 2.67 | 3.4 | 3.38 | 4.09 | 3.29 | 3.16 |
| 2.87 | 2.49 | 2.4 | 2.24 | 2.66 | 3.41 | 2.25 | 3.22 | 3.52 | 3.28 |
| 2.1 | 2.26 | 1.84 | 2.37 | 1.67 | 2.22 | 2.02 | 1.84 | 3.08 | 2.71 |
| 2.21 | 2.45 | 1.14 | 1.77 | 0.58 | 1.19 | 2.38 | 1.62 | 3.17 | 3.11 |
| 2.54 | 2.43 | 1.91 | 1.7 | 0.47 | 1.26 | 1.34 | 1.83 | 3.45 | 2.78 |
| 2.33 | 1.59 | 0.63 | 2.02 | 0.12 | 0.79 | 1.57 | 1.26 | 2.4 | 2.52 |
| 2.76 | 2.55 | 0.91 | 1.2 | -0.2 | 0.11 | 0.91 | 0.96 | 2.55 | 2.47 |
| 2.29 | 2.04 | 1.55 | 2.1 | -0.2 | 0 | 1.22 | 0.92 | 2.37 | 2.13 |
| 2.22 | 1.96 | 1.67 | 1.96 | 0.3 | -0.1 | 0.51 | 0.88 | 2.11 | 2.2 |
| 2.29 | 2.23 | 2.68 | 1.57 | -0.2 | -0.3 | 0.57 | 0.84 | 2.28 | 1.71 |
| 1.53 | 2.75 | 2.93 | 1.67 | -0.3 | -0.3 | 0.58 | 0.75 | 1.9 | 1.78 |
| 2.49 | 1.76 | 2.55 | 0.81 | -0.4 | -0.4 | 0.05 | 0.1 | 1.25 | 1.36 |
| 2.3 | 2.54 | 1.42 | 0.17 | -0.3 | -0.3 | 0.55 | 0.25 | 1.97 | 1.42 |
| 2.03 | 2.53 | 0.77 | 0.47 | -0.3 | -0.2 | 0.3 | 0.47 | 1.6 | 1.69 |
| 2.35 | 1.96 | 0.73 | 0.37 | -0.4 | -0.2 | 0.32 | 0.38 | 1.32 | 1.34 |
| 2.96 | 2.3 | -0.1 | 0.27 | -0.3 | -0.3 | 0.48 | 0.27 | 1.08 | 0.83 |
| 2.36 | 1.77 | -0 | -0 | -0.3 | -0.3 | 0.22 | -0.1 | 1.2 | 1.05 |
| 2.3 | 2.65 | -0.2 | -0.1 | -0.2 | -0.2 | 0.1 | 0.46 | 1.13 | 0.97 |
| 1.81 | 1.78 | 0.16 | 0.01 | -0.3 | -0.3 | 0 | 0.09 | 0.75 | 0.68 |
| 2.38 | 1.91 | 0.2 | 0.1 | 0.3 | 0.2 | -0.1 | 0.24 | 0.58 | 0.67 |
| 1.73 | 2.28 | -0 | 0.1 | -0.3 | -0.3 | -0.2 | 0.13 | 0.77 | 0.49 |
| 2.13 | 2.04 | -0.1 | 0.25 | -0.3 | -0.3 | -0.1 | -0.1 | 0.39 | 0.78 |
| 1.68 | 2.34 | 0.16 | 0.03 | -0.2 | -0.2 | -0.1 | 0.05 | 0.82 | 0.55 |
| 256 | -253 | -225 | 214 | 171 | 168 | 196 | 199 | 242 | -245 |

FIG. 19J

| | | | | | | | | | |
|---|---|---|---|---|---|---|---|---|---|
| 4.93 | 4.43 | -0.3 | -0.3 | -0.5 | -0.5 | -0.3 | -0.3 | 1.05 | 1.15 | -0.5 |
| 4.76 | 4.44 | -0.5 | -0.2 | -0.4 | -0.4 | 0.5 | -0.3 | 1.72 | 2.18 | -0.6 |
| 5.24 | 4.57 | -0.5 | -0.2 | 0.5 | 0.3 | 0.1 | 0.00 | 2.31 | 2.63 | 0.4 |
| 4.13 | 5.1 | -0.4 | -0.4 | -0.4 | -0.3 | 0.07 | 0.34 | 2.27 | 2.54 | -0.2 |
| 4.71 | 4.37 | -0.4 | 0.4 | -0.4 | -0.4 | 0.11 | 0.87 | 2.08 | 2.05 | 0.57 |
| 3.92 | 4.4 | -0.5 | -0.4 | -0.3 | -0.3 | 0.66 | 1.17 | 2.59 | 2.15 | 1.23 |
| 4.15 | 4.31 | -0.4 | -0.2 | -0.3 | -0.3 | 1.03 | 2.02 | 1.52 | 1.9 | 2.08 |
| 3.41 | 3.85 | -0.4 | -0.4 | -0.5 | -0.2 | 1.41 | 1.76 | 1.09 | 1.34 | 1.73 |
| 3 | 3.79 | -0.5 | -0.5 | -0.3 | -0.6 | 1.76 | 2.17 | 0.93 | 1.43 | 1.04 |
| 2.78 | 3.77 | -0.4 | -0.5 | -0.4 | -0.3 | 1.41 | 1.36 | 0.98 | 0.83 | 0.83 |
| 2.54 | 3.48 | -0.3 | -0 | -0.3 | -0.2 | 1.2 | 1.55 | 0.18 | 0.26 | 0.94 |
| 2.39 | 3.13 | -0.3 | -0.3 | -0.4 | -0.3 | 0.33 | 0.8 | 0.11 | 0.01 | 1.38 |
| 2.14 | 2.01 | -0.4 | 0.1 | 0.3 | 0.4 | 0.07 | 0.24 | 0.26 | -0.3 | 0.6 |
| 1.64 | 1.8 | -0.3 | -0.3 | -0.3 | -0.4 | -0.1 | 0 | -0.2 | -0.3 | 0.56 |
| 1.8 | 1.72 | 0.1 | -0 | 0.3 | 0.3 | -0.1 | 0.04 | -0.2 | 0.3 | 0.54 |
| 1.48 | 1.24 | -0.3 | 0.1 | -0.3 | -0.4 | -0.4 | 0.01 | -0.3 | -0.2 | -0.2 |
| 1.01 | 1.06 | 0.02 | -0.2 | 0.3 | 0.3 | 0.4 | -0.1 | -0.2 | 0.1 | 0.2 |
| 1.15 | 0.69 | 0.1 | -0.2 | 0.4 | 0.4 | 0.2 | -0.3 | -0.3 | -0.3 | 0.1 |
| 0.95 | 0.94 | 0.07 | 0.05 | -0.3 | -0.3 | -0.3 | -0.3 | 0.1 | -0.2 | -0.1 |
| 0.76 | 0.83 | 0.06 | -0 | -0.2 | -0.3 | -0.3 | -0.2 | -0.2 | -0.4 | -0.2 |
| 0.57 | 0.44 | 0.06 | -0.2 | -0.3 | -0.2 | -0.3 | -0.2 | -0.3 | -0.1 | -0.3 |
| 0.45 | 0.21 | -0 | -0.1 | -0.3 | -0.2 | -0.2 | -0.2 | -0.2 | -0.2 | -0.2 |
| 0.25 | 0.48 | 0.17 | -0 | -0.2 | -0.4 | -0.2 | -0.2 | -0.3 | -0.3 | -0.3 |
| 0.27 | 0.45 | 0.15 | 0.41 | -0.2 | -0 | -0.3 | -0.1 | -0.1 | -0.1 | -0.2 |
| 0.05 | 0 | 0.25 | -0.2 | -0.4 | -0.4 | -0.2 | -0.2 | -0.2 | -0.3 | -0.3 |
| 0 | 0.05 | -0.2 | 0.04 | 0.2 | 0.3 | 0.3 | 0.2 | 0.2 | 0.1 | 0.2 |
| -0 | -0 | -0.2 | -0.3 | -0.3 | -0.2 | -0.2 | -0.2 | -0.1 | -0.2 | -0.2 |
| 0.2 | 0 | -0 | -0.2 | -0.2 | -0.3 | -0.2 | -0.1 | -0.1 | -0.1 | -0.2 |
| 0.12 | 0.08 | 0.05 | 0.01 | 0.2 | 0.3 | -0.2 | -0.1 | -0.1 | -0.2 | 0.2 |
| -232 | -229 | -148 | 153 | -148 | 150 | 164 | 168 | 169 | 170 | 158 |

FIG. 19K

| | | | | | | | |
|---|---|---|---|---|---|---|---|
| -0.5 | -0.2 | 0.4 | 3.32 | -0.4 | -0.3 | -0.2 | -0.3 |
| -0.5 | 0.32 | 0.63 | 3.4 | -0.4 | -0.5 | 0.3 | 0.2 |
| -0.4 | 0.54 | 0.81 | 2.84 | 0.4 | 0.2 | 0.2 | 0.2 |
| -0.4 | 0.89 | 0.73 | 2.6 | -0.6 | -0.4 | 0.3 | 0.2 |
| -0 | 0.38 | 1.35 | 1.81 | -0.5 | 0.4 | -0.2 | -0.3 |
| 0.49 | 0.52 | 0.96 | 2.04 | -0.3 | -0.4 | -0.2 | -0.2 |
| 1.49 | 1.14 | 1.38 | 1.91 | 0.4 | -0.4 | -0.2 | -0.2 |
| 1.43 | 0.66 | 0.69 | 0.58 | -0.4 | -0.3 | -0.2 | -0.1 |
| 1.59 | 0.44 | 0.38 | -0.2 | -0.4 | -0.3 | -0.2 | -01 |
| 0.92 | 0.87 | 0.36 | 0.21 | -0.3 | -0.3 | -0.1 | -0.2 |
| 1.66 | 0.41 | 0.24 | 0.07 | -0.2 | -0.2 | 0 | 0 |
| 1.43 | -0.1 | -0.1 | 0.01 | -0.2 | -0.2 | 0.2 | 0.1 |
| 1.28 | 0.1 | 0.2 | 0.2 | 0.2 | 0.3 | 0.01 | -0 |
| 0.98 | -0.3 | 0.3 | -0.1 | -0.1 | 0.1 | -0.1 | 0 |
| 0.55 | 0.3 | -0.3 | 0 | 0.1 | 0.1 | 0.16 | 0.15 |
| 0.25 | -0.4 | -0.2 | -0.1 | -0.1 | -0.1 | -0 | -0.1 |
| -0.1 | -0.4 | -0.3 | 0.2 | -0.2 | 0.1 | 0.03 | 0.22 |
| 0.1 | 0.3 | 0.4 | -0.3 | 0.1 | 0.1 | 0.05 | 0.02 |
| 0.2 | -0.2 | -0.3 | -0.1 | -0 | -0 | 0.12 | 0.11 |
| -0.3 | -0.4 | -0.3 | -0.2 | 0.01 | 0.04 | 0.1 | 0.27 |
| -0.3 | -0.3 | -0.3 | -0.1 | -0 | 0.09 | 0.15 | 0.26 |
| -0.2 | -0.2 | 0.2 | 0.13 | 0.06 | 0.13 | 0.16 | 0.2 |
| -0.2 | -0.3 | -0.4 | 0.1 | 0.11 | 0.27 | 0.31 | 0.23 |
| -0.2 | -0.2 | -0.1 | -0.1 | 0.2 | 0.15 | 0.12 | 0.21 |
| -0.2 | -0.2 | -0.2 | -0.3 | 0.14 | 0.1 | 0.31 | 0.23 |
| 0.3 | 0.2 | 0.3 | -0.1 | 0.23 | 0.14 | 0.23 | 0.23 |
| -0.2 | -0.2 | -0.2 | 0 | 0.18 | 0.27 | 0.22 | 0.22 |
| -0.3 | -0.2 | -0.2 | 0.05 | 0.22 | 0.29 | 0.17 | 0.3 |
| 0.2 | -0.1 | -0.2 | -0.1 | 0.26 | 0.26 | 0.3 | 0.34 |
| 158 | 155 | 155 | 183 | 148 | -150 | 158 | 158 |

FIG. 19L

NUCLEIC ACID REACTION TOOL, NUCLEIC ACID DETECTION/QUANTIFICATION KIT, AND NUCLEIC ACID DETECTION/QUANTIFICATION METHOD

CROSS-REFERENCE TO RELATED APPLICATIONS

This application is based upon and claims the benefit of priority from Japanese Patent Application No. 2018-045901, filed Mar. 13, 2018, the entire contents of which are incorporated herein by reference.

FIELD

Embodiments described herein relate generally to a nucleic acid reaction tool, a nucleic acid detection/quantification kit, and a nucleic acid detection/quantification method.

BACKGROUND

Currently, genetic tests are carried out in various scenes such as clinical sites and criminal investigations along with the progress of genetic testing technology. The gene to be tested is detected or quantified by the real-time PCR method or LAMP method. For example, the real-time PCR method has high sensitivity and a wide quantification range, since it involves amplification of nucleic acid. In the LAMP method, a target gene can be detected and/or quantified without labeling with a fluorescent dye.

Genetic tests are often useful only when a plurality of target genes is detected and the results thereof are synthesized. For example, in the identification of pathogenic bacteria infecting patients carried out in a clinical site, it is preferable to examine a plurality of types of microorganisms suspected to be infected based on the symptoms of patients. In addition, in individual identification or the like carried out in a criminal investigation, a repetitive sequence at a plurality of gene loci is inspected to identify an individual comprehensively. Accordingly, an individual can be identified with high probability. Therefore, techniques for detecting a plurality of target genes have become very important.

Conventionally, when detecting a plurality of target genes, amplification reactions are carried out in different reaction vessels for each of the plurality of target genes to detect the presence or absence of each target gene. Alternatively, when the amplification reaction is carried out in one reaction vessel, a multi-nucleic acid amplification reaction is carried out in one reaction vessel containing reagents for amplifying all target genes. Detection of an amplification product is generally carried out by subjecting the amplification product to a DNA chip, electrophoresis or the like. Alternatively, amplification and detection of a target gene can also be carried out using a multi-nucleic acid reaction vessel in which a plurality of types of primer sets or a plurality of types of probe nucleic acids is fixed.

Under the circumstances described above, further development of a method for detecting and/or quantifying nucleic acid conveniently and highly sensitively is currently desired.

BRIEF DESCRIPTION OF THE DRAWINGS

The patent or application file contains at least one drawing executed in color. Copies of this patent or patent application publication with color drawing(s) will be provided by the office upon request and payment of the necessary fee.

FIG. 5 is a flowchart showing an example of a nucleic acid detection/quantification method according to an embodiment;

FIG. 6 is a flowchart showing an example of the nucleic acid detection/quantification method according to an embodiment;

FIG. 11 is a perspective view showing an example of a nucleic acid reaction cassette according to an embodiment;

FIGS. 18A to FIG. 18I provide a diagram showing an experimental result of Example 1;

FIGS. 19A to 19L provide a diagram showing an experimental result of Example 2; and FIG. 20 is a diagram showing experimental results of Example 3.

DETAILED DESCRIPTION

In general, according to one embodiment, a nucleic acid reaction tool comprising: a support having a first surface, a covering body having a second surface, and a groove opened on the second surface, and a primer set. The covering body is in contact with the support to form a reaction space surrounded by the first surface and the groove. The groove includes, on an inner surface of the reaction space, side surfaces opposed to each other, and a rear surface connecting one end of the side surfaces, and a primer fixing region to which the primer set is fixed, the primer fixing region being located at a corner where the one end of the side surfaces connected to the rear surface in the reaction space.

If the nucleic acid reaction tool is intended for simultaneously detecting a plurality of types of target nucleic acids, a plurality of types of primer sets may be used. When a plurality of types of primer sets is included, a plurality of primer fixing regions may be arranged. In that case, the plurality of primer is fixed releasably to each of the plurality of primer fixing regions by type.

Hereinafter, various embodiments will be described with reference to the drawings. Each diagram is a schematic diagram to promote an understanding of the embodiment. The shape, dimensions, and ratios thereof may be different from actual ones. The design of these can appropriately be changed in consideration of the description that follows and publicly known technology.

First Embodiment (Nucleic Acid Reaction Tool)

Figure 1:
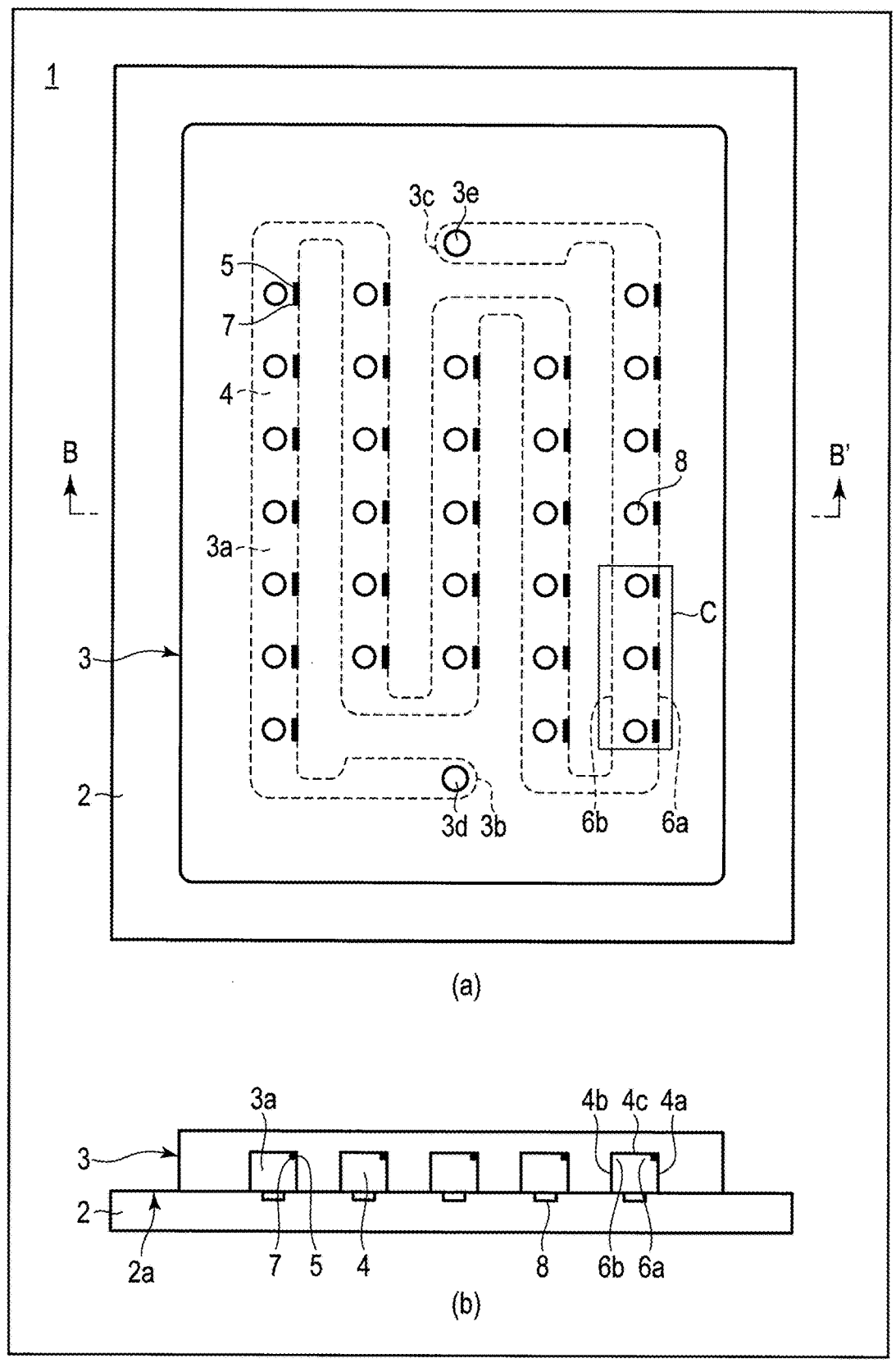
FIG. 1 is a plane view and a sectional view showing an example of a nucleic acid reaction tool according to an embodiment.
Figures 2, 4:
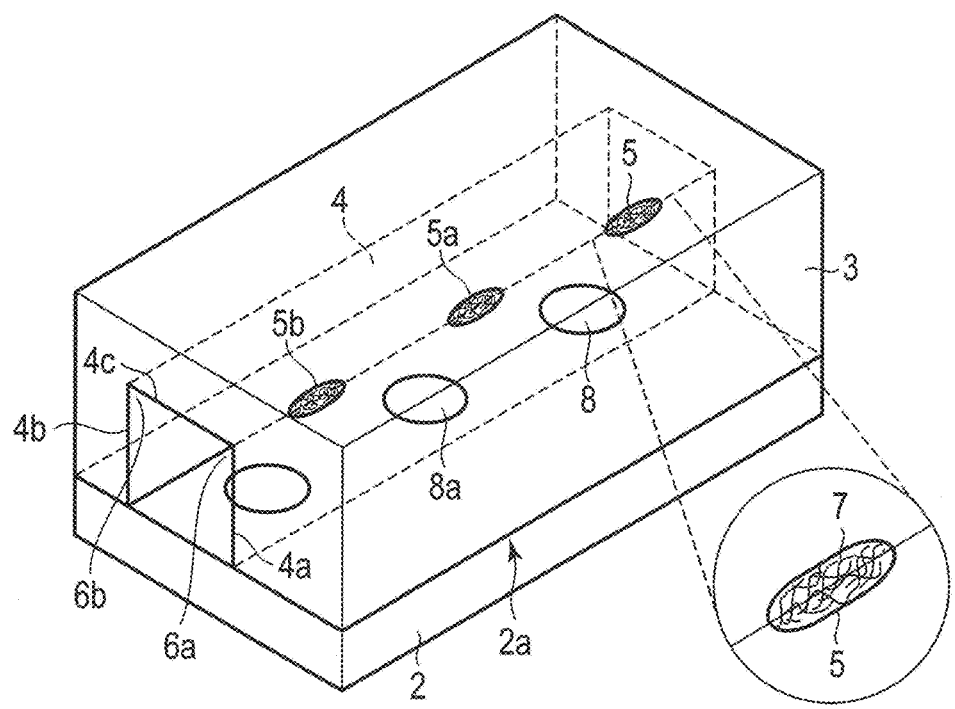
FIG. 2 is a transparent perspective view showing an example of the nucleic acid reaction tool according to an embodiment.
FIG. 4 is a transparent perspective view showing an example of the nucleic acid reaction tool according to an embodiment.

An example of the nucleic acid reaction tool according to a first embodiment is shown in FIG. 1. FIG. 1(a) is a plane view of a nucleic acid reaction tool 1. FIG. 1(b) is a sectional view of the nucleic acid reaction tool 1 when cut along B-B'. FIG. 2 is an enlarged transparent perspective view of an enclosure C in FIG. 1(a).

Hereinafter, an overview of the configuration of the nucleic acid reaction tool 1 will be provided. The nucleic acid reaction tool 1 includes, for example, a support 2 in a rectangular plate shape and a covering body 3 forming a plate-like rectangular body. The support 2 has a first surface 2a and the covering body 3 has a second surface. The covering body 3 has, for example, a groove 3a in an elongated shape, which is opened on the second surface. The second surface of the covering body 3 is in contact with and fixed to the first surface 2a of the support 2. Accordingly, a reaction space 4 in an elongated shape surrounded by the first surface 2a of the support 2 and the groove 3a of the covering body 3 is formed.

The reaction space 4 has a serpentine flow path shape. In a plane view, a starting end 3b side of the reaction space 4 is bent inward by 90°, further bent by 180° so as to be parallel to each other at four positions, and a terminal 3c side is bent inward by 90°. An inflow port 3d of a reaction liquid is opened at the position of the starting end 3b of the groove 3a and an outflow port 3e is opened at the position of the terminal 3c.

As shown in FIG. 1(b), the groove 3a of the covering body 3 has, on the inner surface of the reaction space 4, side surfaces 4a, 4b opposed to each other along the length direction of the groove 3a, and a rear surface 4c connecting one end (upper end) of these side surfaces 4a, 4b. The side surfaces 4a, 4b extend from both ends of the rear surface 4c to the flat surface 2a of the support 2 in a direction perpendicular. That is, the cross section of the reaction space 4 has a rectangular shape. The cross section of the reaction space 4 may have a square shape.

A plurality of primer fixing regions 5 is arranged in the length direction of at least one of corners 6a, 6b (where the one end of the two side surfaces 4a, 4b connected to the rear surface 4c), for example, the corner 6a at desired intervals. A plurality of primer sets 7 is fixed releasably to the plurality of primer fixing regions 5 respectively.

The support 2 includes a plurality of detection regions 8. The plurality of detection regions 8 is buried in the first surface 2a of the support 2 in contact with the reaction space 4, in proximity to the plurality of primer fixing regions 5 respectively.

Hereinafter, each component will be described in detail.

The support 2 is a solid that supports the covering body 3. The support 2 is, for example, in the form of a thin plate. The material of the support 2 is, for example, metal, glass, resin or silicon etc. The size of the support 2 is preferably, for example, 0.1 to 100 mm in length, 0.1 to 100 mm in width, and 0.1 to 10 mm in thickness, but is not limited to the above size. The support 2 may be in the form of a dish or a container. The support 2 may be, for example, a commercially available plate, dish, petri dish or other containers.

The covering body 3 covers at least a portion of first surface 2a of the support 2 and is a member to form the reaction space 4. The material of the covering body 3 desirably has flexibility. The material of the covering body 3 is preferably, for example, a hydrophobic resin. The hydrophobic resin is, for example, a silicone resin or the like. For example, the size of the covering body 3 is preferably 1 to 100 mm in length, 1 to 100 mm in width, and 0.1 to 10 mm in thickness, but is not limited to the above size. The depth of the groove 3a, that is, the height of the reaction space 4 is preferably, for example, 0.01 to 10 mm, and more preferably, 0.1 to 5 mm.

One reaction space 4 surrounded by the first surface 2a of the support 2 and the groove 3a of the covering body 3 is formed. Though details will be described below, the reaction space 4 is a space into which a reaction liquid is brought, and in which an amplification reaction of a target nucleic acid is carried out. Thus, the reaction space 4 is preferably a liquid-tight space.

The shape of the reaction space 4 is determined by the shape of the groove 3a. In the example shown in FIG. 1, the shape of the reaction space 4 is one serpentine flow path. It is preferable that the reaction space 4 is a flow path, because the amount of reaction liquid to be used may be small and also, the primer set 7 is less likely to diffuse to a region where a reaction of another type of the primer set 7 occurs. The width of the flow path is preferably, for example, 0.01 to 10 mm, and more preferably, 0.1 to 5 mm.

In this example, the flow path is one serpentine flow path, but the flow path may be, for example, one flow path that does not meander, a branched flow path, a spiral flow path or the like. The cross section of the flow path may not be rectangular and may be, for example, square or trapezoidal.

The covering body 3 has the corners 6a, 6b. The corners 6a, 6b will be described using FIG. 2. The corners 6a, 6b are each corners where the one end of the side surfaces 4a, 4b connected to the rear surface 4c respectively. The corners 6a, 6b are located inside the reaction space 4.

The plurality of primer fixing regions 5 is arranged in the corner 6a. For example, that the primer fixing region 5 is arranged in the corner 6a means that the primer fixing region 5 is located in a region extending across the two surfaces, namely, the side surface 4a and the rear surface 4c, including the intersecting line between the side surface 4a and the rear surface 4c. The primer set 7 is releasably fixed to each of the primer fixing regions 5.

The plurality of primer fixing regions 5 is arranged independently of each other. "Independently arranged" means that when a reaction liquid is brought into the reaction space 4 and the primer set 7 is released into the reaction liquid, the primer fixing regions 5 are arranged at such intervals that the primer set 7 fixed to there hardly diffuses to a region where the amplification reaction of the primer set 7 fixed to an adjacent primer fixing region 5 occurs. Alternatively, "independently arranged" means that the primer fixing regions 5 are arranged at such intervals that the amplification reaction caused by the primer set 7 fixed to a certain primer fixing region 5 and the detection of a signal associated therewith are hardly interfered with by the primer set 7 fixed to another primer fixing region 5. For example, the distance between the primer fixing regions 5 adjacent to each other is 1 mm or more. The distance is preferably 4 mm or more and 8 mm or less.

As long as the plurality of primer fixing regions 5 is arranged independently of each other, each of the plurality of primer fixing regions 5 may be arranged in the corners 6a or in the corners 6b, or in both of the corners 6a, 6b. Alternatively, the plurality of primer fixing regions 5 may be arranged in any corner other than the corners 6a, 6b.

In the plurality of primer fixing regions 5, a plurality of types of the primer sets 7 is fixed for each type. That is, one type of primer set is fixed to one primer fixing region. One type of primer set is an assembly of primers necessary to amplify one type of target nucleic acid corresponding thereto. The plurality of types of primer sets is each primer sets to amplify a plurality of mutually different target nucleic acids.

The primer set 7 is a primer set for temperature changeable amplification reaction or a primer set for isothermal amplification. The temperature changeable amplification reaction is, for example, PCR or the like. The isothermal amplification reaction is, for example, LAMP, RT-LAMP, SDA, NASBA, RCA, LCR, TMA, SmartAmp (registered trademark), ICAN (registered trademark) or the like.

When the primer set 7 is for PCR amplification, one type of primer set includes, for example, at least a forward primer and a reverse primer. When the primer set is for LAMP, one primer set includes, for example, at least an FIP primer and a BIP primer. Further, a F3 primer, a B3 primer, an LP primer, that is, an LF primer and/or LB primer may be included.

Each of the primer sets included in the plurality of types of primer sets 7 is preferably a primer set used for the same type of amplification method.

Each of the plurality of primer sets 7 is releasably fixed to the primer fixing region 5. "Releasably fixed" means that before the reaction liquid is brought into the reaction space 4, the primer set 7 is fixed to the primer fixing region 5, and after the reaction liquid has been brought into the reaction space 4, the primer set 7 can be released in the reaction liquid. For example, when heat is applied to the reaction space 4 or the reaction liquid, the primer set 7 is released into the reaction liquid.

For example, in order to releasably fix the primer set 7, a liquid containing the primer set 7 (hereinafter, referred to as a "primer solution") is dropped onto a desired primer fixing region and then dried. When the material of the covering body 3 is a hydrophobic resin, the dropped primer solution does not spread along the side surface 4a or the rear surface 4c. As a result, the primer solution can be made to stay at the corner 6a so that the primer set 7 can be fixed to the primer fixing region 5 more accurately.

Further, the covering body 3 preferably includes a surfactant film on the surface of at least a corner to which the primer set 7 is fixed (the corner 6a in the example of FIG. 2). When the surfactant film is provided in the corner 6a, the dropped primer solution hardly deviate from the dropped position so that the primer set 7 can be fixed to the primer fixing region 5 more accurately.

The surfactant film can be formed by, for example, bringing a liquid containing a surfactant into contact with a desired surface of the covering body 3, then rinsing to such an extent that the surfactant is not completely removed, and drying. The surfactant is, for example, Tween (registered trademark), Triton (registered trademark), Brij (registered trademark), a nonionic surfactant or the like. A liquid containing a surfactant is, for example, a liquid formed by containing a surfactant into a liquid such as water, salt water or a buffer solution.

The primer solution contains, for example, a primer set and a solvent. The solvent is preferably, for example, water. The concentration of the primer set in the primer solution is preferably, for example, 0.1 to 200 µM, and more preferably, 1 to 50 µM.

Further, the support 2 comprises a detection region 8. The detection region 8 is arranged in a region in contact with the reaction space 4 on the first surface 2a of the support 2. The detection region 8 is arranged corresponding to the primer fixing region 5. "Arranged corresponding to" means that the detection region 8 can detect a signal associated with the amplification reaction of the primer set 7 fixed to a corresponding primer fixing region 5, and the position or size of the detection region 8 is set so as not to detect a signal generated by the amplification reaction generated by adjacent primer sets. For example, a detection region 8a can detect a signal associated with the amplification reaction caused by a primer set fixed to a corresponding primer fixing region 5a. In addition, the detection region 8a is formed with such a size and arrangement so as not to detect a signal associated with the amplification reaction caused by, for example, a primer set fixed to a primer fixing region 5b.

The detection region 8 includes, for example, a member for detecting a signal associated with an increase of amplification products. The signal associated with an increase of amplification products is, for example, an electrochemical signal. The electrochemical signal is, for example, a current value, a potential value, an electric capacitance value, an impedance value or the like generated in the reaction space 4. When the signal is an electrochemical signal, the member for detecting the signal is, for example, an electrode.

Alternatively, the signal is an optical signal. The optical signal is fluorescence or chemiluminescence generated in the reaction space 4. Alternatively, the optical signal is coloration, turbidity, or absorbance of a reaction liquid (for example, absorption, scattering, reflection intensity when a reaction liquid is irradiated with light) or the like. When the signal is an optical signal, the member for detecting the signal is, for example, an optical sensor or a detection window.

When the detection region 8 includes an electrode, for example, the electrode is arranged so as to be able to detect an electrochemical signal generated inside the reaction space 4. The electrode can be obtained by, for example, forming a metal pattern having a desired shape such as a dot on the surface on the reaction space 4 side of the detection region 8. The electrode may be formed by stacking a plurality of metal films. Metal is preferably, for example, gold because it has good sensitivity. When the detection region 8 is formed of an electrode, the first surface of the support 2 other than the detection region 8 may be covered with an insulating film.

Figure 3:
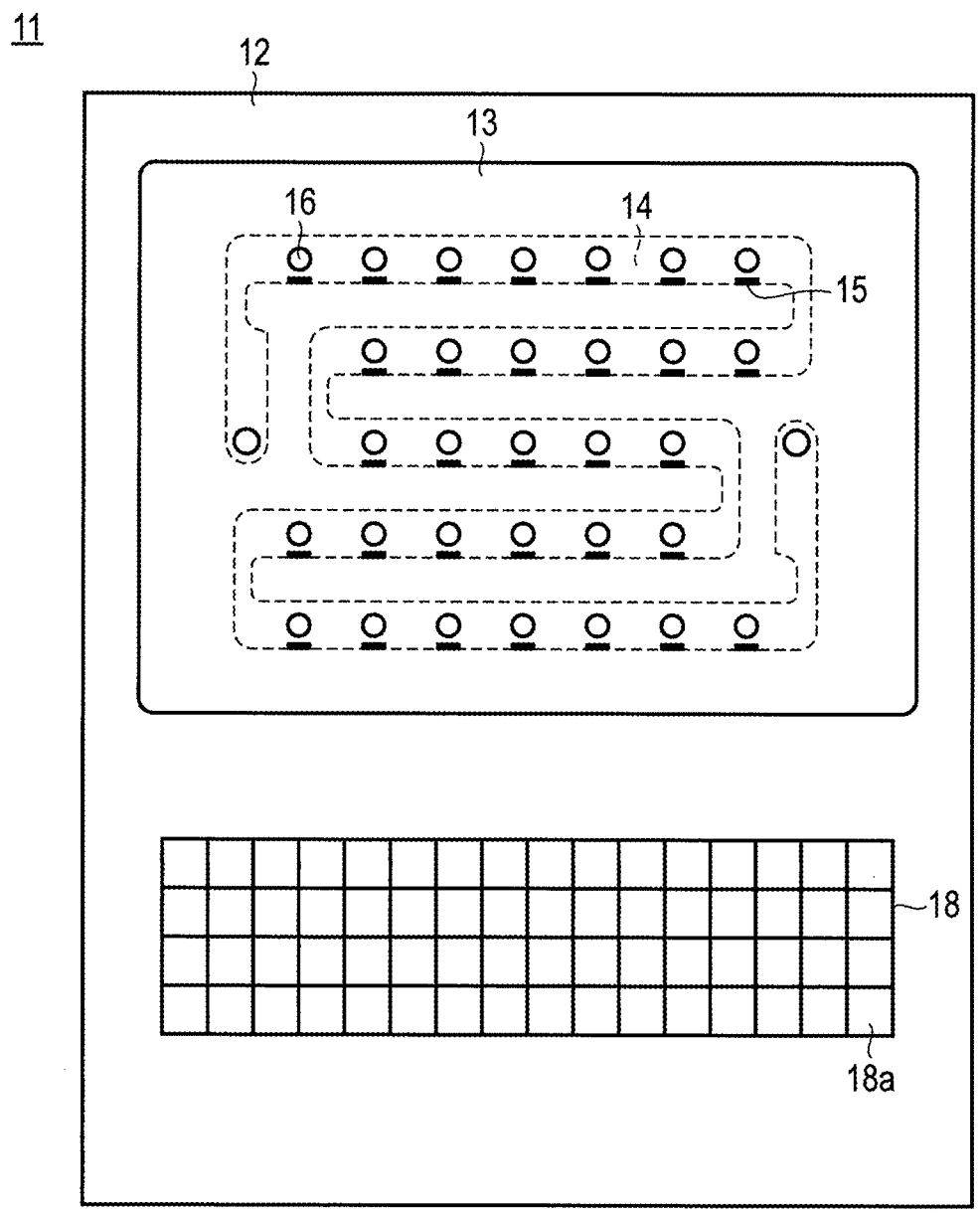
FIG. 3 is a plane view and a sectional view showing an example of the nucleic acid reaction tool according to an embodiment.

When the detection region 8 is formed of an electrode, the support 2 may include a pad portion. An example of such a nucleic acid reaction tool 11 is shown in FIG. 3. The nucleic acid reaction tool 11 includes an electrode 16 arranged corresponding to a primer fixing region 15 on the first surface of a support 12 in contact with a reaction space 14. Further, the support 12 includes a pad portion 18 on the first surface not covered with a covering body 13. The pad portion 18 includes a plurality of pads 18*a*. The pad 18*a* is electrically connected to the electrode 16 by a wiring or the like and can extract information about an electrochemical signal obtained by the electrode 16. In addition, the support 12 may further include a reference electrode and a counter electrode (not shown). Also, additional pads corresponding thereto may be included.

When the detection region 8 of the nucleic acid reaction tool 1 shown in FIG. 1 includes an optical sensor, for example, the optical sensor is arranged to be able to detect an optical signal generated in the reaction space 4. The optical sensor may be, for example, any known sensor capable of detecting the optical signal. For example, the optical sensor is an element that detects an optical signal and converts the signal into an electrical signal. The optical sensor may be, for example, a turbidity sensor.

When the detection region 8 of the nucleic acid reaction tool shown in FIG. 1 includes a detection window, the detection window is made of a light transmissive material. The light transmissive material is, for example, a resin or the like. The detection window is configured to be able to detect a signal generated in the reaction space 4 from the outside of the nucleic acid reaction tool 1 by, for example, an optical sensor separate from the nucleic acid reaction tool 1 or by visual inspection or the like.

By detecting a signal accompanying an increase in amplification products by the detection region 8, the target nucleic acid can be detected or quantified based on the result thereof.

A plurality of types of probe nucleic acids may be fixed to the detection region 8 by type. Such an example is shown in FIG. 4. FIG. 4 is a transparent perspective view similarly to FIG. 2. In this example, the nucleic acid reaction tool includes a probe nucleic acid 9 in the detection region 8.

The probe nucleic acid 9 is fixed to the surface of the detection region 8 in contact with the reaction space 4. For example, the probe nucleic acid 9 can hybridize with an amplification product (not shown) generated by an amplification reaction of the target nucleic acid caused by the primer set 7 fixed to the primer fixing region 5 corresponding to the detection region 8 to which the probe nucleic acid 9 is fixed (hereinafter, such a primer set 7 referred to as a "corresponding primer set"). Therefore, the type of the probe nucleic acid 9 to be fixed is selected according to the type of a corresponding primer set 7. For example, the amplification product generated by the amplification reaction by a primer set 7*a* hybridizes with a probe nucleic acid 9*a*.

For example, the probe nucleic acid 9 is a single-stranded nucleic acid and contains at least a sequence capable of specifically hybridizing with the corresponding amplification product. In addition, for example, the probe nucleic acid 9 is a double-stranded nucleic acid, and one strand thereof contains at least a sequence capable of specifically hybridizing with the corresponding amplification product.

The length of the probe nucleic acid 9 may be, for example, 3 bases to 10 bases, 10 bases to 20 bases, 20 bases to 30 bases, 30 bases to 40 bases, 40 bases to 50 bases, 50 bases to 60 bases, 60 bases to 70 bases, 70 bases to 80 bases, 80 bases to 90 bases, or 90 bases to 100 bases and, for example, 10 bases to 50 bases.

Fixing of the probe nucleic acid 9 to the detection region 8 is not particularly limited, but may be performed via a terminal modifying group, for example, the mercapto group, the amino group, the aldehyde group, the carboxyl group, or biotin. The selection of these functional groups and fixing of the probe nucleic acid 9 can be achieved by publicly known means.

Further, the nucleic acid reaction tool may contain a labeling substance. The labeling substance is a substance that produces a detectable signal, for example, an electrochemical signal or an optical signal that changes with an increase of amplification products.

It is preferable that a labeling substance that generates an electrochemical signal (hereinafter, referred to as a "first labeling substance") is included in any one of the above nucleic acid reaction tool including electrodes. In that case, an electrochemical signal generated by the first labeling substance can be detected by the electrode, and the target nucleic acid can be detected or quantified based on the result thereof.

The first labeling substance is, for example, a double-strand recognition substance. The double-strand recognition substance is, for example, a substance that binds to a double-stranded nucleic acid formed from amplification products, or a probe nucleic acid and an amplification product. Examples of the double-strand recognition substance are, for example, bis intercalators such as Hoechst 33258, acridine orange, quinacrine, daunomycin, metallo intercalator, and bisacridine, tris intercalators, poly intercalators and the like. These double-strand recognition substances may be further modified with electrochemically active metal complexes. Such metal complexes are, for example, ferrocene, viologen and the like.

Alternatively, the first labeling substance may be, for example, an oxidizing agent or the like. In that case, the oxidation-reduction potential thereof becomes an electrochemical signal. The oxidizing agent that can be used as the first labeling substance is, for example, a redox probe or the like.

The redox probe is, for example, a metal complex. The metal complex is, for example, a complex containing ruthenium (Ru), rhodium (Rh), platinum (Pt), cobalt (Co), chromium (Cr), cadmium (Cd), nickel (Ni), zinc (Zn), copper (Cu), osmium (Os), iron (Fe), or silver (Ag) as the central metal. The complex is, for example, an amine complex, a cyano complex, a halogen complex, a hydroxy complex, a cyclopentadienyl complex, a phenanthroline complex, a bipyridine complex or the like. The complex is preferably, for example, ferricyanide ions, ferrocyanide ions or ruthenium hexaamine (RuHex). The redox probe may be, for example, a pigment. Examples of the pigment include methylene blue, nile blue, crystal violet and the like.

It is preferable that a labeling substance that generates an optical signal (hereinafter referred to as a "second labeling substance") is included in a nucleic acid reaction tool including any one of the above optical sensors or a detection window. In that case, an optical signal generated by the second labeling substance can be detected by an optical sensor or by visual inspection, and the target nucleic acid can be detected or quantified based on the result thereof.

Examples of the second labeling substance are not particularly limited and include, for example, Alexa fluor488, Alexa fluor532, Alexa fluor546, Alexa fluor555, Alexa fluor594, Alexa fluor647, Alexa fluor660, Alexa fluor750, BODIPY (registered trademark) 493/503, BODIPY (registered trademark) 530/550, BODIPY (registered trademark) 550/560, BODIPY (registered trademark) 558/569, BODIPY (registered trademark) 564/570, BODIPY (registered trademark) 576/589, BODIPY (registered trademark) 581/591, BODIPY (registered trademark) 630/650, BODIPY (registered trademark) FL, BODIPY (registered trademark) FL-X, BODIPY (registered trademark) R6G, BODIPY (registered trademark) R6G-X, BODIPY (registered trademark) TMR, BODIPY (registered trademark) TR-X, CASCADE BLUE (registered trademark), FAM, Fluorescein, Gateway FW, Gateway RV, HEX, JOE, Marina Blue (registered trademark), Oregon Green488, Oregon Green 488-X, Oregon Green500, and Oregon Green514, Pacific Blue (registered trademark), Rhodamine Green-X, Rhodamine Green (registered trademark), Rhodamine Red-X, Rhodamine, Rhodol Green, ROX, TAMRA, TET, Texas Red (registered trademark), Texas Red-X, Cy3, Cy3.5, Cy5, Cy5.5 and the like.

The labeling substance may be bound to the probe nucleic acid 9 (when contained), may be bound to any primer contained in the primer set 7, or may be releasably fixed to any surface in the reaction space 4 of the nucleic acid reaction tool. Alternatively, preferably, the labeling substance is not contained in the nucleic acid reaction tool, but is contained in the reaction liquid brought into the reaction space.

When the labeling substance is bound to the probe nucleic acid 9, the site to which the labeling substance is bound may be a binding portion of the probe nucleic acid 9 to the support 2, a non-binding terminal of the probe nucleic acid 9, or between the binding portion and the non-binding terminal of the probe nucleic acid 9. The method of binding the labeling substance to the probe nucleic acid 9 may be selected according to the type of the labeling substance, and any method for binding the nucleic acid and the labeling substance may be selected.

When the labeling substance is bound to a primer, the labeling substance may be bound to the end of the primer or a midpoint of the sequence of the primer, or may be bound to cover at least a portion of the sequence of the primer. The method of binding the labeling substance to a primer may be selected according to the type of the labeling substance, and any method for binding the nucleic acid and the labeling substance may be selected.

When the labeling substance is fixed to any surface in the reaction space 4, the labeling substance is fixed to, for example, the first surface in contact with the reaction space of the support.

In addition, other reagents necessary for the amplification reaction may be releasably fixed to the first surface of the support 2 or the covering body 3 in contact with the reaction space 4. Other reagents include, for example, salts, substrates such as deoxynucleoside triphosphates (dNTPs), thickeners, buffering agents for pH preparation, surfactants, ions that increase annealing specificity, and/or ions that become a cofactor of amplification enzymes.

However, the other reagents are preferably contained in the reaction liquid and brought into the reaction space 4, instead of being fixed to the covering body 3. In that case, it is difficult for the primer to diffuse when flowing into the reaction liquid, and a plurality of target nucleic acids can be detected more accurately. In particular, dNTPs are preferably fixed to a different position from the primer set, or contained in the reaction liquid and brought into the reaction space 4, instead of being fixed to the corner together with the primer set. In that case, it is more difficult for the primer to diffuse and the target nucleic acid can be detected more accurately.

The covering body 3 may further include a storage portion capable of separately storing a reaction liquid, a cleaning liquid, other reagents and a waste liquid. Further, a flow path connecting the storage portion and the reaction space 4 may be included.

The nucleic acid reaction tool 1 may include a plurality of reaction spaces 4 each capable of detecting a plurality of types of target nucleic acids as described above.

According to the nucleic acid reaction tool 1 described above, the primer set 7 is fixed to the corner 6a. Thus, when the reaction liquid is brought into the reaction space 4, it is very difficult for the primer set 7 to diffuse along the flow of the reaction liquid. Therefore, the diffusion of the primer set 7 into an undesired range is suppressed. As a result, the amplification reaction by a certain primer set is not interfered with by components of the other primer sets, and highly accurate detection or quantification can be performed. In addition, for the above reasons, the distance between the primer fixing regions 5 can be made shorter than before, and the primer fixing region 5 and the primer set 7 can be arranged at a higher density. For example, according to an embodiment, the distance between adjacent primer fixing regions can be made 4 to 8 mm. As a result, it is possible to detect or quantify more types of target nucleic acids at one time with one nucleic acid reaction tool 1.

The nucleic acid reaction tool described above may be used for detecting one type of target nucleic acid. In that case, one primer fixing region is provided and one type of primer set is fixed thereto and used. Even with such a nucleic acid reaction tool, the primer set is prevented from being diffused by the reaction liquid, and the target nucleic acid can be accurately detected or quantified by, for example, the detection region corresponding to the primer fixing region.

(Nucleic Acid Detection/Quantification Method)

Hereinafter, a nucleic acid detection/quantification method using the nucleic acid reaction tool according to the first embodiment will be described. FIG. 5 is a schematic flow chart showing an example of the nucleic acid detection/quantification method.

The nucleic acid detection/quantification method in this example is a method for detecting or quantifying first to n-th target nucleic acids in a sample. The method includes the following processes: preparing a nucleic acid reaction tool (S1), bringing a reaction liquid containing a sample and an amplification reagent into the reaction space of the nucleic acid reaction tool (S2), maintaining the reaction space under amplification conditions to obtain an amplification product (S3), detecting a signal changing with an increase of the amplification product for each primer fixing region (S4), and detecting or quantifying first to n-th target nucleic acid based on the detection results (S5). Here, n is an integer equal to 2 or greater.

Hereinafter, the nucleic acid detection/quantification method when the signal is an electrochemical signal, the nucleic acid detection/quantification method when the signal is an optical signal will be described in this order.

(Nucleic Acid Detection/Quantification Method Using Electrochemical Signal)

FIG. 6 is a schematic flow showing an example of the nucleic acid detection/quantification method using an electrochemical signal.

The nucleic acid detection/quantification method is a method for detecting first to n-th target nucleic acids in a sample. The method includes the following processes: preparing a nucleic acid reaction tool including at least first to n-th electrodes (S11), bringing a reaction liquid containing a sample and an amplification reagent into the reaction space of the nucleic acid reaction tool (S12), maintaining the reaction space under amplification conditions to obtain an amplification product (S13), detecting an electrochemical signal changing with an increase of the amplification product using the first to n-th electrodes (S14), and detecting or quantifying first to n-th target nucleic acids based on the detection results (S15). Here, n is an integer equal to 2 or greater.

Each process will be described in detail below.

In process (S11), a nucleic acid reaction tool including electrodes is prepared.

The nucleic acid reaction tool may be any type of the above nucleic acid reaction tool including electrodes. The number of electrodes included in the nucleic acid reaction tool is at least n, that is, as many as or more than the number of target nucleic acids to be detected or quantified.

A plurality of types of primer sets fixed to the nucleic acid reaction tool is first to n-th primer sets for amplifying first to n-th sequences contained in the first to n-th target nucleic acids contained in the sample respectively. The first to n-th primer sets are releasably fixed to first to n-th primer fixing regions independently arranged in corners where the one end of the side surface connected to the rear surface located in the reaction space.

In process (S12), a reaction liquid is brought into the reaction space of the nucleic acid reaction tool.

The reaction liquid brought into the reaction space contains a sample and an amplification reagent.

The sample is a substance in which the presence or absence of the target nucleic acid or the amount thereof is to be examined. In other words, the sample is an analysis target by the nucleic acid detection/quantification method according to an embodiment. The sample may be, for example, a biological material such as blood, serum, leukocyte, urine, feces, sweat, saliva, oral mucosa, phlegm, lymph, cerebrospinal fluid, lacrimal fluid, mother milk, amniotic fluid, semen, tissues, biopsy, cultured cells or the like, or an environmental material gathered from the environment, an artificial nucleic acid, or a mixture thereof. Alternatively, the sample may be preparations prepared using any above sample as a material. For example, in order to use any of the above as a sample according to the present embodiment, any known pretreatment such as shredding, homogenization, extraction or the like may be performed. Alternatively, for example, any of the above may be collected from a living body or the environment and prepared to a state suitable for nucleic acid detection. For example, a liquid containing a nucleic acid component obtained by extracting a nucleic acid by any means known from any of the above may be used as a sample.

The first to n-th target nucleic acids are nucleic acids to be detected or quantified by the nucleic acid detection/quantification method according to an embodiment. The first to n-th target nucleic acids are preferably, for example, nucleic acids having mutually different base sequences. The first to n-th target nucleic acids may be nucleic acids derived from mutually different organisms or nucleic acids derived from the same organism.

The first to n-th target nucleic acids include the first to n-th sequences respectively. Here, if the value of any one of 1 to n is t, the t-th target nucleic acid contains the t-th sequence. The t-th sequence is a sequence serving as an index of the presence of the t-th target nucleic acid and is a sequence amplified in the nucleic acid detection/quantification method. The t-th sequence is a sequence selected from the sequence extending over the entire length of the t-th target nucleic acid and is preferably, for example, a sequence specific to the t-th target nucleic acid.

The first to n-th target nucleic acids are single-stranded nucleic acids. The states of the first to n-th target nucleic acids in the sample are single strands or double strands formed by a single strand and a complementary nucleic acid strand.

The lengths of the first to n-th target nucleic acids are preferably, for example, 50 bases to 500 bases and more preferably, 100 bases to 300 bases.

The lengths of the first to n-th sequences are, for example, three bases to 10 bases, 10 bases to 20 bases, 20 bases to 30 bases, 30 bases to 40 bases, 40 bases to 50 bases, 50 bases to 60 bases, 60 bases to 70 bases, 70 bases to 80 bases, 80 bases to 90 bases, or 90 bases to 100 bases and preferably, 10 bases to 50 bases.

The amplification reagent is, for example, a reagent necessary for an amplification reaction to amplify the first to n-th sequences. The amplification reagent includes at least an amplification enzyme.

The amplification enzyme is selected based on, for example, the type of target nucleic acid, the type of amplification method used, the type of primer set, the presence or absence of reverse transcription reaction and the like. The amplification enzyme is, for example, DNA polymerase or RNA polymerase.

When the amplification enzyme is to be used in a temperature changeable amplification method, examples of the amplification enzyme include, for example, Csa DNA Polymerase, FastStart Taq DNA Polymerase, Gene Taq, HotStar Taq Plus DNA Polymerase, KAPA HiFi HotStart DNA Polymerase, KOD- Plus-, Mighty Amp DNA Polymerase Ver.2, OneTaq Hot Start DNA Polymerase, Phusion Hot Start Flex DNA Polymerase, PicoMaxx High Fidelity PCR System, Platinum Taq DNA Polymerase, Premix Ex Taq Hot Start Version, Pyrobest DNA Polymerase, Q5 Hot Start High-Fidelity DNA Polymerase, TaKaRa Ex Taq, and TaKaRa Ex Taq Hot Start Version.

If the amplification enzyme is to be used in an isothermal amplification method, examples of the amplification enzyme preferably include, for example, Bst, Bst 2.0, Bst 3.0, GspSSD, GspM, Tin, Bsm, Csa, 96-7, phi29, OminiAmp (registered trademark), Aac, BcaBEST (registered trademark), DisplaceAce (registered trademark), SD, StrandDisplace (registered trademark), TOPOTAQ, Isotherm2G, Taq, or any combination thereof.

In addition to the amplification enzyme, the amplification reagent may further contain magnesium, salt, a substrate such as deoxynucleoside triphosphate (dNTP), a thickener, a buffering agent for pH preparation, a surfactant, ions for increasing annealing specificity, and/or ions which become a cofactor of the amplification enzyme. When reverse transcription is performed simultaneously, the amplification reagent may further contain reverse transcriptase and a substrate necessary for the reverse transcriptase.

When any of the above components is contained in the nucleic acid reaction tool by being releasably fixed, for example, to any surface of the reaction space, such a component may not be contained in the reaction liquid.

The reaction liquid described above is brought into the reaction space. The reaction liquid may be brought into the reaction space, for example, through an opening formed in the covering body, or from the reaction liquid storage unit formed in the covering body via the flow path.

When an electrochemical signal generated by the first labeling substance is used, the reaction space contains the first labeling substance after the reaction liquid being brought into the reaction space. Any one of the above-mentioned first labeling substance can be used. For example, the first labeling substance may be contained in the reaction liquid in advance. Alternatively, the first labeling substance may be contained in a detection reagent separately prepared from the reaction liquid and brought into the reaction space separately from the reaction liquid. In addition to the first labeling substance, the detection reagent includes, for example, a solvent, a salt, or a surfactant. Alternatively, for example, the first labeling substance may be fixed to the surface in contact with the reaction space of the nucleic acid reaction tool in advance without being included in the reaction liquid.

Components contained in the reaction liquid described above need not be brought into the reaction space simultaneously. For example, a sample, an amplification reagent, and a detection reagent (if included) may be separately brought into the reaction space to form a reaction liquid in the reaction space.

In process (S13), the reaction space is maintained under amplification conditions.

The amplification conditions are selected based on, for example, the type of amplification method to be used, the type of primer set, the type of target nucleic acid and/or the type of amplification enzyme and the like. The amplification conditions are isothermal amplification reaction conditions or temperature changeable amplification reaction conditions. However, the amplification conditions are preferably isothermal amplification reaction conditions because convection of the reaction liquid caused by temperature change hardly occurs. When a reaction field is maintained under isothermal amplification conditions, for example, the temperature of the reaction field may be maintained between 25° C. and 70° C. More preferably, the temperature is maintained between 55° C. and 65° C. The isothermal amplification conditions are preferably, for example, LAMP reaction conditions.

Such temperature conditions can be carried out by, for example, a heating and cooling device separate from the nucleic acid reaction tool.

If any one of the first to n-th target nucleic acids is present in the sample, by maintaining the reaction field under the amplification reaction conditions, an amplification reaction using the target nucleic acid as a template is caused by the primer set corresponding thereto and an amplification product is generated. The amplification product is generated in the position where the primer set is fixed, that is, in the vicinity of the primer fixing region, and increases and remains in the vicinity thereof. For example, an amplification product amplified from one target nucleic acid molecule remains within the range of 1 to 4 mm from the primer fixing region.

In process (S14), an electrochemical signal changing with an increase of the amplification product is detected for each of the first to n-th electrodes. The electrochemical signal is generated by, for example, the first labeling substance. Alternatively, the electrochemical signal is generated due to an increase in nucleic acid (having a negative charge) in the vicinity of the electrode.

The signal changing with an increase of the amplification product means that the signal arises or extinguishes, changes in properties, increases or decreases due to, for example, the presence of an amplification product or an increase in abundance thereof. The change of signal is, in the case of, for example, an electrochemical signal, an increase, a decrease, disappearance, or a change of an integrated value within a specific time of a current value, a potential value, an electric capacitance value, an impedance value or the like.

The electrochemical signal is generated, for example, by the first labeling substance present in the reaction space. For example, with an increase of the amplification product (having a negative charge) in the vicinity of the detection region, the first labeling substance moves closer to or moves away from the detection region to change the signal. Alternatively, the signal is changed by the first labeling substance as a double-stranded nucleic acid recognition substance being bound to a double-stranded nucleic acid formed by binding an amplification product to a probe nucleic acid fixed to a detection region. The principle on which these signals change is by way of example, and the present invention is not limited thereto.

An electrochemical signal is detected for each electrode. That is, the signal is detected individually for all of the first to n-th electrodes. Accordingly, an electrochemical signal for each of the first to n-th target nucleic acids can be obtained individually.

The detection may be carried out, for example, at the end point of an amplification reaction. Alternatively, the detection may be carried out chronologically. Chronologically may be continuously or intermittently, that is, a signal is detected at a plurality of time points at desired intervals. For example, continuous detection may be signal monitoring. By detecting a signal chronologically over a desired period of time from the start of the amplification reaction, when an amplification product is present, a signal with a larger value can be obtained as compared with the case where no amplification product is present. Alternatively, a rising edge of the signal is observed at an earlier time point.

In process (S15), the first to n-th target nucleic acids are detected or quantified.

Assuming that one of the values 1 to n is t, the detection of the t-th target nucleic acid is, for example, to determine whether the t-th target nucleic acid is present in the sample. The quantification of the t-th target nucleic acid refers to, for example, determining the abundance, concentration, etc., of the t-th target nucleic acid in the sample.

Detection and/or quantification of the first to n-th target nucleic acids is performed based on the detection result in process (S14). That is, the t-th target nucleic acid is detected and/or quantified based on the detection result by the t-th electrode. For example, after measuring the time required for the electrical signal detected by the t-th electrode to exceed a predetermined threshold (rise time), the detection and/or quantification of the t-th target nucleic acid is performed based on the obtained result. Alternatively, the abundance of the t-th target nucleic acid in the sample may be calculated by preparing a plurality of different standard sample nucleic acids with known nucleic acid abundance, making measurements using the standard sample nucleic acids to create a calibration curve from measurement results obtained for the abundance of each nucleic acid, and by comparing the measurement results of the t-th target nucleic acid with the created calibration curve.

By performing such detection and/or quantification of the first to n-th target nucleic acids, a plurality of target nucleic acids can be detected and/or quantified with one nucleic acid reaction tool.

(Nucleic Acid Detection/Quantification Method Using Optical Signal)

Figure 7:
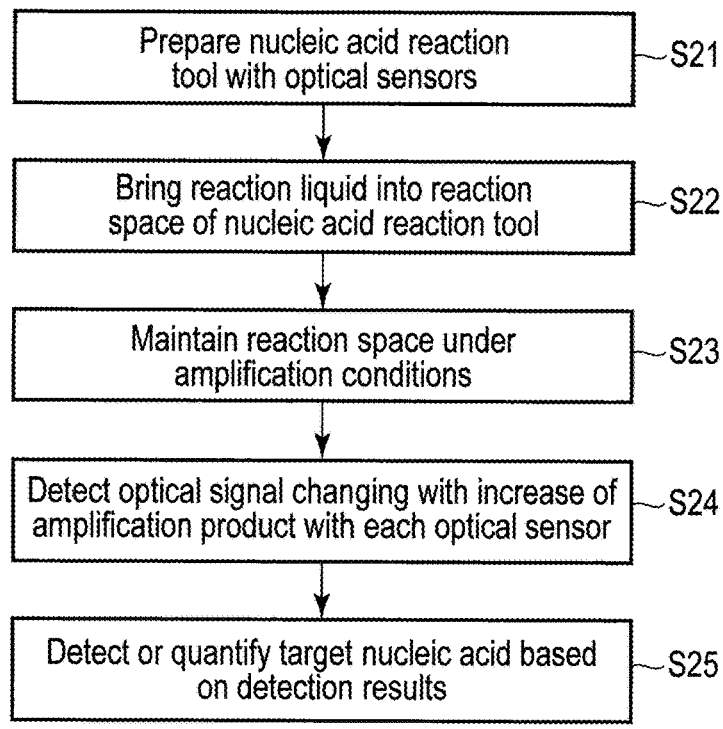
FIG. 7 is a flowchart showing an example of the nucleic acid detection/quantification method according to an embodiment.

FIG. 7 is a schematic flow showing an example of the nucleic acid detection/quantification method using an optical signal.

The nucleic acid detection/quantification method is a method for detecting first to n-th target nucleic acids in a sample. The method includes the following processes: preparing a nucleic acid reaction tool including at least first to n-th optical sensors (S21), bringing a reaction liquid containing a sample and an amplification reagent into the reaction space of the nucleic acid reaction tool (S22), maintaining the reaction space under amplification conditions to obtain an amplification product (S23), detecting an optical signal changing with an increase of the amplification product using the first to n-th optical sensors (S24), and detecting or quantifying first to n-th target nucleic acids based on the detection results (S25). Here, n is an integer equal to 2 or greater.

Each process will be described in detail below.

In process (S21), a nucleic acid reaction tool including optical sensors is prepared.

The nucleic acid reaction tool is any type of the above nucleic acid reaction tool including optical sensors. The number of optical sensors is at least n, that is, optical sensors as many as or more than the number of target nucleic acids to be detected or quantified are arranged.

A plurality of types of primer sets fixed to the nucleic acid reaction tool is first to n-th primer sets for amplifying first to n-th sequences contained in the first to n-th target nucleic acids contained in the sample respectively.

In process (S22), a reaction liquid is brought into the reaction space of the nucleic acid reaction tool.

The reaction liquid to be brought into the reaction space may be the same as any one of the above reaction liquids, but the reaction liquid in this example does not contain the first labeling substance. The reaction liquid can be brought into the reaction space, for example, in the same manner as in the above process (S12).

When an optical signal generated by the second labeling substance is used as an optical signal, the second labeling substance may be contained in the reaction space after performing process (S22). For example, the second labeling substance may be fixed in advance to the probe nucleic acid, the primer, or any surface in contact with the reaction space of the nucleic acid reaction tool. Alternatively, the second labeling substance may be brought into the reaction space by being contained in the reaction liquid.

The process (S23) can be performed in the same manner as the process (S13).

In process (S24), an optical signal changing with an increase of an amplification product is detected for each of the first to n-th optical sensors. The optical signal is, for example, a signal generated due to the presence of the second labeling substance or turbidity generated by an increase of the amplification product of the reaction liquid. The change of signal in this method may be, for example, an increase/decrease, occurrence, or disappearance in intensity of fluorescence or chemiluminescence, or change in wavelength thereof or the like. Alternatively, the change of signal may be an increase in turbidity or an increase in absorption, diffusion, or reflection when the reaction liquid is irradiated with light. For example, the optical signal may be changed by an amplification product being bound to a probe nucleic acid to which a second labeling substance is bound. Alternatively, the optical signal may be changed by a primer having a second labeling substance bound thereto being used to generate an amplification product. The principle on which these signals change is by way of example, and the present invention is not limited thereto.

The optical signal is detected for each optical sensor. That is, the signal is detected individually for all of the first to n-th optical sensors. Accordingly, an optical signal concerning each of the first to n-th target nucleic acids can be obtained. Detection may be performed, for example, at the end point of an amplification reaction or may be performed chronologically in the same manner as in the above process (S14).

Like in the above process (S15), the process (S25) may be performed, after measuring the time required for a signal to exceed the threshold value (rise time) based on the obtained result, or by creating a calibration curve and comparing a detection result with the calibration curve.

The nucleic acid detection/quantification method using an optical signal may be performed using a nucleic acid reaction tool having first to n-th detection windows, instead of the first to n-th optical sensors. In this example, the detection in process (S24) is performed, for example, from the detection window by an optical sensor separate from the nucleic acid reaction tool or visually for each of the first to n-th detection windows.

According to the nucleic acid detection/quantification method described above, the nucleic acid reaction tool according to an embodiment is used and thus, diffusion of the primer set when the reaction liquid is brought is suppressed. As a result, detection or quantification can be performed more accurately. In addition, primer fixing regions can be arranged at a high density and thus, more types of target nucleic acids can be detected or quantified using one nucleic acid reaction tool 1.

Second Embodiment (Nucleic Acid Reaction Tool)

Figure 8:
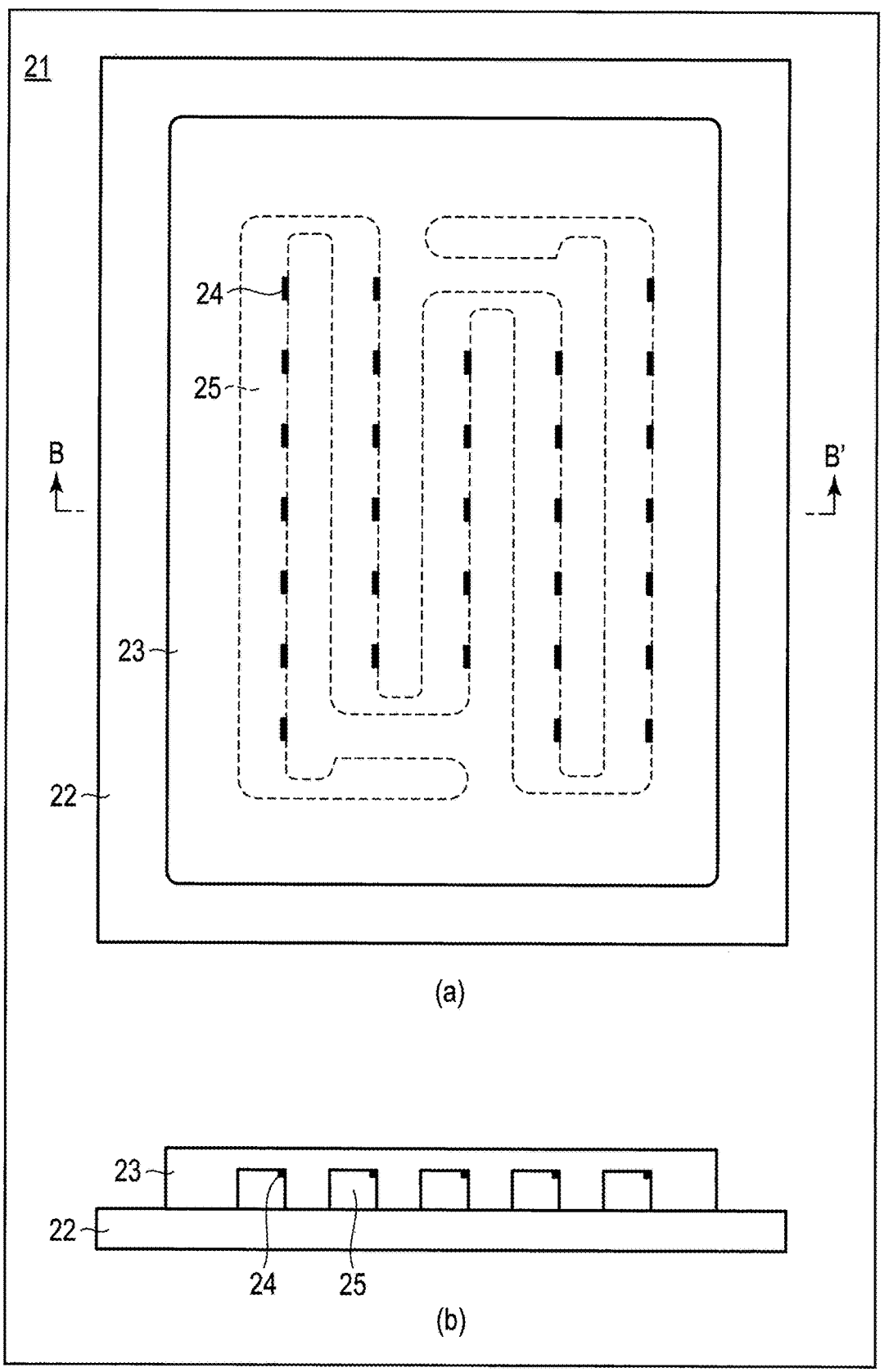
FIG. 8 is a plane view and a sectional view showing an example of a nucleic acid reaction tool according to an embodiment.

The nucleic acid reaction tool according to a second embodiment includes a support having no detection region, a covering body formed of a light transmissive member, and a plurality of types of primer sets. An example of the nucleic acid reaction tool in this example is shown in FIG. 8. FIG. 8(*a*) is a plane view of a nucleic acid reaction tool 21. FIG. 8(*b*) is a sectional view when the nucleic acid reaction tool 21 is cut along B-B'. The nucleic acid reaction tool 21 includes a support 22, a covering body 23, and a plurality of types of primer sets 24.

As the support 22, any support that is the same as above-described ones can be used except that the support includes no detection region.

As the covering body 23, those having the same structure and material as those of any of the covering bodies described above can be used. However, the covering body 23 is formed of a light transmissive material. The covering body 23 is transparent or translucent to such an extent that an optical signal from a reaction liquid brought into a reaction space 25 can be detected from the outside of the nucleic acid reaction tool 21 through the covering body 23.

As the plurality of types of primer sets 24, any one of the above-described ones can be used. The plurality of types of primer sets 24 is fixed to the corners of the covering body 23 in the same manner as any one of the above-described ones.

In the nucleic acid reaction tool 21 described above, the covering body 23 is formed of a light transmissive member and so can detect an optical signal without including any detection region.

(Nucleic Acid Detection/Quantification Method)

Figure 9:
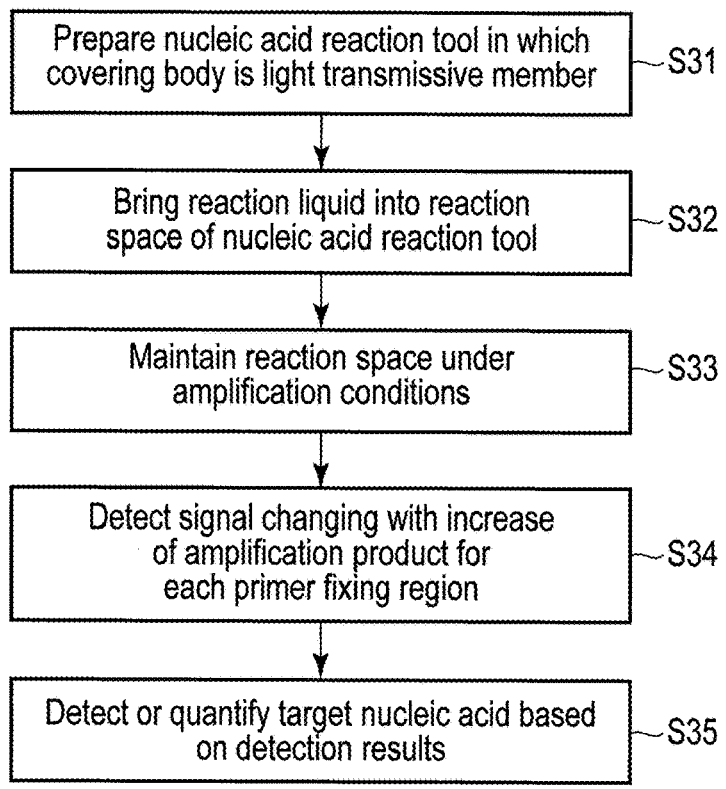
FIG. 9 is a flowchart showing an example of the nucleic acid detection/quantification method according to an embodiment.

Hereinafter, the nucleic acid detection/quantification method using the nucleic acid reaction tool according to the second embodiment will be described. FIG. 9 is a schematic flow showing an example of the nucleic acid detection/quantification method in this example.

The nucleic acid detection/quantification method is a method for detecting first to n-th target nucleic acids in a sample. The method includes the following processes: preparing a nucleic acid reaction tool in which the covering body is a light transmissive member (S31), bringing a reaction liquid containing a sample and an amplification reagent into the reaction space of the nucleic acid reaction tool (S32), maintaining the reaction space under amplification conditions to obtain an amplification product (S33), detecting a signal changing with an increase of the amplification product for each primer fixing region (S34), and detecting or quantifying a target nucleic acid based on the detection result (S35). Here, n is an integer equal to 2 or greater.

Each process will be described in detail below.

In process (S31), a nucleic acid reaction tool in which the covering body is a light transmissive member is prepared. This nucleic acid reaction tool is a nucleic acid reaction tool according to the second embodiment. The covering body includes first to n-th primer fixing regions, and first to n-th primer sets are fixed thereto respectively. The first to n-th primer sets are primer sets to amplify first to n-th sequences contained in first to nth target nucleic acids contained in the sample respectively.

The process (S32) can be performed by the same method as the above step (S22) using the nucleic acid reaction tool according to the second embodiment.

The process (S33) can be performed by the same method as the above process (S23).

In process (S34), an optical signal changing with an increase of the amplification product is detected for each of the first to n-th primer fixing regions. An optical signal is detected through the covering body from the outside of the nucleic acid reaction tool. An optical signal can be detected by an optical sensor separate from the nucleic acid reaction tool or visually. For example, by individually detecting signals obtained within the range of, for example, 4 mm from each of the first to n-th primer fixing regions, a signal can be obtained for each of the first to n-th primer fixing regions. Accordingly, signals relating to the first to n-th target nucleic acids are individually obtained. Detection may be performed, for example, at the end point of an amplification reaction or may be performed chronologically in the same manner as in the above process (S24).

The process (S35) can be performed by the same method as the above process (S25).

According to the method described above, a plurality of types of target nucleic acids can be detected or quantified with high accuracy without including a detection region.

Third Embodiment

Figure 10:
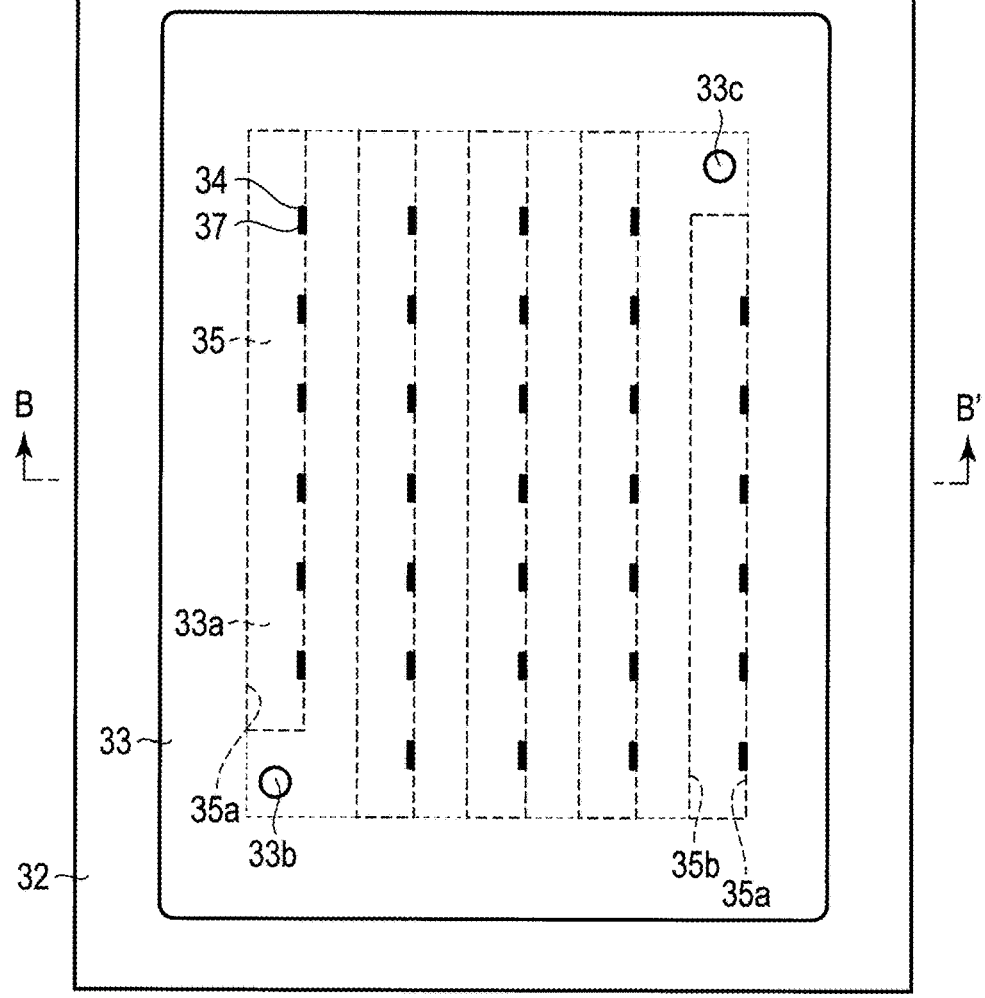
FIG. 10 is a plane view and a sectional view showing an example of a nucleic acid reaction tool according to an embodiment.
Figure 10:
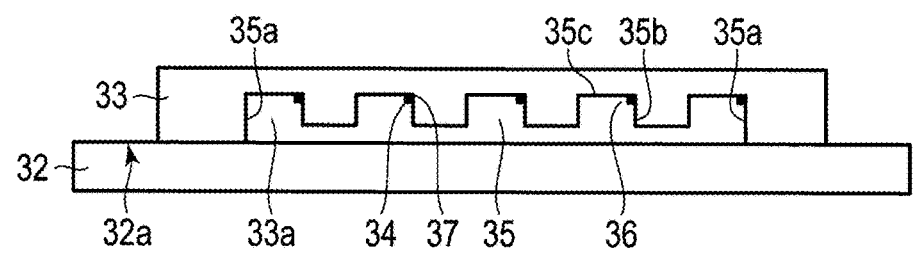

In the nucleic acid reaction tool according to a third embodiment, the shape of the reaction space is not a flow path. An example of the nucleic acid reaction tool according to the third embodiment is shown in FIG. 10. FIG. 10(*a*) is a plane view of a nucleic acid reaction tool 31. FIG. 10(*b*) is a sectional view when the nucleic acid reaction tool 31 is cut along B-B'.

The nucleic acid reaction tool 31 includes a support 32, a covering body 33, and a plurality of types of primer sets 34. As the support 32 and the primer set 34, those that are the same as any ones described above can be used.

A plurality of grooves 33*a* of the covering body 33 is provided at intervals in this example. A side surface 35*a* on the outer side of the groove 33*a* positioned on the outermost side is in contact with an first surface 32*a* of the support 32. However, other side surfaces (for example, a side surface 35*b*) have their lower end not in contact with the first surface 32*a* of the support 32. Therefore, the reaction space 35 has a shape in which a plurality of flow paths is connected to each other on the lower side and integrated. The material of the covering body 33 may be the same as any one described above.

For example, an inlet 33*b* to send the reaction liquid and an outlet 33*c* for discharging the reaction liquid are opened on any surface in contact with the reaction space 35 of the covering body 33.

The primer set 34 is fixed to, for example, a corner 36 where the one end of the side surface 35*b* connected to a rear surface 35*c* of the covering body 33 in the reaction space 35. The primer set 34 may also be fixed to a corner where the one end of the other side surfaces connected to the rear surface.

The nucleic acid reaction tool 31 may include a detection region and/or a probe nucleic acid (not shown) similar to any of the above at a position corresponding to a primer fixing region 37.

Even with the nucleic acid reaction tool as described above, the primer set 34 is fixed to the corner 36 and so the primer set 34 hardly diffuse along the flow of the reaction liquid and diffusion into an undesired range is suppressed. As a result, detection or quantification can be performed more accurately.

Alternatively, the covering body may have one groove so that the reaction space has a shape of one rectangular parallelepiped. In that case, the primer set is fixed to, for example, corners where the one end of the side surface connected to the rear surface of the periphery of the reaction space.

Nucleic Acid Detection/Quantification Kit

According to an embodiment, a nucleic acid detection/quantification kit is provided. The nucleic acid detection/quantification kit includes any of the nucleic acid reaction tools and amplification reagents described above. As the amplification reagent, any of the above amplification reagents selected according to the configuration of the nucleic acid reaction tool can be used.

When the nucleic acid reaction tool does not include a detection reagent, the kit may further include any of the above detection reagents. The type of detection reagent is selected in accordance with the configuration of the nucleic acid reaction tool. For example, if the nucleic acid reaction tool includes an electrode, the kit may include a detection reagent containing a first labeling substance. When the nucleic acid reaction tool includes an optical sensor or a detection window, the kit may include a detection reagent containing a second labeling substance. When the nucleic acid reaction tool does not include a detection region and the covering body is formed of a light transmissive member, the kit may include a detection reagent containing the second labeling substance.

The kit may include a cleaning liquid. The cleaning liquid is a liquid for washing the reaction space. The cleaning liquid is, for example, distilled water, sterile water, a buffer solution, a surfactant solution or the like.

The kit may be contained in one container mixed with each component. Alternatively, each component may be contained in a separate container or some components may be housed in the same container by being combined and mixed.

Nucleic Acid Reaction Cassette

According to an embodiment, a nucleic acid reaction cassette is provided. FIG. 11 is a schematic diagram showing an example of a nucleic acid reaction cassette. A nucleic acid reaction cassette 40 includes a nucleic acid reaction tool 41, and can carry out an amplification reaction of the target nucleic acid and detection or quantification thereof using the nucleic acid reaction tool 41.

The nucleic acid reaction cassette 40 includes the nucleic acid reaction tool 41, a first cassette 42, and a second cassette 43. The nucleic acid reaction tool 41 is any of the nucleic acid reaction tools described above, and includes a support 44, a covering body 45, and a plurality of types of primer sets (not shown).

The first cassette 42 and the second cassette 43 are outer frames that support the nucleic acid reaction tool 41 therebetween. The first cassette 42 and the second cassette 43 are made of, for example, a hard material. In this example, the support 44, the covering body 45, the first cassette 42 and the second cassette 43 are configured as separate bodies. However, the covering body 45 may be formed integrally with the second cassette 43. Alternatively, the covering body 45, the first cassette 42 and the second cassette 43 may be configured as an integral container form. In that case, the nucleic acid reaction tool 41 may be formed by inserting the support 44 into the container.

For example, the nucleic acid reaction cassette 40 may be mounted on an apparatus for use. The apparatus is, for example, an apparatus capable of detecting or quantifying a target nucleic acid by sending a reaction liquid into the reaction space of the nucleic acid reaction tool 41, heating and cooling the reaction space, and detecting a signal generated with an increase of an amplification product generated in the reaction space.

Figure 12:
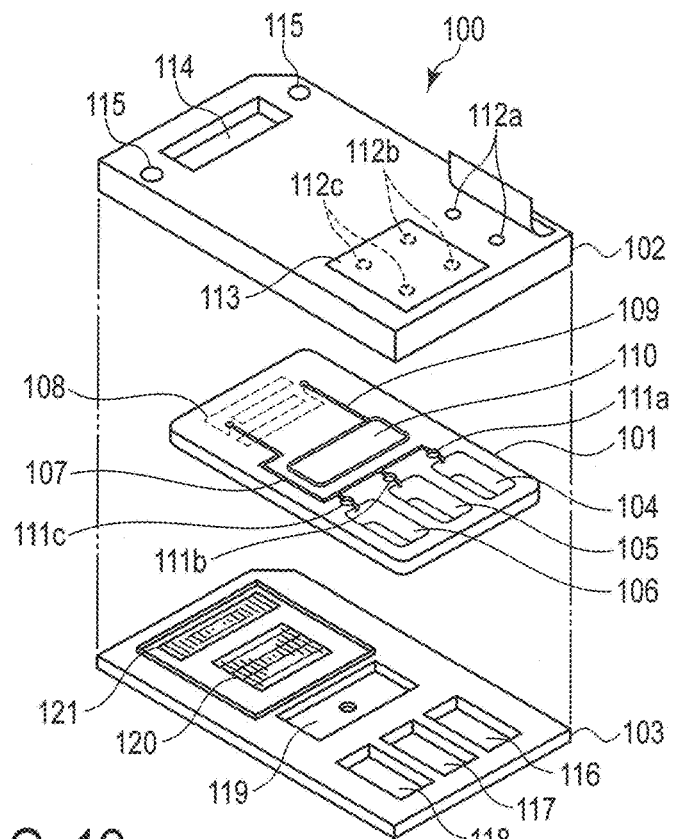
FIG. 12 is a perspective view showing an example of the nucleic acid reaction cassette according to an embodiment.
Figure 13:
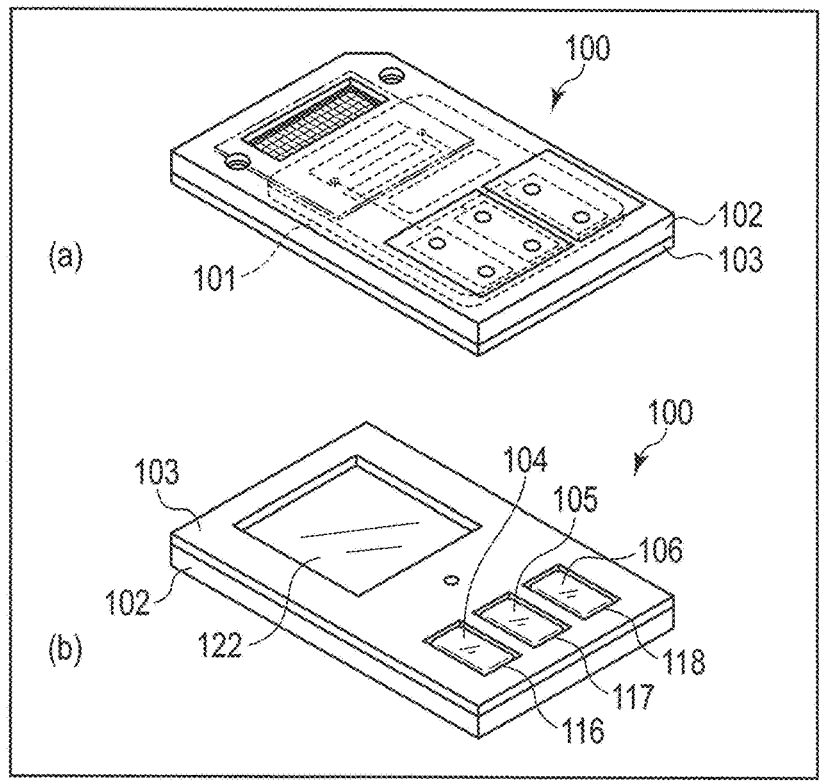
FIG. 13 is a perspective view showing an example of the nucleic acid reaction cassette according to an embodiment.

FIG. 12 is an exploded perspective view showing still another example of the nucleic acid reaction cassette. A nucleic acid reaction cassette 100 includes a covering body 101, an upper plate 102, and a support 103. FIG. 13 is a perspective view showing the nucleic acid reaction cassette 100 shown in FIG. 12 viewed from two directions, from the side of the upper plate 102 (hereinafter, referred to as the front surface. FIG. 13($a$)) and from the side of the support 103 (hereinafter, referred to as the back surface. FIG. 13($b$)).

The covering body 101 includes a reaction liquid syringe 104, a washing syringe 105, a detection reagent syringe 106, a liquid sending flow path 107, a reaction space 108, a waste liquid flow path 109, and a waste liquid syringe 110. The covering body 101 has a thin plate shape having the front surface and the back surface (the second surface). The reaction liquid syringe 104, the washing syringe 105, the detection reagent syringe 106, the liquid sending flow path 107, the reaction space 108, the waste liquid flow path 109, and the waste liquid syringe 110 are integrally formed in the covering body 101.

The reaction liquid syringe 104 can store a reaction liquid. The reaction liquid is any of the above-described reaction liquids containing at least a sample and an amplification reagent. The reaction liquid syringe 104 has an opening on its front surface. The opening is a hole for loading the reaction liquid into the reaction liquid syringe 104. The back surface of the reaction liquid syringe 104 has a container shape having a deformable thin film portion. The thin film portion can be easily crushed by externally applied pressure. The reaction liquid syringe 104 is, for example, initially in a crushed state and the thin film portion side expands by loading of the reaction liquid.

The washing syringe 105 can store a cleaning liquid for cleaning the reaction space 108. The cleaning liquid is, for example, any of the cleaning liquids described above. The washing syringe 105 has the same configuration as the reaction liquid syringe 104.

The detection reagent syringe 106 can store a detection reagent. The detection reagent is, for example, any of the above detection reagents and includes a labeling substance and the like. The detection reagent syringe 106 has the same configuration as the reaction liquid syringe 104.

The liquid sending flow path 107 is a flow path to send the liquids stored in the reaction liquid syringe 104, the washing syringe 105, and the detection reagent syringe 106 to the reaction space 108. The liquid sending flow path 107 branches into three corresponding to each syringe and connects each syringe and the reaction space 108. In addition, check valves 111$a$, 111$b$, 111$c$ are respectively provided in the connecting portions of the liquid sending flow path 107 with the reaction liquid syringe 104, the washing syringe 105, and the detection reagent syringe 106. Each check valve prevents the inflow of liquid from the liquid sending flow path 107 into the corresponding syringe and the outflow of liquid except when sending a liquid from each syringe.

The reaction space 108 is connected to the liquid sending flow path 107 and the waste liquid flow path 109. In the reaction space 108, amplification of the target nucleic acid can be carried out. If necessary, nucleic acid extraction may also be performed in the reaction space 108.

The waste liquid flow path 109 connects the reaction space 108 and the waste liquid syringe 110. The waste liquid flow path 109 is a flow path to send a waste liquid from the reaction space 108 to the waste liquid syringe 110.

The waste liquid syringe 110 can store a waste liquid flowing out from the reaction space 108. The waste liquid syringe 110 has a thin film portion like the reaction liquid syringe 104. The waste liquid syringe 110 is in a state where the thin film portion is crushed in advance before the waste liquid flows in.

The upper plate 102 includes injection ports 112$a$, 112$b$, 112$c$, a detection port 114, and a positioning hole 115. The upper plate 102 has a thin shape and is made of a hard material such as plastic, glass, metal or the like. The upper plate 102 faces and is in close contact with the front surface of the covering body 101. Accordingly, the upper plate 102 seals each syringe and the flow path of the covering body 101.

The injection ports 112$a$, 112$b$, 112$c$ are openings to load a liquid into the reaction liquid syringe 104, the washing syringe 105, and the detection reagent syringe 106 respectively. Each injection port is provided at a position facing the corresponding syringe. Each injection port is sealed with a seal 113 after the liquid is loaded into the syringe.

The detection port 114 faces a pad portion 121 provided on the support 103 without facing the covering body 101. The detection port 114 is an opening to insert a substrate 124 described below.

The positioning hole 115 is an opening used for positioning when the nucleic acid reaction cassette 100 is inserted into a nucleic acid detection/quantification apparatus 200 described below.

The support 103 is formed of the same material as any of the supports described above and has a thin plate shape. The support 103 includes a reaction liquid syringe hole 116, a washing syringe hole 117, a detection reagent syringe hole 118, a waste liquid hollow 119, a plurality of detection regions 120, and a temperature adjustment hole 122. The upper surface (the first surface) of the support 103 faces and is in close contact with the back surface (the second surface) of the covering body 101. Accordingly, the covering body 101 is sealed with the support 103 and the upper plate 102.

The reaction liquid syringe hole 116, the washing syringe hole 117, and the detection reagent syringe hole 118 face the reaction liquid syringe 104, the washing syringe 105, and the detection reagent syringe 106 respectively. The reaction liquid syringe hole 116, the washing syringe hole 117, and the detection reagent syringe hole 118 prevent the support 103 from hindering expansion of the thin film portion of each syringe when a liquid is stored in each syringe.

The waste liquid hollow 119 faces the waste liquid syringe 110. The waste liquid hollow 119 prevents the support 103 from hindering expansion of the thin film portion of the waste liquid syringe 110 when a waste liquid is stored in the waste liquid syringe 110.

The plurality of detection regions 120 has the same configuration as any of the detection regions in the description of the nucleic acid reaction tool according to the first embodiment. The plurality of detection regions 120 faces the reaction space 108 of the covering body 101.

The temperature adjustment hole 122 is provided at a position corresponding to the detection region 120 on the back surface of the support 103. The temperature adjustment hole 122 is a hole for heating and cooling the detection region 120 directly and with high accuracy.

The support 103 includes the pad portion 121 on the front surface facing the detection port 114 of the upper plate 102. The pad portion 121 includes a plurality of pads, each of which electrically connected to each of the plurality of detection regions 120. It is possible to extract a signal obtained by the detection region 120 from the pad.

The covering body 101, the upper plate 102, and the support 103 are assembled such that the covering body 101 is supported by the upper plate 102 and the supporting body 103 by being sandwiched therebetween. The nucleic acid reaction cassette 100 is a hermetically sealed container in which the covering body 101 is sealed. Therefore, the nucleic acid reaction cassette 100 can prevent the reaction liquid from flowing out to the outside. Note that various methods, for example, adhesion, welding, screwing and the like can be used to join the upper plate 102 and the support 103, but not limited thereto.

Figure 14:
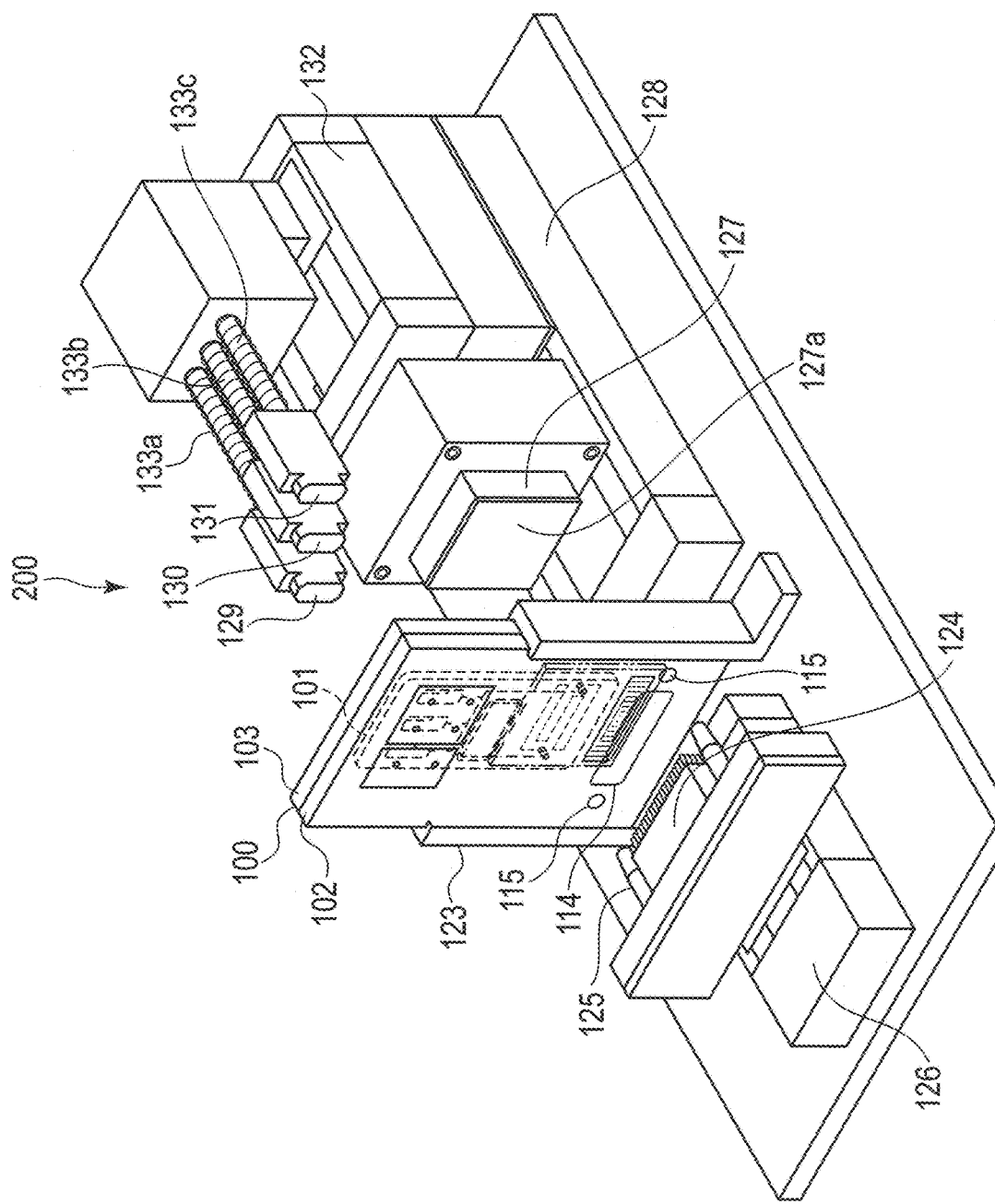
FIG. 14 is a perspective view showing an example of a nucleic acid detection/quantification apparatus according to an embodiment.

FIG. 14 is a perspective view showing an example of the nucleic acid detection/quantification apparatus 200 using the nucleic acid reaction cassette 100. In the present embodiment, the nucleic acid reaction cassette 100 and the nucleic acid detection/quantification apparatus 200 are described as separately configured, but the nucleic acid detection/quantification apparatus 200 may include the nucleic acid reaction cassette 100 in another embodiment.

The nucleic acid detection/quantification apparatus 200 includes a cassette stand 123, a substrate 124, a positioning pin 125, a substrate moving mechanism 126, a heating and cooling device 127, a heating and cooling device moving mechanism 128, a reaction liquid sending rod 129, a cleaning liquid sending rod 130, a detection reagent sending rod 131, a rod moving mechanism 132, and springs 133a, 133b, 133c.

The cassette stand 123 is provided near the center of the nucleic acid detection/quantification apparatus 200. The cassette stand 123 is a member for inserting the nucleic acid reaction cassette 100 into the nucleic acid detection/quantification apparatus 200. For example, the cassette stand 123 is a slot through which the nucleic acid reaction cassette 100 can be inserted and extracted, and which supports the nucleic acid reaction cassette 100.

The substrate 124 is a substrate for acquiring each signal detected by the plurality of detection regions 120 from the pad portion 121. The substrate 124 faces the detection port 114 and can be inserted into and extracted from the detection port 114.

The substrate moving mechanism 126 is mounted with the substrate 124 and the positioning pin 125. The substrate moving mechanism 126 simultaneously moves the substrate 124 and the positioning pin 125 in the forward and backward direction. In the present embodiment, the directions toward and away from the nucleic acid reaction cassette 100 are defined as a forward direction and a backward direction respectively. The substrate 124 and the positioning pin 125 are fitted into a back surface of the nucleic acid reaction cassette 100 by the substrate moving mechanism 126. Accordingly, the substrate 124 comes into contact with the pad portion 121 of the support 103, and the positioning pin 125 is inserted into the positioning hole 115.

The heating and cooling device 127 is provided on the opposite side of the substrate moving mechanism 126 across the cassette stand 123. A heating and cooling unit 127a of the heating and cooling device 127 faces the temperature adjustment hole 122 provided in the support 103. The heating and cooling unit 127a can be inserted into and extracted from the temperature adjustment hole 122.

The heating and cooling device moving mechanism 128 is mounted with the heating and cooling device 127, and moves the heating and cooling device 127 in the forward and backward direction. The heating and cooling device moving mechanism 128 fit the heating and cooling unit 127a of the heating and cooling device 127 into the temperature adjustment hole 122. As a result, the heating and cooling unit 127a comes into contact with the detection region 120. The heating and cooling device 127 controls the detection region 120 and the reaction space 108 to optimum temperatures.

The reaction liquid sending rod 129, the cleaning liquid sending rod 130, the detection reagent sending rod 131, and the rod moving mechanism 132 are provided on the opposite side of the substrate moving mechanism 126 across the cassette stand 123. The rod moving mechanism 132 is mounted with the reaction liquid sending rod 129, the cleaning liquid sending rod 130, and the detection reagent sending rod 131. The rod moving mechanism 132 presses the reaction liquid sending rod 129, the cleaning liquid sending rod 130, and the detection reagent sending rod 131 against the back surface of the nucleic acid reaction cassette 100.

The springs 133a, 133b, 133c are provided between each rod and the rod moving mechanism 132. The springs 133a, 133b, 133c have elasticity that can expand and contract in the moving direction of the rod moving mechanism 132 and contract in the forward and backward direction due to contact between each rod and the nucleic acid reaction cassette 100. Instead of the spring, another elastic body or a mechanical configuration contracting in the forward and backward direction may be used. The spring 133c may not be provided.

The reaction liquid sending rod 129 faces the reaction liquid syringe hole 116. The reaction liquid sending rod 129 has a surface at a tip portion opposite to the nucleic acid reaction cassette 100. This surface has substantially the same shape as the reaction liquid syringe hole 116. The reaction liquid sending rod 129 is inserted into the reaction liquid syringe hole 116. The thin film portion of the reaction liquid syringe 104 is thereby pressurized and the thin film portion is completely crushed. As a result, the reaction liquid in the reaction liquid syringe 104 can be sent out to the liquid sending flow path 107.

The cleaning liquid sending rod 130 faces the washing syringe hole 117. The cleaning liquid sending rod 130 has a surface at a tip portion opposite to the nucleic acid reaction cassette 100. This surface has substantially the same shape as the washing syringe hole 117. The cleaning liquid sending rod 130 is inserted into the washing syringe hole 117. The thin film portion of the washing syringe 105 is thereby pressurized, and the thin film portion is completely crushed. As a result, the cleaning liquid in the washing syringe 105 can all be sent out to the liquid sending flow path 107.

The detection reagent sending rod 131 faces the detection reagent syringe hole 118. The detection reagent sending rod 131 has a surface at a tip portion opposite to the nucleic acid reaction cassette 100. This surface has substantially the same shape as the washing syringe hole 117. The detection reagent sending rod 131 is inserted into the detection reagent syringe hole 118. The thin film portion of the detection reagent syringe 106 is thereby pressurized and the thin film portion is completely crushed. As a result, the detection reagent in the detection reagent syringe 106 can all be sent out to the liquid sending flow path 107.

Because the reaction liquid sending rod 129, the cleaning liquid sending rod 130, and the detection reagent sending rod 131 have different lengths, the thin film portion of the corresponding syringe can be pressurized in the order of the reaction liquid sending rod 129, the cleaning liquid sending rod 130, and the detection reagent sending rod 131 by gradually advancing all the rods.

Next, an example of the procedure for using the nucleic acid reaction cassette 100 and the nucleic acid detection/quantification apparatus 200 according to the present embodiment and the procedure for detecting or quantifying a nucleic acid using the cassette 100 and the apparatus 200 will be described. The procedures described below are by way of example and can be appropriately replaced.

First, an example of the procedure for preparing the nucleic acid reaction cassette 100 will be described. A reaction liquid is loaded into the reaction liquid syringe 104 of the nucleic acid reaction cassette 100, a cleaning liquid is loaded into the washing syringe 105, and a detection reagent is loaded into the detection reagent syringe 106 via the injection ports 112a, 112b, and 112c respectively. The injection port 112 is sealed with a cap seal 113. The nucleic acid reaction cassette 100 is inserted into the cassette stand 123 in such a direction that each syringe is on the upper side and the upper plate 102 faces the substrate 124.

Next, the substrate 124 and the positioning pin 125 are advanced toward the nucleic acid reaction cassette 100 by the substrate moving mechanism 126. Then, the substrate 124 is brought into contact with the pad portion 121 and at the same time, the positioning pin 125 is inserted into the positioning hole 115.

Next, the reaction liquid sending rod 129, the cleaning liquid sending rod 130, and the detection reagent sending rod 131 are advanced toward the nucleic acid reaction cassette 100 by the rod moving mechanism 132. Then, the reaction liquid sending rod 129 is pushed to the reaction liquid syringe 104 through the reaction liquid syringe hole 116. Accordingly, all the reaction liquids are sent out to the reaction space 108 via the liquid sending flow path 107. The air in the reaction space 108 is extruded by the sending of the reaction liquid and flows into the waste liquid syringe 110 via the waste liquid flow path 109. At this point, the tip portion of the cleaning liquid sending rod 130 and the tip portion of the detection reagent sending rod 131 are not in contact with the washing syringe 105 and the detection reagent syringe 106 respectively.

Next, the heating and cooling device 127 is advanced toward the nucleic acid reaction cassette 100 by the heating and cooling device moving mechanism 128. Then, the heating and cooling unit 127a is brought into contact with the detection region 120 through the temperature adjustment hole 122. Next, the heating and cooling device 127 is operated to heat the reaction space 108. As a result, nucleic acid amplification is performed in the reaction space 108, and if any target nucleic acid is present in the reaction liquid, the target nucleic acid is amplified. When the probe nucleic acid is fixed to the detection region 120, hybridization of the amplification product with the probe nucleic acid occurs.

Next, each rod is advanced toward the nucleic acid reaction cassette 100 by the rod moving mechanism 132. Then, the cleaning liquid sending rod 130 is pushed to the washing syringe 105 through the washing syringe hole 117. Accordingly, all the cleaning liquids are sent out to the reaction space 108 via the liquid sending flow path 107. Then, the cleaning liquid cleans the reaction space 108. At this point, the tip portion of the detection reagent sending rod 131 is not in contact with the detection reagent syringe 106. When the cleaning liquid is sent into the reaction space 108, all the reaction liquid in the reaction space 108 flows into the waste liquid syringe 110 through the waste liquid flow path 109. Note that the cleaning process may not be performed. When the probe nucleic acid is fixed to the detection region 120, the cleaning process may be performed.

Next, each rod is advanced toward the nucleic acid reaction cassette 100 by the rod moving mechanism 132. Accordingly, all detection reagents are sent out to the reaction space 108 via the liquid sending flow path 107. As a result of the inflow of the detection reagents, the cleaning liquid in the reaction space 108 completely flows into the waste liquid syringe 110 through the waste liquid flow path 109. When the detection reagent is not used or when the detection reagent is contained in the reaction liquid, this process may be omitted.

Then, a signal associated with the amplification product detected by the detection region 120 is extracted from the pad portion 121 using the substrate 124. Based on the information of the extracted signal, the target nucleic acid is detected or quantified using any one of the methods described above. Detection and/or quantification may be performed automatically, for example, by a computer electrically connected to the substrate 124. Further, for example, all or a portion of the above procedure may be controlled and automatically performed by a control unit contained in the computer.

When cleaning is not done, the nucleic acid reaction cassette 100 and the nucleic acid detection/quantification apparatus 200 may not include the washing syringe 105, the check valve 111b, the injection port 112b, the washing syringe hole 117, the cleaning liquid sending rod 130, and the spring 133b.

When a detection reagent is contained in the reaction liquid, the nucleic acid reaction cassette 100 and the nucleic acid detection/quantification apparatus 200 may not include the detection reagent syringe 106, the check valve 111c, the injection port 112c, the detection reagent syringe hole 118, the detection reagent sending rod 131, and the spring 133c.

According to the present embodiment, the nucleic acid reaction cassette 100 and the nucleic acid detection/quantification apparatus 200 using the nucleic acid reaction cassette 100 can more accurately amplify and detect or quantify a plurality of target nucleic acids with one nucleic acid reaction tool.

EXAMPLES

[Example 1] (Example)

Preparation of Support and Covering Body

Thin films of titanium (500 nm) and gold (2000 nm) were formed by sputtering on the glass surface of Pyrex (registered trademark) (d=0.8 mm). Then, using a resist AZP4620, an array of gold electrodes (φ=200 μM) (working electrode) was formed. As the working electrode, 60 electrodes A1 to A60 were formed so as to be arranged two each with spaces (2 mm). A reference electrode and a counter electrode corresponding to every two working electrodes were formed. Further, a flow path was formed on a silicone plate by etching to produce a covering body.

Fixing of Primer

The covering body was lightly rinsed by soaking the covering body in a 10 mm Tris-HCl (8.0)-0.1% Tween 20 solution and lightly rinsed, and then air-dried. Subsequently, 0.25 μL of LAMP primer mix was prepared. The primer mix contains FIP primer and BIP primer: 1.6 μM, F3 primer and B3 primer: 0.2 μM, and FITC-Lb: 0.8 μM. The sequence of each primer contained in the LAMP primer mix is shown in Table 1.

TABLE 1

| SEQ ID NO | | Sequence |
|---|---|---|
| 1 | F3 | GAGATATTATTTTCAATGGGATAGAAC |
| 2 | B3 | CAATGCTCTATTTGTTTGCCATG |
| 3 | FIP | GAACATCATCTGGATCTGTACCAACCATCTCATACTGGAACTAGTGGC |
| 4 | BIP | CTGTGCCAGTACACTTACTAAGAGTGTTAGTCTACATGGTTTACAATC |
| 5 | Lb | ACAGGTGATGAATTTGCTACAGG |

Figure 15:
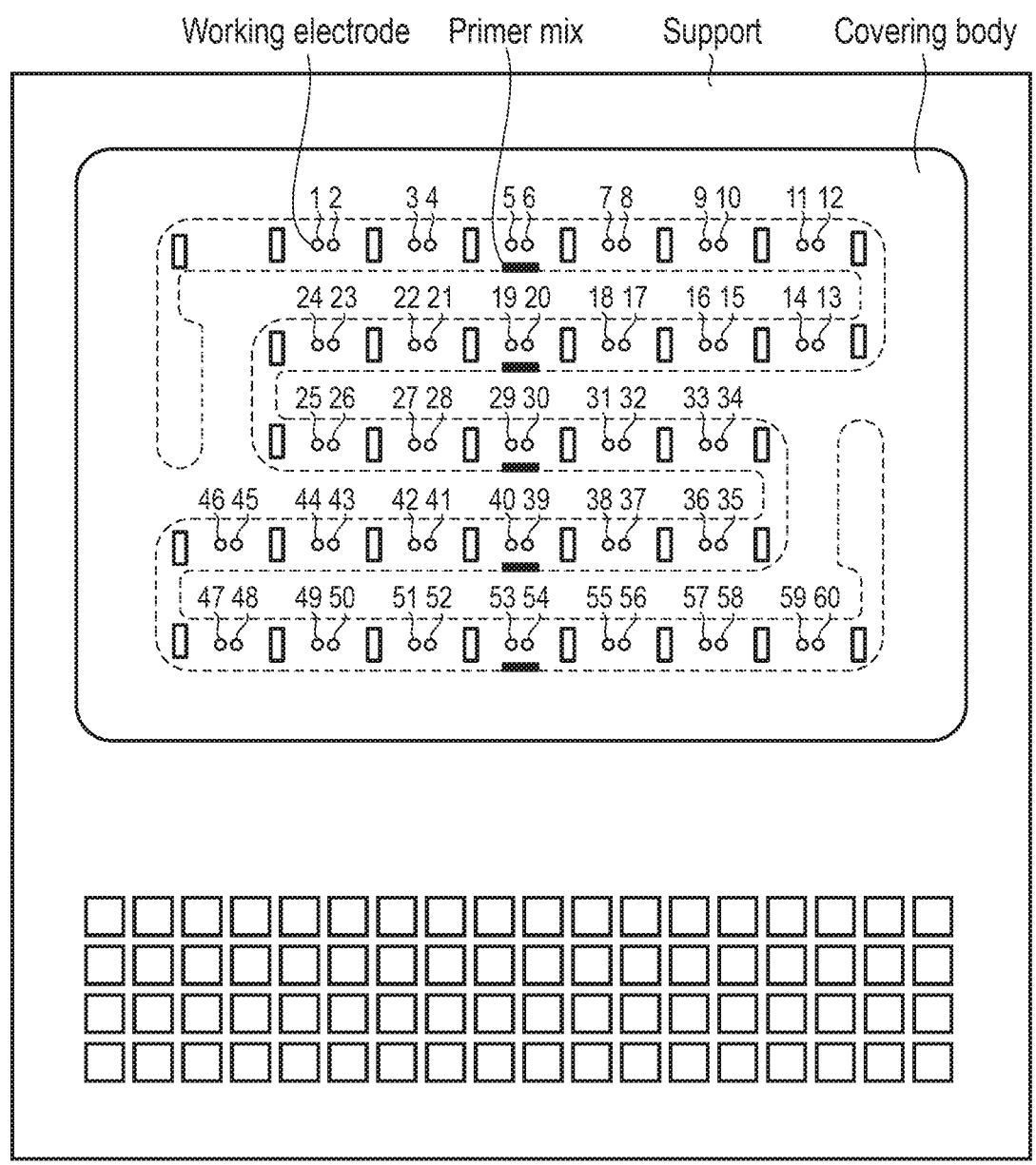
FIG. 15 is a schematic diagram showing the nucleic acid reaction tool used in Example 1; the numbers '1,2'; '3,4' . . . '59,60' represent working electrodes and correspond to working electrodes A1 to A60 in Example 1.

The primer mix was spotted in the corner of the flow path of the covering body. FIG. 15 is a schematic view showing the relationship between the position of the working electrode of the support and the position where the primer set of the covering body is spotted. FIG. 15 shows a state in which a nucleic acid reaction tool is formed by bonding a support and a covering body. For the sake of convenience, spotting was carried out at one point (five points in total) per row of serpentine flow paths. The positions of the spotted primer sets correspond to working electrodes A5 and A6, A19 and A20, A29 and A30, A39 and A40.

Figure 16:
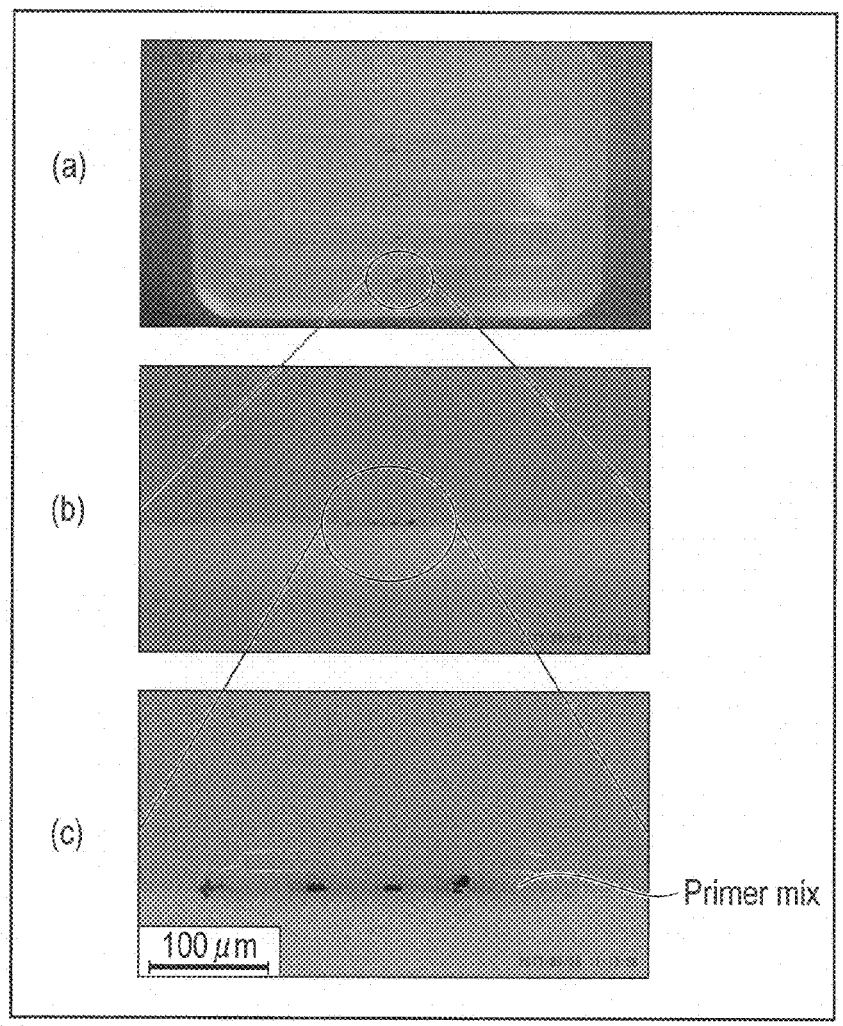
FIG. 16 is a diagram showing photographs of a covering body of Example 1 to which a primer set is fixed.

Next, the covering body was left at room temperature to naturally dry and fix the primer mix. FIG. 16 shows a photograph of the fixed primer mix. FIG. 16(a) is a photograph showing the entire covering body. FIG. 16(b) is a photograph showing one fixed primer mix. FIG. 16(c) is a further enlarged picture of the primer mix of FIG. 16(b). The blue portion is a pigment mixed to make the primer mix easier to see. From these photographs, it was confirmed that the primer mix was fixed to the corner of the flow path of the covering body.

The support and the covering body were crimped to form a reaction space in which the flow path is sealed, thereby forming a nucleic acid reaction tool.

LAMP Reaction

A reaction liquid containing an artificial sequence of parvovirus (sequence number 1) was prepared. The base sequence of the artificial sequence of parvovirus is shown in Table 2. The composition of the reaction liquid is shown in Table 3.

TABLE 2

VP gene of Parvo virus (SEQ ID NO 6)

AAACGCTAATACGACTCACTATAGGGCGATCTACGGGTACTTTCAATAAT

CAGACGGAATTTAAATTTTTGGAAAACGGATGGGTGGAAATCACAGCAAA

CTCAAGCAGACTTGTACATTTAAATATGCCAGAAAGTGAAAATTATAGAA

GAGTGGTTGTAAATAATTTGGATAAAACTGCAGTTAACGGAAACATGGCT

TTAGATGATACTCATGCACAAATTGTAACACCTTGGTCATTGGTTGATGC

AAATGCTTGGGGAGTTTGGTTTAATCCAGGAGATTGGCAACTAATTGTTA

ATACTATGAGTGAGTTGCATTTAGTTAGTTTTGAACAAGAAATTTTTAAT

GTTGTTTTAAAGACTGTTTCAGAATCTGCTACTCAGCCACCAACTAAAGT

TTATAATAATGATTTAACTGCATCATTGATGGTTGCATTAGATAGTAATA

ATACTATGCCATTTACTCCAGCAGCTATGAGATCTGAGACATTGGGTTTT

TATCCATGGAAACCAACCATACCAACTCCATGGAGATATTATTTTCAATG

GGATAGAACATTAATACCATCTCATACTGGAACTAGTGGCACACCAACAA

ATATATACCATGGTACAGATCCAGATGATGTTCAATTTTATACTATTGAA

AATTCTGTGCCAGTACACTTACTAAGAACAGGTGATGAATTTGCTACAGG

AACATTTTTTTTGATTGTAAACCATGTAGACTAACACATACATGGCAAA

CAAATAGAGCATTGGGCTTACCACCATTTCTAAATTCTTTGCCTCAAGCT

GAAGGAGGTACTAACTTTGGTTATATAGGAGTTCAACAAGATAAAAGACG

TGGTGTAACTCAAATGGGAAATACAAACTATATTACTGAAGCTACTATTA

TGAGACCAGCTGAGGTTGGTTATAGTGCACCATATTATTCTTTTGAGGCG

TCTACACAAGGGCCATTTAAAACACCCTTCCCTTTAGTGAGGGTTAATAA

TABLE 3

| Components | Final concentration |
|---|---|
| Tris-HCl (pH 8.0) | 20 mM |
| KCl | 60 mM |
| MgSO4 | 8 mM |
| (NH4)2SO4 | 10 mM |
| Tween20 | 0.10% |
| dNTPs | 1.4 mM each |
| GspSSD polymerase | 32 units (x2) |
| Betaine | 0.8M |
| RuHex | 0.75 mM |

Figure 17:
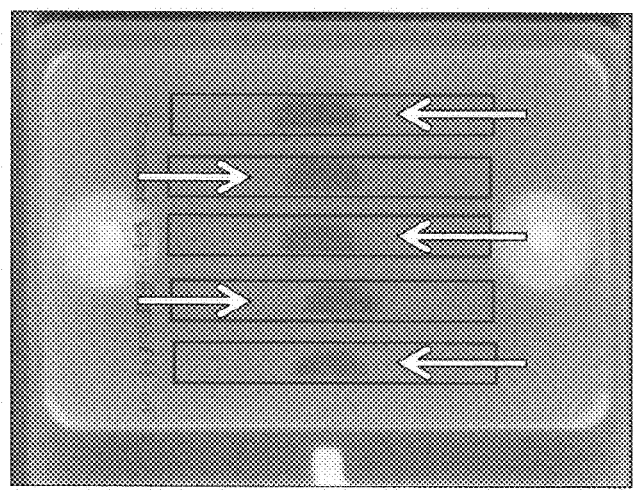
FIG. 17 is a photograph of the primer set after inflow of a reaction liquid of Example 1.

The reaction liquid was brought into the reaction space of the nucleic acid reaction tool. FIG. 17 shows a photograph of the covering body after the reaction liquid was brought. The photograph was taken by a fluorescence image analyzer. From this photograph, it was confirmed that primer set was hardly dissolved and/or diffused along the liquid flow (arrow in the drawing) during injection of the reaction liquid.

The reaction liquid was heated at an isothermal temperature of 67° C. to start the amplification reaction. In parallel with the amplification reaction, the electric signal was measured by the LSV method (sweep rate: 0.5V/s). The measurement was chronologically made for one hour.

Figure 18D:
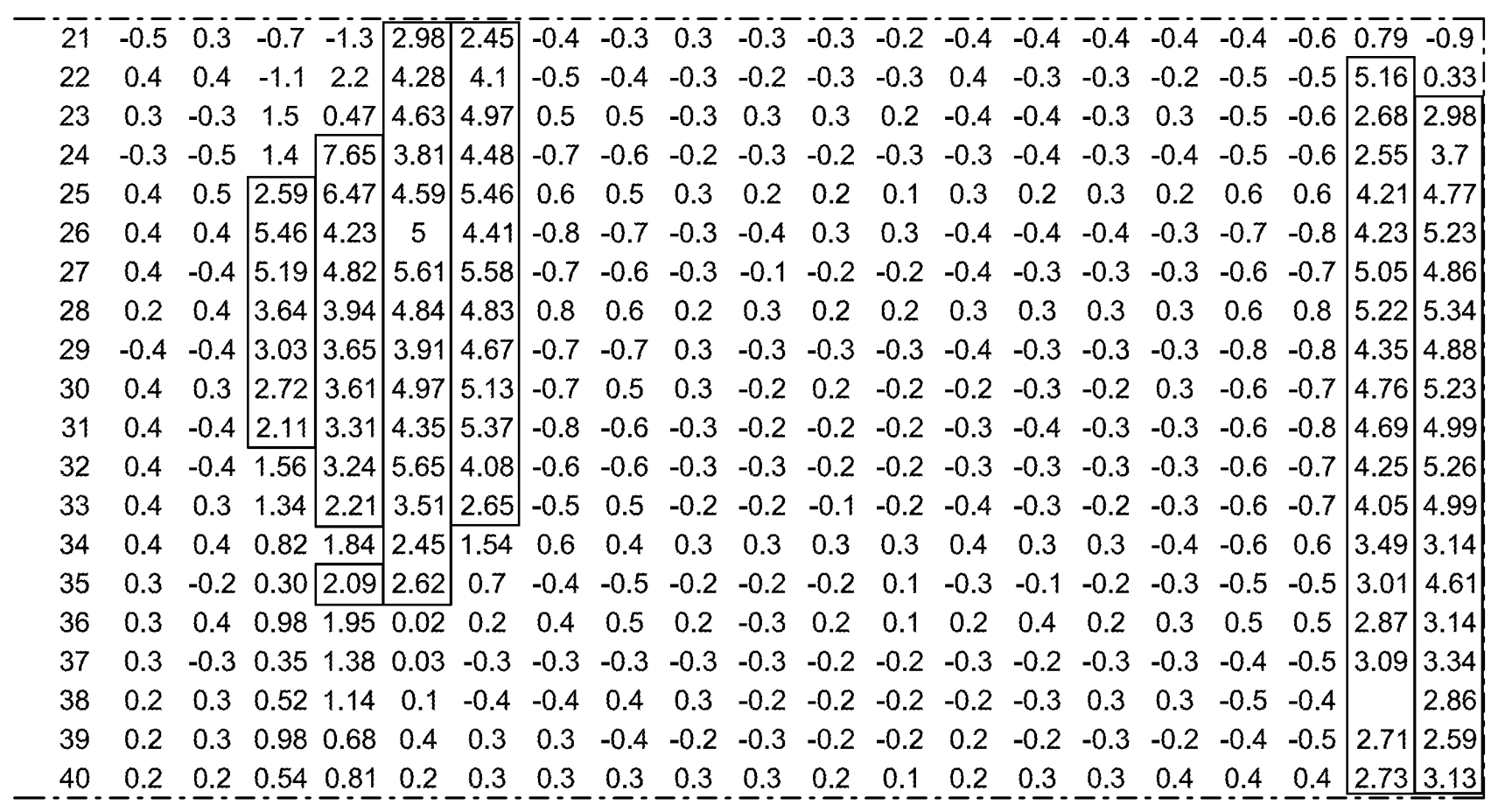
Figure 18E:
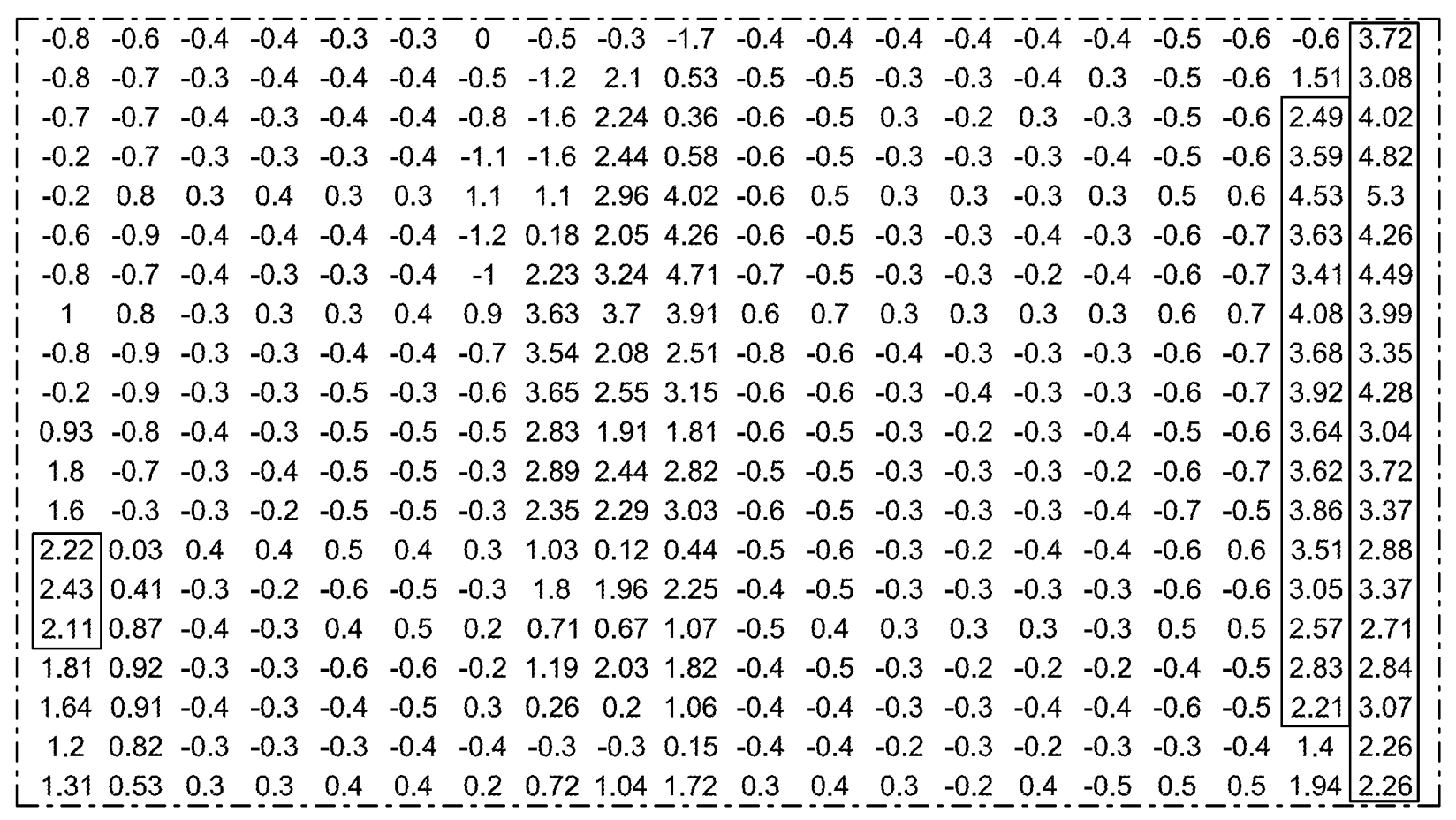
Figure 18H:
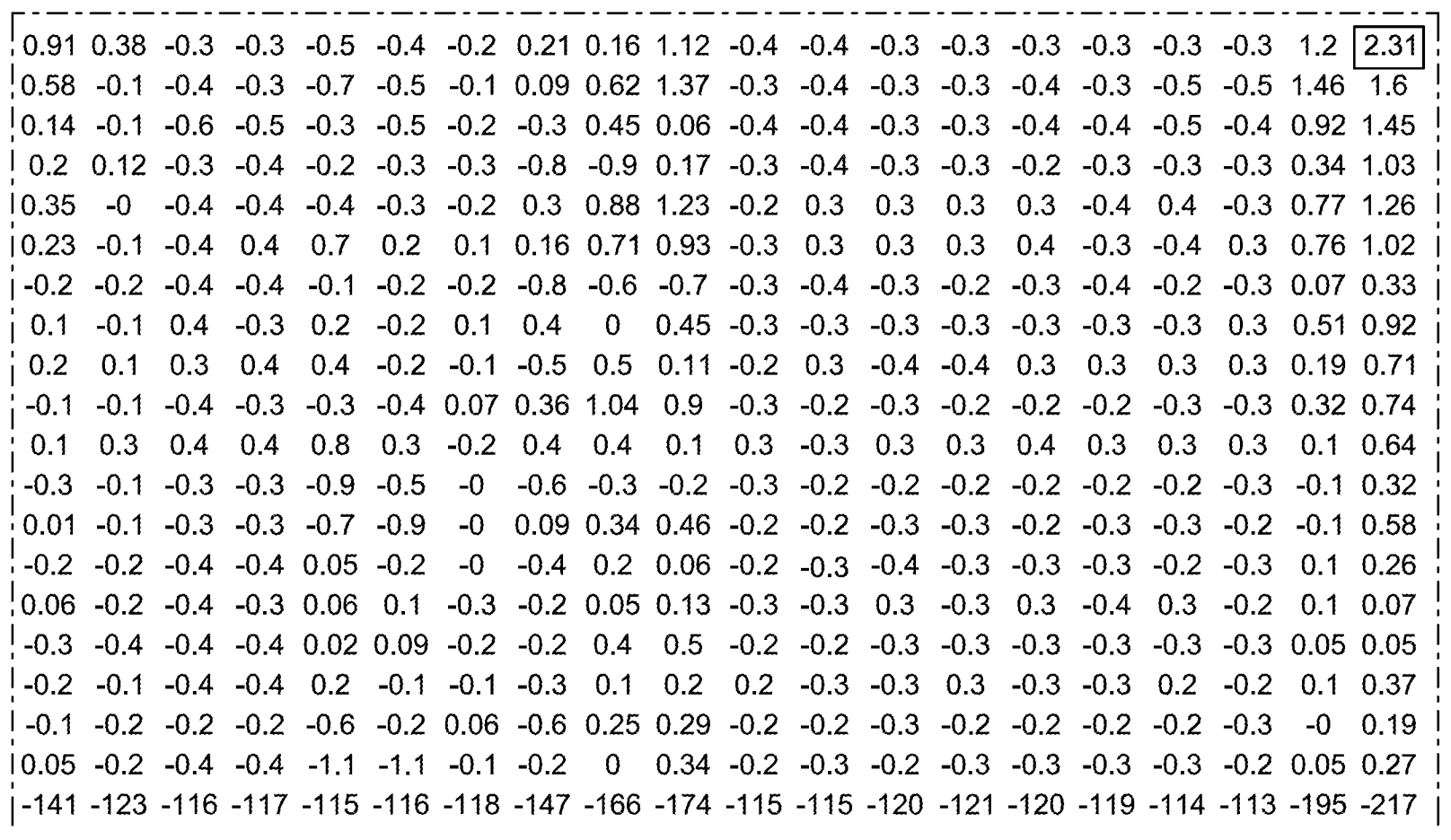

The results are shown in FIG. 18. FIG. 18 shows a table being inputted the intensity of signals obtained by each working electrode every one minute and being shaded cells having the value of signal increase change with respect to time that exceeds 1 nanoampere/min. The value of change exceeding 1 nanoampere/min means that a signal rises in the working electrode, that is, an amplification product is generated near the working electrode.

The rise of a current value was only detected in the working electrode with the primer mix fixed or the working electrode next to one side of the working electrode. Therefore, it became clear that the diffusion of the primer mix into the reaction liquid remained within 2 mm on one side.

[Example 2] (Comparative Example)

The same experiment as in Example 1 was carried out by fixing the primer mix to the surface of the support in the reaction space, instead of the covering body. The primer mix was fixed to positions corresponding to the electrodes A2 and A3, A9 and A10, A15 and A16, A22 and A23, A26 and A27, A33 and A34, A35 and A36, A42 and A43, A50 and A51, and A57 and A58. The results are shown in FIG. 19. In all the primer mixes, the electrode in which the rise of the current value was observed was displaced along the flow of the reaction liquid inflow. Also, the electrodes where the rise of the current value was observed were spread widely.

From the results of Examples 1 and 2, it turned out that fixing the primer set to the corner of the covering body makes it difficult for the primer set to dissolve and diffuse along the flow of the reaction liquid. Therefore, according to the nucleic acid reaction tool in an embodiment, it is suggested that a plurality of target nucleic acids can be detected or quantified more accurately.

[Example 3] (Example)

Preparation of Support and Covering Body

Pyrex (registered trademark) (d=0.8 mm) glass was used as a support. A flow path was formed on a silicone plate to produce a covering body.

Fixing of Primer

The silicone covering body having flow path was immersed in 10 mm Tris-HCl (8.0)-0.1% Tween 20, lightly rinsed, and then air-dried. Subsequently, 0.25 μL of LAMP primer mix was prepared. The LAMP primer mix contains FIP primer and BIP primer: 1.6 μM, F3 primer and B3 primer: 0.2 μM, FITC-Lb: 0.8 μM, and 0.005% xylene cyanol. The sequence of each primer of the LAMP primer mix is the same as that used in Example 1.

Like in Example 1, the primer mix was fixed to the corner of the flow path of the covering body, and the support and the covering body were crimped to form a reaction space in which the flow path was sealed to form a nucleic acid reaction tool.

LAMP Reaction

A reaction liquid containing an artificial sequence of parvovirus (sequence number 1) was prepared. The reaction liquid contains the fluorescent dye EvaGreen, instead of RuHex in the reaction liquid of Example 1.

The reaction liquid was brought into the reaction space of the nucleic acid reaction tool. A photograph of the covering body after the reaction liquid was brought is shown in FIG. 20(*a*). From this photograph, it was confirmed that primer set was hardly dissolved and/or diffused along the liquid flow (arrow in the drawing) during injection of the reaction liquid.

The reaction liquid was heated at an isothermal temperature of 67° C. to start the amplification reaction. After the amplification, the reaction space was photographed by a fluorescence image analyzer.

The results are shown in FIG. 20(*b*). The fluorescence derived from an amplification product generated with the progress of an amplification reaction was obtained from the left and right uniform regions in the vicinity of the position where the primer was fixed. Therefore, it was shown that the fixed primer did not migrate along the flow of the reaction liquid, but diffused in a local region and the amplification reaction proceeded in that range.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A nucleic acid reaction tool comprising:
a support comprising a first surface, a covering body having a second surface, and a groove opened on the second surface, and at least one primer set,
wherein the second surface of the covering body is in contact with the first surface of the support to form a reaction space surrounded by the first surface and the groove, wherein the groove comprises, on an inner surface of the reaction space, a first side surface and a second side surface opposed to each other, a rear surface connecting one end of each of the first and the second side surfaces, and at least one primer fixing region, to which the at least one primer set is fixed, located at a corner where the one end of the first side surface is connected to the rear surface in the reaction space, at a corner where the one end of the second side surface is connected to the rear surface in the reaction space, or a combination thereof.

2. The nucleic acid reaction tool of claim 1, wherein
the tool comprises a plurality of types of the primer sets,
the groove comprises a plurality of the primer fixing regions, and
the plurality of types of the primer sets are releasably fixed to the plurality of the primer fixing regions by type.

3. The nucleic acid reaction tool of claim 2, wherein the plurality of the primer fixing regions are arranged at a distance of 1 mm to 8 mm from each other in the groove.

4. The nucleic acid reaction tool of claim 1, wherein the covering body is made from a hydrophobic resin.

5. The nucleic acid reaction tool of claim 4, wherein the hydrophobic resin is a silicone resin.

6. The nucleic acid reaction tool of claim 1, wherein the reaction space is a flow path.

7. The nucleic acid reaction tool of claim 1, wherein the support further comprises a detection region corresponding to the primer fixing region.

8. The nucleic acid reaction tool of claim 7, wherein the detection region comprises an electrode.

9. The nucleic acid reaction tool of claim 7, wherein the detection region comprises an optical sensor.

10. A nucleic acid detection/quantification kit comprising: the nucleic acid reaction tool of claim 1 and an amplification reagent.

11. The kit of claim 10, further comprising a detection reagent containing a labeling substance.

12. The nucleic acid reaction tool of claim 1, wherein the cross section of a part of the reaction space where the primer fixing region is arranged is the same as a part where the primer fixing region is not arranged.

13. The nucleic acid reaction tool of claim 1, further comprising a plurality of reaction spaces.

14. The nucleic acid reaction tool of claim 1, wherein the at least one primer fixing region at the corner is coated with a surfactant.

15. A method for detecting or quantifying first to n-th target nucleic acids in a sample, where n being an integer equal to 2 or greater,
the method comprising:
(S1) preparing a nucleic acid reaction tool
wherein the nucleic acid reaction tool comprises:
a support comprising a first surface, a covering body having a second surface, and a groove opened on the second surface, and a first to n-th primer set,
wherein the second surface of the covering body is in contact with the first surface of the support to form a reaction space surrounded by the first surface and the groove,
the groove comprises, on an inner surface of the reaction space, a first side surface and a second side surface opposed to each other, a rear surface connecting one end of the first and the second side surfaces, and a first to n-th primer fixing regions to which the first to n-th primer sets are fixed respectively, the first to n-th primer fixing regions being located at a corner where the one end of the first side surface is connected to the rear surface in the reaction space, at a corner where the one end of the second side surface is connected to the rear surface in the reaction space, or a combination thereof,
the first to n-th primer sets are primer sets to amplify first to n-th sequences contained in the first to n-th target nucleic acids respectively;
(S2) bringing a reaction liquid containing a sample and an amplification reagent into the reaction space of the nucleic acid reaction tool;
(S3) maintaining the reaction space under amplification conditions to obtain an amplification product;
(S4) detecting a signal change with an increase of the amplification product for each of the first to n-th primer fixing regions; and
(S5) detecting or quantifying the first to n-th target nucleic acids based on detection results.

16. The method of claim 15, wherein a cross section of a part of the reaction space of the nucleic acid reaction tool where the primer fixing region is arranged is the same as a part where the primer fixing region is not arranged.

17. The method of claim 15, wherein the nucleic acid reaction tool comprises a plurality of reaction spaces.

18. The method of claim 15, wherein the first to n-th primer fixing regions are each coated with a surfactant.

* * * * *

SEQUENCE LISTING

```
<160> NUMBER OF SEQ ID NOS: 6

<210> SEQ ID NO 1
<211> LENGTH: 27
<212> TYPE: DNA
<213> ORGANISM: Artificial Sequence
<220> FEATURE:
<223> OTHER INFORMATION: Synthetic primer

<400> SEQUENCE: 1
gagatattat tttcaatggg atagaac                                         27

<210> SEQ ID NO 2
<211> LENGTH: 23
<212> TYPE: DNA
<213> ORGANISM: Artificial Sequence
<220> FEATURE:
<223> OTHER INFORMATION: Synthetic primer
```

<400> SEQUENCE: 2
caatgctcta tttgtttgcc atg					23

<210> SEQ ID NO 3
<211> LENGTH: 48
<212> TYPE: DNA
<213> ORGANISM: Artificial Sequence
<220> FEATURE:
<223> OTHER INFORMATION: Synthetic primer

<400> SEQUENCE: 3
gaacatcatc tggatctgta ccaaccatct catactggaa ctagtggc		48

<210> SEQ ID NO 4
<211> LENGTH: 48
<212> TYPE: DNA
<213> ORGANISM: Artificial Sequence
<220> FEATURE:
<223> OTHER INFORMATION: Synthetic primer

<400> SEQUENCE: 4
ctgtgccagt acacttacta agagtgttag tctacatggt ttacaatc		48

<210> SEQ ID NO 5
<211> LENGTH: 23
<212> TYPE: DNA
<213> ORGANISM: Artificial Sequence
<220> FEATURE:
<223> OTHER INFORMATION: Synthetic primer

<400> SEQUENCE: 5
acaggtgatg aatttgctac agg					23

<210> SEQ ID NO 6
<211> LENGTH: 1000
<212> TYPE: DNA
<213> ORGANISM: Parvo virus

<400> SEQUENCE: 6
aaacgctaat acgactcact atagggcgat ctacgggtac tttcaataat cagacggaat		60
ttaaattttt ggaaaacgga tgggtggaaa tcacagcaaa ctcaagcaga cttgtacatt		120
taaatatgcc agaaagtgaa aattatagaa gagtggttgt aaataatttg dataaaactg		180
cagttaacgg aaacatggct ttagatgata ctcatgcaca aattgtaaca ccttggtcat		240
tggttgatgc aaatgcttgg ggagtttggt ttaatccagg agattggcaa ctaattgtta		300
atactatgag tgagttgcat ttagttagtt ttgaacaaga aatttttaat gttgttttaa		360
agactgtttc agaatctgct actcagccac caactaaagt ttataataat gatttaactg		420
catcattgat ggttgcatta gatagtaata atactatgcc atttactcca gcagctatga		480
gatctgagac attgggtttt tatccatgga aaccaaccat accaactcca tggagatatt		540
atttttcaatg ggatagaaca ttaataccat ctcatactgg aactagtggc acaccaacaa		600
atatatacca tggtacagat ccagatgatg ttcaattta ctattgaa aattctgtgc		660
cagtacactt actaagaaca ggtgatgaat ttgctacagg aacatttttt tttgattgta		720
aaccatgtag actaacacat acatggcaaa caaatagagc attgggctta ccaccatttc		780
taaattcttt gcctcaagct gaaggaggta ctaactttgg ttatatagga gttcaacaag		840

-continued

```
ataaaagacg tggtgtaact caaatgggaa atacaaacta tattactgaa gctactatta      900
tgagaccagc tgaggttggt tatagtgcac catattattc ttttgaggcg tctacacaag      960
ggccatttaa aacacccttc cctttagtga gggttaataa                           1000
```